United States Patent
Bradbury et al.

(10) Patent No.: US 6,593,326 B1
(45) Date of Patent: Jul. 15, 2003

(54) 2,4-DIAMINO PYRIMIDINE COMPOUNDS HAVING ANTI-CELL PROLIFERATIVE ACTIVITY

(75) Inventors: Robert H Bradbury, Macclesfield (GB); Gloria A Breault, Macclesfield (GB); Philip J Jewbury, Macclesfield (GB); Janet E Pease, Macclesfield (GB)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/868,602

(22) PCT Filed: Dec. 20, 1999

(86) PCT No.: PCT/GB99/04325

§ 371 (c)(1),
(2), (4) Date: Jun. 20, 2001

(87) PCT Pub. No.: WO00/39101

PCT Pub. Date: Jul. 6, 2000

(30) Foreign Application Priority Data

Dec. 24, 1998 (GB) .............................................. 9828511

(51) Int. Cl.$^7$ .................... C07D 239/48; C07D 401/12; A61K 31/505

(52) U.S. Cl. .................... 514/235.8; 514/275; 544/122; 544/323

(58) Field of Search ................ 544/122, 323; 514/235.8, 275

(56) References Cited

U.S. PATENT DOCUMENTS

| | | | |
|---|---|---|---|
| 4,983,608 A | 1/1991 | Effland et al. | 514/256 |
| 5,516,775 A | 5/1996 | Zimmermann et al. | 514/224.2 |
| 5,521,184 A | 5/1996 | Zimmermann | 514/252 |
| 5,610,303 A | 3/1997 | Kimura et al. | 544/326 |
| 5,739,143 A | 4/1998 | Adams et al. | 514/275 |
| 5,859,041 A | 1/1999 | Liverton et al. | 514/396 |

FOREIGN PATENT DOCUMENTS

| | | |
|---|---|---|
| CA | 2231765 | 9/1998 |
| EP | 0 363 002 | 4/1990 |
| EP | 0 379 806 B1 | 8/1990 |
| EP | 0 945 443 A1 | 9/1999 |
| WO | WO 91/18887 | 12/1987 |
| WO | WO 92/20642 | 11/1992 |
| WO | WO 95/09847 | 4/1995 |
| WO | WO 95/09851 | 4/1995 |

(List continued on next page.)

OTHER PUBLICATIONS

Chemical Abstracts, vol. 95, No. 11, 1981, Columbus Ohio, US; abstract No. 97712f, Ghosh, D: "2,4–BIS (Arylamino)–6–Methylpyrimidines as Antimicrobial Agents" p. 648; XP002109184 abstract & J.Indian Chem. Soc., vol. 58, No. 5, 1981, pp. 512–513, India.

El–Kerdawy et al.; 2,4–Bis (Substituted)–5–Nitropyrimidines of Expected Diuretic Action; Egypt J. Chem. vol. 29, No. 2, 1986, pp. 247–251.

Fiziol Akt Veshchestva, 1975, vol. 7, pp. 68–72.

Ghosh et a.l; 2,4–Bis(arylamino)–5–methylpyrimidines as Antimicrobial Agents;; J. Med. Chem., 1967, vol. 10, No. 5, pp. 974–975.

Ghosh, 2,4–Bis(Arylamino)–6–Methyl Pyrimidines as Antimicrobial Agents, J. Indian Chem. Soc., vol. 58, No. 5, 1981, pp. 512–513.

Schmidt et al.; "A Convenient Synthesis of 2–substituted 4–Amino–5–pyrimidinecarbonitriles"; J. Heterocycle Chem., 1997, vol. 24, No. 5, pp. 1305–1307.

Boschelli et al., Synthesis and Tyrosine Kinase Inhibitory Activity of a Series of 2–Amino–8–H–pyrido[2,3–d]pyrimidines: Identifidation of Potent, Selective Platelet–Derived Growth Factor Receptor Tyrosine Kinase Inhibitors, J. Med. Chem., vol. 41, 1998, pp. 4365–4377.

Deady et al., "Reactions of some Quinazoline Compounds with Ethoxymethylenemalonic Acid Derivatives", J. Heterocyclic Chem., vol. 26, 1989, pp. 161–168.

Zimmermann et al., Phenylamino–Pyrimidine (PAP) Derivatives: A New Class of Potent and Selective Inhibitors of Protein Kinase C (PKC), Arch. Pharm. Pharm. Med. Chem., vol. 329, 1996, pp. 371–376.

*Primary Examiner*—Deepak Rao
(74) *Attorney, Agent, or Firm*—Morgan, Lewis & Bockius LLP

(57) ABSTRACT

A pyrimidine derivative of formula (I):

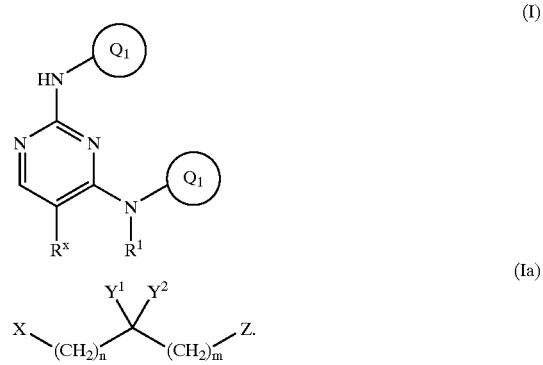

wherein: $R^1$ is an optional substituent as defined within; $R^x$ is selected from halo, hydroxy, nitro, amino, cyano, mercapto, carboxy, sulphamoyl, formamido, ureido or carbamoyl or a group of formula (Ib): A—B—C— as defined within; $Q_1$ and $Q_2$ are independently selected from aryl, a 5- or 6-membered monocyclic moiety; and a 9- or 10-membered bicyclic heterocyclic moiety; and one or both of $Q_1$ and $Q_2$ bears on any available carbon atom one substituent of formula (Ia) as defined within; and $Q_1$ and $Q_2$ are optionally further substituted; or a pharmaceutically acceptable salt or in vivo hydrolysable ester thereof; are useful as anti-cancer agents; and processes for their manufacture and pharmaceutical compositions containing them are described.

13 Claims, No Drawings

FOREIGN PATENT DOCUMENTS

| | | |
|---|---|---|
| WO | WO 95/09852 | 4/1995 |
| WO | WO 95/09853 | 4/1995 |
| WO | WO 95/15952 | 6/1995 |
| WO | WO 96/05177 | 2/1996 |
| WO | WO 96/28427 | 9/1996 |
| WO | WO 96/40143 | 12/1996 |
| WO | WO 97/19065 | 5/1997 |
| WO | WO 97/35856 | 10/1997 |
| WO | WO 97/40017 | 10/1997 |
| WO | WO 97/44326 | 11/1997 |
| WO | WO 97/47618 | 12/1997 |
| WO | WO 98/11095 | 3/1998 |
| WO | WO 98/16230 | 4/1998 |
| WO | WO 98/18782 | 5/1998 |
| WO | WO 98/25619 | 6/1998 |
| WO | WO 98/33798 | 8/1998 |
| WO | WO 98/41512 | 9/1998 |
| WO | WO 98/54093 | 12/1998 |
| WO | WO 98/56788 | 12/1998 |
| WO | WO 99/01136 | 1/1999 |
| WO | WO 99/32121 | 1/1999 |
| WO | WO 99/18096 | 4/1999 |
| WO | WO 99/18942 | 4/1999 |
| WO | WO 99/31073 | 6/1999 |
| WO | WO 99/42153 | 8/1999 |
| WO | WO 99/50250 | 10/1999 |
| WO | WO 00/12485 | 3/2000 |
| WO | WO 00/12486 | 3/2000 |
| WO | WO 00/17202 | 3/2000 |
| WO | WO 00/17203 | 3/2000 |
| WO | WO 00/21926 | 4/2000 |
| WO | WO 00/25780 | 5/2000 |
| WO | WO 00/26209 | 5/2000 |
| WO | WO 00/44750 | 8/2000 |
| WO | WO 00/49018 | 8/2000 |
| WO | WO 00/53595 | 9/2000 |
| WO | WO 00/55161 | 9/2000 |
| WO | WO 00/59892 | 10/2000 |
| WO | WO 00/78731 A1 | 12/2000 |
| WO | WO 01/14375 | 3/2001 |
| WO | WO 01/29009 A1 | 4/2001 |
| WO | WO 01/30778 A1 | 5/2001 |
| WO | WO 01/37835 A1 | 5/2001 |
| WO | WO 01/47897 A1 | 7/2001 |
| WO | WO 01/47921 A1 | 7/2001 |
| WO | WO 01/60816 A1 | 8/2001 |
| WO | WO 01/64653 A1 | 9/2001 |
| WO | WO 01/64654 A1 | 9/2001 |
| WO | WO 01/64655 A1 | 9/2001 |
| WO | WO 01/64656 A1 | 9/2001 |
| WO | WO 01/72717 A1 | 10/2001 |
| WO | WO 02/04429 A1 | 1/2002 |
| WO | WO 02/20512 A1 | 3/2002 |

2,4-DIAMINO PYRIMIDINE COMPOUNDS HAVING ANTI-CELL PROLIFERATIVE ACTIVITY

This application is the National Phase of International Application PCT/GB99/04325 filed Dec. 20, 1999 which designated the U.S. and that International Application was published under PCT Article 21(2) in English.

The invention relates to pyrimidine derivatives, or pharmaceutically acceptable salts or in vivo hydrolysable esters thereof, which possess cell-cycle inhibitory activity and are accordingly useful for their anti-cancer (such as anti-cell-proliferative, anti-cell migration and/or apoptotic) activity and are therefore useful in methods of treatment of the human or animal body. The invention also relates to processes for the manufacture of said pyrimidine derivatives, to pharmaceutical compositions containing them and to their use in the manufacture of medicaments or use in the production of an anti-cancer (anti-cell-proliferation/migration and/or apoptotic) effect in a warm-blooded animal such as man.

A family of intracellular proteins called cyclins play a central role in the cell cycle. The synthesis and degradation of cyclins is tightly controlled such that their level of a expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppresser gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

Furthermore, it is believed that inhibition of focal adhesion kinase (FAK), which is involved in signal transduction pathways, induces apoptosis (cell-death) and/or inhibits cell migration and an inhibitor of FAK may therefore have value as an anti-cancer agent.

The present invention is based on the discovery that certain 2,4-pyrimidine compounds surprisingly inhibit the effects of cell cycle kinases showing selectivity for CDK2, CDK4 and CDK6, and also inhibit FAK and thus possess anti-cancer (anti-cell-migration/proliferation and/or apoptotic) properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to the invention there is provided a pyrimidine derivative of the formula (I):

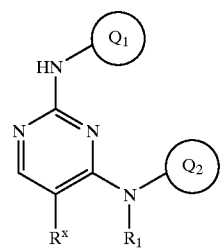

(I)

wherein:

$R^1$ is selected from hydrogen, $C_{1-6}$alkyl [optionally substituted by one or two substituents independently selected from halo, amino, $C_{1-4}$alkylamino, di-($C_{1-4}$alkyl)amino, hydroxy, cyano, $C_{1-4}$alkoxy, $C_{1-4}$alkoxycarbonyl, carbamoyl, —NHCO$C_{1-4}$alkyl, trifluoromethyl, phenylthio, phenoxy, pyridyl, morpholino], benzyl, 2-phenylethyl, $C_{3-5}$alkenyl [optionally substituted by up to three halo substituents, or by one trifluoromethyl substituent, or one phenyl substituent], N-phthalimido-$C_{1-4}$alkyl, $C_{3-5}$alkynyl [optionally substituted by one phenyl substituent] and $C_{3-6}$cycloalkyl-$C_{1-6}$alkyl; wherein any phenyl or benzyl group in $R^1$ is optionally substituted by up to three substituents independently selected from halo, hydroxy, nitro, amino, $C_{1-3}$alkylamino, di-($C_{1-3}$alkyl)amino, cyano, trifluoromethyl, $C_{1-3}$alkyl [optionally substituted by 1 or 2 substituents independently selected from halo, cyano, amino, $C_{1-3}$alkylamino, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, mercapto, $C_{1-3}$alkylthio, carboxy, $C_{1-3}$alkoxycarbonyl;

$R^x$ is selected from halo, hydroxy, nitro, amino, cyano, mercapto, carboxy, sulphamoyl, formamido, ureido or carbamoyl or a group of formula (Ib):

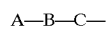

(Ib)

wherein:

A is $C_{1-6}$alkyl, $C_{2-6}$alkenyl, $C_{2-6}$alkynyl, $C_{3-8}$cycloalkyl, phenyl, heterocycle or heteroaryl, wherein said $C_{1-6}$alkyl, $C_{3-6}$alkenyl and $C_{3-6}$alkynyl are optionally substituted by one or more substituents selected from halo, nitro, cyano, amino, hydroxy, mercapto, carboxy, formamido, ureido, $C_{1-3}$alkylamino, di-($C_{1-3}$alkyl)amino, $C_{1-3}$alkoxy, trifluoromethyl, $C_{3-8}$cycloalkyl, phenyl, heterocycle or heteroaryl; wherein any phenyl, $C_{3-8}$cycloalkyl, heterocycle or heteroaryl may be optionally substituted by one or more halo, nitro, cyano, hydroxy, trifluoromethyl, trifluoromethoxy, amino, carboxy, carbamoyl, mercapto, formamido, ureido, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, $C_{1-4}$alkylamino, di-($C_{1-4}$alkyl)amino, $C_{1-4}$alkanoylamino, N—$C_{1-4}$alkylcarbamoyl, N,N-di-($C_{1-4}$alkyl)carbamoyl, $C_{1-4}$alkylthio, $C_{1-4}$alkylsulphinyl, $C_{1-4}$alkylsulphonyl and $C_{1-4}$alkoxycarbonyl;

B is —O—, —S—, —C(O)—, —NH—, —N($C_{1-4}$alkyl)—, —C(O)NH—, —C(O)N($C_{1-4}$alkyl)-, —NHC(O)—, —N($C_{1-4}$alkyl)C(O)— or B is a direct bond;

C is $C_{1-4}$alkylene or a direct bond;

$Q_1$ and $Q_2$ are independently selected from aryl, a 5- or 6-membered monocyclic moiety (linked via a ring carbon atom and containing one to three heteroatoms independently selected from nitrogen, oxygen and sulphur); and a 9- or 10-membered bicyclic heterocyclic moiety (linked via a ring carbon atom and containing one or two nitrogen heteroatoms and optionally containing a further one or two heteroatoms selected from nitrogen, oxygen and sulphur);

and one or both of $Q_1$ and $Q_2$ bears on any available carbon atom one substituent of the formula (Ia) and $Q_2$ may optionally bear on any available carbon atom further substituents of the formula (Ia):

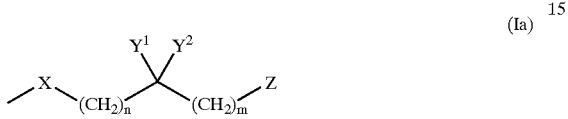
(Ia)

[provided that when present in $Q_1$ the substituent of formula (Ia) is not adjacent to the —NH— link];

wherein:

X is —CH$_2$—, —O—, —NH—, —NR$^y$— or —S— [wherein R$^y$ is $C_{1-4}$alkyl, optionally substituted by one substituent selected from halo, amino, cyano, $C_{1-4}$alkoxy or hydroxy];

$Y^1$ is H, $C_{1-4}$alkyl or as defined for Z;

$Y^2$ is H or $C_{1-4}$alkyl;

Z is R$^a$O—, R$^b$R$^c$N—, R$^d$S—, R$^e$R$^f$NNR$^g$—, a nitrogen linked heteroaryl or a nitrogen linked heterocycle [wherein said heterocycle is optionally substituted on a ring carbon or a ring nitrogen by $C_{1-4}$alkyl or $C_{1-4}$alkanoyl] wherein R$^a$, R$^b$, R$^c$, R$^d$, R$^e$, R$^f$ and R$^g$ are independently selected from hydrogen, $C_{1-4}$alkyl, $C_{2-4}$alkenyl, $C_{3-8}$cycloalkyl, and wherein said $C_{1-4}$alkyl and $C_{2-4}$alkenyl are optionally substituted by one or more phenyl;

n is 1, 2 or 3;

m is 1, 2or 3;

and $Q^1$ may optionally bear on any available carbon atom up to four substituents independently selected from halo, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-3}$alkyl, hydroxy-$C_{1-6}$alkyl, fluoro-$C_{1-4}$alkyl, amino-$C_{1-3}$alkyl, $C_{1-4}$alkylamino-$C_{1-3}$alkyl, di-($C_{1-4}$alkyl)amino-$C_{1-3}$alkyl, cyano-$C_{1-4}$alkyl, $C_{2-4}$alkanoyloxy-$C_{1-4}$alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N—$C_{1-4}$alkylcarbamoyl-$C_{1-4}$alkyl, N,N-di-($C_{1-4}$alkyl)-carbamoyl-$C_{1-4}$alkyl, pyrrolidin-1-yl-$C_{1-3}$alkyl, piperidino-$C_{1-3}$alkyl, piperazin-1-yl-$C_{1-3}$alkyl, morpholino-$C_{1-3}$alkyl, thiomorpholino-$C_{1-3}$alkyl, imidazo-1-yl-$C_{1-3}$alkyl, piperazin-1-yl, morpholino, thiomorpholino, $C_{1-4}$alkylthio, $C_{1-4}$alkylsulphinyl, $C_{1-4}$alkylsulphonyl, hydroxy$C_{2-4}$alkylthio, hydroxy$C_{2-4}$alkylsulphinyl, hydroxy$C_{2-4}$alkylsulphonyl, ureido, N'—($C_{1-4}$alkyl)ureido, N',N'-di-($C_{1-4}$alkyl)ureido, N'—($C_{1-4}$alkyl)-N—($C_{1-4}$alkyl)ureido, N',N'-di-($C_{1-4}$alkyl)-N—($C_{1-4}$alkyl)ureido, carbamoyl, N—($C_{1-4}$alkyl)carbamoyl, N,N-di-($C_{1-4}$alkyl)carbamoyl, amino, $C_{1-4}$alkylamino, di-($C_{1-4}$alkyl)amino, $C_{2-4}$alkanoylamino, sulphamoyl, N—($C_{1-4}$alkyl)sulphamoyl, N,N-di-($C_{1-4}$alkyl)sulphamoyl;

and also independently, or where appropriate in addition to, the above substituents, $Q_1$ may optionally bear on any available carbon atom up to two further substituents independently selected from $C_{3-8}$cycloalkyl, phenyl-$C_{1-4}$alkyl, phenyl-$C_{1-4}$alkoxy, phenylthio, phenyl, naphthyl, benzoyl, benzimidazol-2-yl, phenoxy and a 5- or 6-membered aromatic heterocycle (linked via a ring carbon atom and containing one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-$C_{1-4}$alkyl, phenylthio and phenyl-$C_{1-4}$alkoxy substituents may optionally bear up to five substituents independently selected from halo, $C_{1-4}$alkyl and $C_{1-4}$alkoxy;

and $Q_2$ may optionally bear on any available carbon atom up to four substituents independently selected from halo, hydroxy, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-($C_{1-4}$alkyl)amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N—$C_{1-4}$alkylcarbamoyl-$C_{1-4}$alkyl, N,N-di-($C_{1-4}$alkyl)-carbamoyl-$C_{1-4}$alkyl, pyrrolidin-1-yl-$C_{1-3}$alkyl, piperidino-$C_{1-3}$alkyl, piperazin-1-yl-$C_{1-3}$alkyl, morpholino-$C_{1-3}$alkyl, thiomorpholino-$C_{1-3}$alkyl, imidazo-1-yl-$C_{1-3}$alkyl, piperazin-1-yl, morpholino, thiomorpholino, $C_{1-4}$alkoxy, cyano-$C_{1-4}$alkoxy, carbamoyl-$C_{1-4}$alkoxy, N—$C_{1-4}$alkylcarbamoyl-$C_{1-4}$alkoxy, N,N-di-($C_{1-4}$alkyl)-carbamoyl-$C_{1-4}$alkoxy, 2-aminoethoxy, 2-$C_{1-4}$alkylaminoethoxy, 2-di-($C_{1-4}$alkyl)aminoethoxy, $C_{1-4}$alkoxycarbonyl-$C_{1-4}$alkoxy, halo-$C_{1-4}$alkoxy, 2-hydroxyethoxy, $C_{2-4}$alkanoyloxy-$C_{2-4}$alkoxy, 2-$C_{1-4}$alkoxyethoxy, carboxy-$C_{1-4}$alkoxy, 2-pyrrolidin-1-yl-ethoxy, 2-piperidino-ethoxy, 2-piperazin-1-yl-ethoxy, 2-morpholino-ethoxy, 2-thiomorpholino-ethoxy, 2-imidazo-1-yl-ethoxy, $C_{3-5}$alkenyloxy, $C_{3-5}$alkynyloxy, $C_{1-4}$alkylthio, $C_{1-4}$alkylsulphinyl, $C_{1-4}$alkylsulphonyl, hydroxy$C_{2-4}$alkylthio, hydroxy$C_{2-4}$alkylsulphinyl, hydroxy$C_{2-4}$alkylsulphonyl, ureido, N'—($C_{1-4}$alkyl)ureido, N',N'-di-($C_{1-4}$alkyl)ureido, N'—($C_{1-4}$alkyl)-N—($C_{1-4}$aklyl)ureido, N',N'-di-($C_{1-4}$alkyl)-N—($C_{1-4}$alkyl)ureido, carbamoyl, N—($C_{1-4}$alkyl)carbamoyl, N,N-di-($C_{1-4}$alkyl)carbamoyl, amino, $C_{1-4}$alkylamino, di-($C_{1-4}$alkyl)amino, $C_{2-4}$alkanoylamino, sulphamoyl, N—($C_{1-4}$alkyl)sulphamoyl, N,N-di-($C_{1-4}$alkyl)sulphamoyl, and also independently, or where appropriate in addition to, the above optional substituents, $Q_2$ may optionally bear on any available carbon atom up to two further substituents independently selected from $C_{3-8}$cycloalkyl, phenyl-$C_{1-4}$alkyl, phenyl-$C_{1-4}$alkoxy, phenylthio, phenyl, naphthyl, benzoyl, phenoxy, benzimidazol-2-yl, and a 5- or 6-membered aromatic heterocycle (linked via a ring carbon atom and containing one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-$C_{1-4}$alkyl, phenylthio and phenyl-$C_{1-4}$alkoxy substituents may optionally bear one or two substituents independently selected from halo, $C_{1-4}$alkyl and $C_{1-4}$alkoxy; or a pharmaceutically acceptable salt or in vivo hydrolysable ester thereof.

A suitable value for "heterocycle" within the definition of A in group (Ib) is a fully saturated, mono or bicyclic ring that contains 4–12 atoms, at least one of which is selected from nitrogen, sulphur or oxygen, wherein a —CH$_2$— group can optionally be replaced by a —C(O)—, and a ring sulphur atom may be optionally oxidised to form S-oxide(s). Suitably "heterocycle" is a monocyclic ring containing 5 or 6 atoms or a bicyclic ring containing 9 or 10 atoms. "Heterocycle" may be nitrogen or carbon linked. Suitable values for "heterocycle" include morpholino, piperidyl, piperazinyl, pyrrolidinyl, thiomorpholino, homopiperazinyl, imidazolyl, imidazolidinyl, pyrazolidinyl, dioxanyl and dioxolanyl. Preferably "heterocycle" is morpholine, piperidyl, piperazinyl, pyrrolidinyl, thiomorpholine or homopiperazinyl. More preferably "heterocycle" is morpholino.

A suitable value for "heteroaryl" within the definition of A in group (Ib) is a partially unsaturated or fully unsaturated, mono or bicyclic ring that contains 4–12 atoms, at least one of which is selected from nitrogen, sulphur or oxygen, wherein a —CH$_2$— group can optionally be replaced by a —C(O)—, and a ring sulphur and/or nitrogen atom may be optionally oxidised to form S-oxide(s) and/or an N-oxide. Suitably "heteroaryl" is a monocyclic ring containing 5 or 6 atoms or a bicyclic ring containing 9 or 10 atoms. "Heteroaryl" may be nitrogen or carbon linked (but only nitrogen linked if the nitrogen link results in a neutral compound being formed). Suitable values for "heteroaryl" include thienyl, furyl, imidazolyl, thiazolyl, thiadiazolyl, pyrimidinyl, pyridinyl, pyrazinyl, pyridazinyl, triazinyl, pyrrolyl or pyrazolyl. Preferably "heteroaryl" is furyl, imidazolyl, thiazolyl, isoxazolyl, benzothienyl, quinolinyl, tetrazolyl and pyrazolyl. More preferably "heteroaryl" is imidazol-1-yl, fur-3-yl, isoxazol-3-yl, benzothien-6-yl, quinolin-6-yl, pyrazol-3-yl, thiazol-2-yl or tetrazol-5-yl.

A suitable value for Z in group (Ia) when it is a "nitrogen linked heteroaryl" is a mono or bicyclic ring that has a degree of unsaturation, containing 4–12 atoms, at least one of which is selected from nitrogen, and optionally 1–3 further atoms are selected from nitrogen, sulphur or oxygen, wherein a —CH$_2$— group can optionally be replaced by a —C(O)—, and a ring sulphur and/or nitrogen atom may be optionally oxidised to form S-oxide(s) and/or an N-oxide. Suitably "nitrogen linked heteroaryl" is a monocyclic ring containing 5 or 6 atoms or a bicyclic ring containing 9 or 10 atoms. The nitrogen link results in a neutral compound being formed. Suitable values for "nitrogen linked heteroaryl" include imidazol-1-yl, pyrrolin-1-yl, imidazolin-1-yl, pyrazolin-1-yl, triazol-1-yl, indol-1-yl, isoindol-2-yl, indolin-1-yl, benzimidazol-1-yl, pyrrol-1-yl or pyrazol-1-yl. Preferably "nitrogen linked heteroaryl" is imidazol-1-yl.

A suitable value for Z in group (Ia) when it is a "nitrogen linked heterocycle" is an unsaturated mono or bicyclic ring that contains 4–12 atoms, at least one of which is selected from nitrogen, and optionally 1–3 further atoms are selected from nitrogen, sulphur or oxygen, wherein a —CH$_2$— group can optionally be replaced by a —C(O)—, and a ring sulphur may be optionally oxidised to form S-oxide(s). Suitably "nitrogen linked heterocycle" is a monocyclic ring containing 5 or 6 atoms or a bicyclic ring containing 9 or 10 atoms. Suitable values for "nitrogen linked heterocycle" include pyrrolidin-1-yl, piperidino, piperazin-1-yl, morpholino, thiomorpholino, homopiperidin-y-1 or homopiperazin-1-yl. Preferably a "nitrogen linked heterocycle" is pyrrolidin-1-yl, piperazin-1-yl or morpholino.

A suitable value for $Q_1$ and $Q_2$ when it is a 5- or 6-membered monocyclic moiety containing one to three heteroatoms independently selected from nitrogen, oxygen and sulphur, or a 9- or 10-membered bicyclic heterocyclic moiety containing one or two nitrogen heteroatoms and optionally containing a further one or two heteroatoms selected from nitrogen, oxygen and sulphur; is an aromatic heterocycle, for example, pyrrole, furan, thiophene, imidazole, oxazole, isoxazole, thiazole, pyridyl, pyridazinyl, pyrimidinyl, pyrazinyl, p-isoxazine, quinolyl, isoquinolyl, cinnolinyl, quinazolinyl, quinoxalinyl, phthalazinyl or naphthyridinyl, indole, isoindazole, benzoxazole, benzimidazole, benzothiazole, imidazo[1,5-a]pyridine, imidazo[1,2-c]pyrimidine, imidazo[1,2-a]pyrimidine, imidazo[1,5-a]pyrimidine; or a partially or fully hydrogenated derivative thereof such as for example, 1,2-dihydropyridyl, 1,2-dihydroquinolyl (all linked by a ring carbon atom), provided that an unstable aminal-type link with the amino link to the pyrimidine ring is not present.

When $Q_1$ is a 5- or 6-membered monocyclic moiety containing one to three heteroatoms independently selected from nitrogen, oxygen and sulphur, it will be appreciated that $Q_1$ is linked to the pyrimidine ring in such a way that when $Q_1$ bears a substituent of the formula (Ia) or (Ia') the substituent of formula (Ia) or (Ia') is not adjacent to the —NH— link. Thus, for example, 1,2,3-triazol-4-yl or 1,2,3-triazol-5-yl, are not suitable values for $Q_1$ when $Q_1$ bears a substituent of the formula (Ia) or (Ia'). It will be appreciated that there is at least one substituent of the formula (Ia) or (Ia') in each compound of formula (I), although such a substituent may be borne by $Q_2$ (in which case, when $Q_1$ bears no substituent of formula (Ia) or (Ia'), 1,2,3-triazol-4-yl or 1,2,3-triazol-5-yl, for example, are suitable values for $Q_1$).

When $Q_1$ or $Q_2$ is a 9- or 10-membered bicyclic heterocyclic moiety containing one or two nitrogen atoms it will be appreciated that $Q_1$ or $Q_2$ may be attached from either of the two rings of the bicyclic heterocyclic moiety.

Conveniently when $Q_1$ or $Q_2$ is a 5- or 6-membered monocyclic moiety or a 9- or 10-membered bicyclic heterocyclic moiety it is, for example, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-quinolyl, 3-quinolyl, 5-quinolyl, 6-quinolyl, 7-quinolyl, 1-isoquinolyl, 3-isoquinolyl, 6-isoquinolyl, 7-isoquinolyl, 3-cinnolyl, 6-cinnolyl, 7-cinnolyl, 2-quinazolinyl, 4-quinazolinyl, 6quinazolinyl, 7-quinazolinyl, 2-quinoxalinyl, 5-quinoxalinyl, 6-quinoxalinyl, 1-phthalazinyl, 6-phthalazinyl, 1,5-naphthyridin-2-yl, 1,5-naphthyridin-3-yl, 1,6-naphthyridin-3-yl, 1,6-naphthyridin-7-yl, 1,7-naphthyridin-3-yl, 1,7-naphthyridin-6-yl, 1,8-naphthyridin-3-yl, 2,6-naphthyridin-6-yl or 2,7-naphthyridin-3-yl.

Particularly when $Q_1$ or $Q_2$ is a 5- or 6-membered monocyclic moiety or a 9- or 10-membered bicyclic heterocyclic moiety it is pyridyl, indazolyl, indolyl, quinolyl, pyrazolyl or thiazolyl. More particularly 2-pyridyl, 3-pyridyl, 4-pyridyl, 1H-5-indazolyl, 5-indolyl, 6-quinolyl, 3-pyrazolyl or 2-thiazolyl.

A suitable value for $Q_1$ and $Q_2$ when it is "aryl" is a fully or partially unsaturated, mono or bicyclic carbon ring that contains 4–12 atoms. Suitably "aryl" is a monocyclic ring containing 5 or 6 atoms or a bicyclic ring containing 9 or 10 atoms. Suitable values for "aryl" include phenyl, naphthyl, tetralinyl or indanyl. Particularly "aryl" is phenyl, naphthyl or indanyl. More particularly "aryl" is phenyl or indanyl.

A suitable value for a ring substituent when it is a 5- or 6-membered aromatic heterocycle (linked via a ring carbon atom and containing one to three heteroatoms independently selected from oxygen, sulphur and nitrogen) is, for example, pyrrole, furan, thiophene, imidazole, oxazole, isoxazole, thiazole, pyridyl, pyridazinyl, pyrimidinyl, pyrazinyl or p-isoxazine.

In this specification the term "alkyl" includes both straight and branched chain alkyl groups but references to individual alkyl groups such as "propyl" are specific for the straight chain version only. An analogous convention applies to other generic terms.

Suitable values for the generic radicals (such as in $R^1$ and in substituents on $Q_1$ and $Q_2$ and also those in $R^x$) referred to above include those set out below: when it is halo is, for example, fluoro, chloro, bromo and iodo; $C_{2-4}$alkenyl is, for example, vinyl and allyl; $C_{2-4}$alkenyl is, for example, vinyl and allyl; when it is $C_{3-5}$alkenyl is, for example, allyl; when it is $C_{3-5}$alkynyl is, for example, propyn-2-yl; when it is $C_{2-4}$alkynyl is, for example, ethynyl and propyn-2-yl; $C_{2-6}$alkynyl is, for example, ethynyl and propyn-2-yl; when it is $C_{3-6}$cycloalkyl-$C_{1-6}$alkyl is, for example, cyclopropyl-methyl; when it is $C_{1-5}$alkanoyl is, for example, formyl and acetyl; when it is $C_{1-4}$alkoxycarbonyl is, for example, methoxycarbonyl, ethoxycarbonyl, propoxycarbonyl and tert-butoxycarbonyl; when it is $C_{1-3}$alkyl is, for example, methyl, ethyl, propyl, isopropyl; when it is $C_{1-4}$alkyl is, for example, methyl, ethyl, propyl, isopropyl, butyl, isobutyl, sec-butyl or tert-butyl; when it is $C_{1-6}$alkyl is, for example, methyl, ethyl, propyl, isopropyl, butyl, isobutyl, sec-butyl, tert-butyl or 3-methylbutyl; when it is hydroxy-$C_{1-3}$alkyl is, for example, hydroxymethyl, 1-hydroxyethyl, 2-hydroxyethyl and 3-hydroxypropyl; when it is fluoro-$C_{1-4}$alkyl is, for example, fluoromethyl, difluoromethyl, trifluoromethyl and 2-fluoroethyl; when it is amino-$C_{1-3}$alkyl is, for example, aminomethyl, 1-aminoethyl and 2-aminoethyl; when it is $C_{1-4}$alkylamino-$C_{1-3}$-alkyl is, for example, methylaminomethyl, ethylaminomethyl, 1-methylaminoethyl, 2-methylaminoethyl, 2-ethylamimoethyl and 3-methylaminopropyl; when it is di-($C_{1-4}$alkyl)amino-$C_{1-3}$alkyl is, for example, dimethylaminomethyl, diethylaminomethyl, 1-dimethylaminoethyl, 2-dimethylaminoethyl and 3-dimethylaminopropyl; when it is cyano-$C_{1-4}$alkyl is, for example cyanomethyl, 2-cyanoethyl and 3-cyanopropyl; when it is $C_{2-4}$alkanoyloxy-$C_{1-4}$-alkyl is, for example, acetoxymethyl, propionyloxymethyl, butyryloxymethyl, 2-acetoxyethyl and 3-acetoxypropyl; when it is $C_{1-4}$alkoxy-$C_{1-3}$alkyl is, for example, methoxymethyl, ethoxymethyl, 1-methoxyethyl, 2-methoxyethyl, 2-ethoxyethyl and 3-methoxypropyl; when it is carboxy-$C_{1-4}$alkyl is, for example carboxymethyl, 1-carboxyethyl, 2-carboxyethyl and 3-carboxypropyl; when it is $C_{1-4}$alkoxycarbonyl-$C_{1-4}$alkyl is, for example, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; when it is carbamoyl-$C_{1-4}$alkyl is, for example carbamoylmethyl, 1-carbamoylethyl, 2-carbamoylethyl and 3-carbamoylpropyl; when it is N—$C_{1-4}$alkylcarbamoyl-$C_{1-4}$alkyl is, for example, N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; when it is N,N-di-($C_{1-4}$alkyl)-carbamoyl-$C_{1-4}$alkyl is, for example, N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; when it is pyrrolidin-1-yl-$C_{1-3}$alkyl is, for example, pyrrolidin-1-ylmethyl and 2-pyrrolidin-1-ylethyl; when it is piperidin-1-yl-$C_{1-3}$alkyl is, for example, piperidin-1-ylmethyl and 2-piperidin-1-ylethyl; when it is piperazin-1-yl-$C_{1-3}$alkyl is, for example, piperazin-1-ylmethyl and 2-piperazin-1-ylethyl; when it is morpholino-$C_{1-3}$alkyl is, for example, morpholinomethyl and 2-morpholinoethyl; when it is thiomorpholino-$C_{1-3}$alkyl is, for example, thiomorpholinomethyl and 2-thiomorpholinoethyl; when it is imidazo-1-yl-$C_{1-3}$alkyl is, for example, imidazo-1-ylmethyl and 2-imidazo-1-ylethyl; when it is $C_{1-4}$alkoxy is, for example, methoxy, ethoxy, propoxy, isopropoxy or butoxy; when it is $C_{1-3}$alkoxy is, for example, methoxy, ethoxy, propoxy or isopropoxy; when it is cyano-$C_{1-4}$alkoxy is, for example, cyanomethoxy, 1-cyanoethoxy, 2-cyanoethoxy and 3-cyanopropoxy; when it is carbamoyl-$C_{1-4}$alkoxy is, for example, carbamoylmethoxy, 1-carbamoylethoxy, 2-carbamoylethoxy and 3-carbamoylpropoxy; when it is N—$C_{1-4}$alkylcarbamoyl-$C_{1-4}$alkoxy is, for example, N-methylcarbamoylmethoxy, N-ethylcarbamoylmethoxy, 2-(N-methylcarbamoyl)ethoxy, 2-(N-ethylcarbamoyl)ethoxy and 3-(N-methylcarbamoyl)propoxy; when it is N,N-di-($C_{1-4}$alkyl)-carbamoyl-$C_{1-4}$alkoxy is, for example, N,N-dimethylcarbamoylmethoxy, N-ethyl-N-methylcarbamoylmethoxy, N,N-diethylcarbamoylmethoxy, 2-(N,N-dimethylcarbamoyl)ethoxy, 2-(N,N-diethylcarbamoyl)ethoxy and 3-(N,N-dimethylcarbamoyl)propoxy; when it is 2-$C_{1-4}$alkylaminoethoxy is, for example, 2-(methylamino)ethoxy, 2-(ethylamino)ethoxy and 2-(propylamino)ethoxy; when it is 2-di-($C_{1-4}$alkyl)aminoethoxy is, for example, 2-(dimethylamino)ethoxy, 2-(N-ethyl-N-methylamino)ethoxy, 2-(diethylamino)ethoxy and 2-(dipropylamino)ethoxy; when it is $C_{1-4}$alkoxycarbonyl-$C_{1-4}$alkoxy is, for example, methoxycarbonylmethoxy, ethoxycarbonylmethoxy, 1-methoxycarbonylethoxy, 2-methoxycarbonylethoxy, 2-ethoxycarbonylethoxy and 3-methoxycarbonylpropoxy; when it is halo-$C_{1-4}$alkoxy is, for example, difluoromethoxy, trifluoromethoxy, 2-fluoroethoxy, 2-chloroethoxy, 2-bromoethoxy, 3-fluoropropoxy and 3-chloropropoxy; when it is $C_{2-4}$alkanoyloxy-$C_{2-4}$alkoxy is, for example, 2-acetoxyethoxy, 2-propionyloxyethoxy, 2-butyryloxyethoxy and 3-acetoxypropoxy; when it is 2-$C_{1-4}$alkoxyethoxy is, for example, 2-methoxyethoxy, 2-ethoxyethoxy; when it is carboxy-$C_{1-4}$alkoxy is, for example, carboxymethoxy, 1-carboxyethoxy, 2-carboxyethoxy and 3-carboxypropoxy; when it is $C_{3-5}$alkenyloxy is, for example, allyloxy; when it is $C_{3-5}$alkynyloxy is, for example, propynyloxy; when it is $C_{1-4}$alkylthio is, for example, methylthio, ethylthio or propylthio; when it is $C_{1-4}$alkylthio is $C_{1-3}$alkylthio; when it is $C_{1-4}$alkylsulphinyl is, for example, methylsulphinyl, ethylsulphinyl or propylsulphinyl; when it is $C_{1-4}$alkylsulphonyl is, for example, methylsulphonyl, ethylsulphonyl or propylsulphonyl; when it is N—$C_{1-4}$alkylcarbamoyl is, for example N-methylcarbamoyl, N-ethylcarbamoyl and N-propylcarbamoyl; when it is N,N-di-($C_{1-4}$alkyl)-carbamoyl is, for example N,N-dimethylcarbamoyl, N-ethyl-N-methylcarbamoyl and N,N-diethylcarbamoyl; when it is $C_{1-4}$alkylamino or $C_{1-3}$alkylamino is, for example, methylamino, ethylamino or propylamino; when it is di-($C_{1-4}$ alkyl)amino or di-($C_{1-3}$alkyl)amino is, for example, dimethylamino, N-ethyl-N-methylamino, diethylamino, N-methyl-N-propylamino or dipropylamino; when it is $C_{2-4}$alkanoylamino is, for example, acetamido, propionamido or butyramido; when it is phenyl-$C_{1-4}$alkyl is, for example benzyl or 2-phenylethyl; when it is phenyl-$C_{1-4}$ alkoxy is, for example benzyloxy; when it is —NHCOC$_{1-4}$ alkyl is, for example acetamido; when it is N-phthalimido-$C_{1-4}$alkyl is, for example 2-(N-phthalimido)ethyl or 3-(N-phthalimido)propyl; when it is $C_{3-8}$cycloalkyl is, for example, cyclopropyl, cyclopentyl or cyclohexyl; when it is $C_{1-4}$alkanoyl is, for example, acetyl or propionyl; when it is $C_{1-4}$alkanoyloxy is, for example, acetyloxy or propionyloxy; when it is $C_{1-4}$alkanoylamino is, for example, acetamido; when it is N'—($C_{1-4}$alkyl)ureido is, for example, N'-methylureido or N'-ethylureido; when it is N',N'-di-($C_{1-4}$ alkyl)ureido is, for example, N',N'-dimethylureido, N',N'-diisopropylureido or N'-methyl-N'-propylureido; when it is N'—($C_{1-4}$alkyl)-N—($C_{1-4}$alkyl)ureido is, for example, N'-methyl-N-ethylureido or N'-methyl-N-methylureido; when it is N',N'-di-($C_{1-4}$alkyl)-N—($C_{1-4}$alkyl)ureido is, for example, N',N'-dimethyl-N-ethylureido, N'-methyl-N'-propyl-N-butylureido; when it is N—($C_{1-4}$alkyl)sulphamoyl is, for example, N-methylsulphamoyl or N-isopropylsulphamoyl; when it is N,N-di-($C_{1-4}$alkyl) sulphamoyl is, for example, N-methyl-N-ethylsulphamoyl or N,N-dipropylsulphamoyl.

A suitable pharmaceutically acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereo-isomers and geometric isomers that possess CDK and/or FAK inhibitory activity.

The invention relates to any and all tautomeric forms of the compounds of the formula (I) that possess CDK and/or FAK inhibitory activity.

It is also to be understood that certain compounds of the formula (I) can exist in solvated as well as unsolvated forms such as, for example, hydrated forms. It is to be understood that the invention encompasses all such solvated forms which possess CDK and/or FAK inhibitory activity.

According to a further feature of the invention there is provided a pyrimidine derivative of the formula (I) (as depicted above) wherein:

$R^1$ is selected from hydrogen, $C_{1-6}$alkyl [optionally substituted by one or two substituents independently selected from halo, amino, $C_{1-4}$alkylamino, di-($C_{1-4}$ alkyl)amino, hydroxy, cyano, $C_{1-4}$alkoxy, $C_{1-4}$alkoxycarbonyl, carbamoyl, —NHCOC$_{1-4}$alkyl, trifluoromethyl, phenylthio, phenoxy], benzyl, $C_{3-5}$alkenyl [optionally substituted by up to three halo substituents, or by one trifluoromethyl substituent, or one phenyl substituent], N-phthalimido-$C_{1-4}$alkyl, $C_{3-5}$alkynyl and $C_{3-6}$cycloalkyl-$C_{1-6}$alkyl; wherein any phenyl or benzyl group in $R^1$ is optionally substituted by up to three substituents independently selected from halo, hydroxy, nitro, amino, $C_{1-3}$alkylamino, di-($C_{1-3}$ alkyl)amino, cyano, trifluoromethyl, $C_{1-3}$alkyl [optionally substituted by 1 or 2 substituents independently selected from halo, cyano, amino, $C_{1-3}$alkylamino, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-3}$alkyl, carboxy, $C_{1-3}$alkoxycarbonyl;

$R^1$ is selected from halo, hydroxy, nitro, amino, $C_{1-3}$alkylamino, di-($C_{1-3}$alkyl)amino, cyano, trifluoromethyl, $C_{1-3}$alkyl [optionally substituted by 1 or 2 substituents independently selected from halo, cyano, amino, $C_{1-3}$alkylamino, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-3}$alkyl, carboxy, $C_{1-3}$alkoxycarbonyl;

$Q_1$ and $Q_2$ are independently selected from phenyl, naphthyl, a 5- or 6-membered monocyclic moiety (linked via a ring carbon atom and containing one to three heteroatoms independently selected from nitrogen, oxygen and sulphur); and a 9- or 10-membered bicyclic heterocyclic moiety (linked via a ring carbon atom and containing one or two nitrogen heteroatoms and optionally containing a further one or two heteroatoms selected from nitrogen, oxygen and sulphur); provided that when a substituent of formula (Ia') (defined hereinbelow) is present in $Q_1$ there is an available carbon atom in $Q_1$ such that the substituent of formula (Ia') is not adjacent to the —NH— link);

and one or both of $Q_1$ and $Q_2$ bears on any available carbon atom one substituent of the formula (Ia') and $Q_2$ may bear on any available carbon atom further substituents of the formula (Ia')

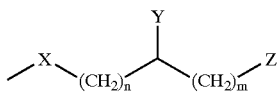
(Ia')

[provided that when present in $Q_1$ the substituent of formula (Ia') is not adjacent to the —NH— link];
wherein:
X is $CH_2$, O, NH or S;
Y is H or as defined for Z;
Z is OH, SH, $NH_2$, $C_{1-4}$alkoxy, $C_{1-4}$alkylthio, —NH$C_{1-4}$alkyl, —N($C_{1-4}$alkyl)$_2$, pyrrolidin-1-yl, piperidin-1-yl, piperazin-1-yl, morpholino or thiomorpholino;
n is 1, 2 or 3;
m is 1, 2 or 3;
and $Q_1$ may optionally bear on any available carbon atom up to four substituents independently selected from halo, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-($C_{1-4}$alkyl)amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N—$C_{1-4}$alkylcarbamoyl-$C_{1-4}$alkyl, N,N-di-($C_{1-4}$alkyl)-carbamoyl-$C_{1-4}$alkyl, pyrrolidin-1-yl-$C_{1-3}$alkyl, piperidin-1-yl-$C_{1-3}$alkyl, piperazin-1-yl-$C_{1-3}$alkyl, morpholino-$C_{1-3}$alkyl, thiomorpholino-$C_{1-3}$alkyl, piperazin-1-yl, morpholino, thiomorpholino, $C_{1-4}$alkylthio, $C_{1-4}$alkylsulphinyl, $C_{1-4}$alkylsulphonyl, ureido ($H_2$N—CO—NH—), $C_{1-4}$alkylNH—CO—NH—, di-($C_{1-4}$alkyl)N—CO—NH—, $C_{1-4}$alkylNH—CO—N($C_{1-4}$alkyl)-, di-($C_{1-4}$alkyl)N—CO—N($C_{1-4}$alkyl)-, carbamoyl, N—($C_{1-4}$alkyl)carbamoyl, N,N-di-($C_{1-4}$alkyl)carbamoyl, amino, $C_{1-4}$alkylamino, di-($C_{1-4}$alkyl)amino, $C_{2-4}$alkanoylamino;
and also independently, or in addition to, the above substituents, $Q_1$ may optionally bear on any available carbon atom up to two further substituents independently selected from phenyl-$C_{1-4}$alkyl, phenyl-$C_{1-4}$alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-$C_{1-4}$alkyl and phenyl-$C_{1-4}$alkoxy substituents may optionally bear one or two substituents independently selected from halo, $C_{1-4}$alkyl and $C_{1-4}$alkoxy;
and $Q_2$ may optionally bear on any available carbon atom up to four substituents independently selected from halo, hydroxy, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-($C_{1-4}$alkyl)amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N—$C_{1-4}$alkylcarbamoyl-$C_{1-4}$alkyl, N,N-di-($C_{1-4}$alkyl)-carbamoyl-$C_{1-4}$alkyl, pyrrolidin-1-yl-$C_{1-3}$alkyl, piperidin-1-yl-$C_{1-3}$alkyl, piperazin-1-yl-$C_{1-3}$alkyl, morpholino-$C_{1-3}$alkyl, thiomorpholino-$C_{1-3}$alkyl, piperazin-1-yl, morpholino, thiomorpholino, $C_{1-4}$alkoxy, cyano-$C_{1-4}$alkoxy, carbamoyl-$C_{1-4}$alkoxy, N—$C_{1-4}$alkylcarbamoyl-$C_{1-4}$alkoxy, N,N-di-($C_{1-4}$alkyl)-carbamoyl-$C_{1-4}$alkoxy, 2-aminoethoxy, 2-$C_{1-4}$alkylaminoethoxy, 2-di-($C_{1-4}$alkyl)aminoethoxy, $C_{1-4}$alkoxycarbonyl-$C_{1-4}$alkoxy, halo-$C_{1-4}$alkoxy, 2-hydroxyethoxy, $C_{2-4}$alkanoyloxy-$C_{2-4}$alkoxy, 2-$C_{1-4}$alkoxyethoxy, carboxy-$C_{1-4}$alkoxy, $C_{3-5}$alkenyloxy, $C_{3-5}$alkynyloxy, $C_{1-4}$alkylthio, $C_{1-4}$alkylsulphinyl, $C_{1-4}$alkylsulphonyl, ureido ($H_2$N—CO—NH—), $C_{1-4}$alkylNH—CO—NH—, di-($C_{1-4}$alkyl)N—CO—NH—, $C_{1-4}$alkylNH—CO—N($C_{1-4}$alkyl)-, di-($C_{1-4}$alkyl)N—CO—N($C_{1-4}$alkyl)-, carbamoyl, N—($C_{1-4}$alkyl)carbamoyl, N,N-di-($C_{1-4}$alkyl)carbamoyl, amino, $C_{1-4}$alkylamino, di-($C_{1-4}$alkyl)amino, $C_{2-4}$alkanoylamino,
and also independently, or in addition to, the above substituents, $Q_2$ may optionally bear on any available carbon atom up to two further substituents independently selected from phenyl-$C_{1-4}$alkyl, phenyl-$C_{1-4}$alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-$C_{1-4}$alkyl and phenyl-$C_{1-4}$alkoxy substituents may optionally bear one or two substituents independently selected from halo, $C_{1-4}$alkyl and $C_{1-4}$alkoxy; or a pharmaceutically acceptable salt or in vivo hydrolysable ester thereof.

Particular preferred compounds of the invention comprise a pyrimidine derivative of the formula (I), or pharmaceutically acceptable salt or in vivo hydrolysable ester thereof, wherein $R^1$, $R^x$, $Q_1$, $Q_2$, X, Y, Z, m and n have any of the meanings defined hereinbefore, or any of the following values. Such values may be used where appropriate with any of the definitions, claims or embodiments defined hereinbefore or hereinafter:

(1) $Q_1$ and $Q_2$ are selected from phenyl, pyridyl, indanyl, indazolyl, indolyl, quinolyl, pyrazolyl or thiazolyl;

(2) $Q_1$ and $Q_2$ are both phenyl or both pyridyl or $Q_1$ is phenyl and $Q_2$ is indanyl, pyridyl, indazolyl, indolyl, quinolyl, pyrazolyl or thiazolyl or $Q_1$ is pyridyl and $Q_2$ is phenyl;

(3) $Q_1$ and $Q_2$ are both phenyl or $Q_1$ is 3-pyridyl and $Q_2$ is 2-pyridyl or $Q_1$ is phenyl and $Q_2$ is 5-indanyl, 2-pyridyl, 3-pyridyl, 4-pyridyl, 1H-5-indazolyl, 5-indolyl, 6-quinolyl, 3-pyrazolyl or 2-thiazolyl or $Q_1$ is 3-pyridyl and $Q_2$ is phenyl;

(4) $Q_1$ and $Q_2$ are both phenyl or $Q_1$ is phenyl and $Q_2$ is indanyl, pyridyl or thiazolyl;

(5) $Q_1$ and $Q_2$ are both phenyl or $Q_1$ is phenyl and $Q_2$ is pyridyl;

(6) $Q_1$ and $Q_2$ are both phenyl or $Q_1$ is phenyl and $Q_2$ is indanyl, pyridyl or indazolyl;

(7) $Q_1$ and $Q_2$ are preferably both phenyl;

(8) $Q_1$ and $Q_2$ are selected from phenyl and pyridyl.

(9) $Q_1$ and $Q_2$ are selected from pyridyl.

(10) $R^1$ is preferably hydrogen, benzyl, $C_{3-5}$alkynyl (especially propyn-2-yl), $C_{3-6}$cycloalkyl-$C_{1-6}$alkyl (especially cyclopropylmethyl), $C_{1-4}$alkyl [optionally substituted by one substituent selected from hydroxy, amino, halo, trifluoromethyl and cyano] or $C_{3-5}$alkenyl substituted by one to three halo groups;

(11) In another embodiment $R^1$ is hydrogen;

(12) $R^1$ is preferably benzyl, $C_{3-5}$alkynyl (especially propyn-2-yl), $C_{3-6}$cycloalkyl-$C_{1-6}$alkyl (especially cyclopropylmethyl), $C_{1-4}$alkyl [optionally substituted by one substituent selected from hydroxy, amino, halo, trifluoromethyl and cyano] or $C_{3-5}$alkenyl substituted by one halo group;

(13) $R^1$ is more preferably $C_{3-5}$alkynyl (especially propyn-2-yl) or $C_{1-4}$alkyl [optionally substituted by trifluoromethyl or cyano] or $C_{3-5}$alkenyl substituted by one bromo group;

(14) $R^1$ is most preferably propyn-2-yl, $C_{1-4}$alkyl substituted by one trifluoromethyl or one cyano group (especially cyanomethyl or 2-cyanoethyl) or $C_{3-5}$alkenyl substituted by one bromo group (especially —$CH_2CH=CHBr$);

(15) $R^1$ is most especially preferred as propyn-2-yl, cyanomethyl, 2-cyanoethyl, —$CH_2CH=CHBr$ or —$CH_2CH_2CH_2CF_3$ (especially —$CH_2CH_2CH_2CF_3$);

(16) $R^1$ is hydrogen, methyl, —$CH_2CH_2CH_2CF_3$, —$CH_2CH=CHBr$, —$CH_2CH=CHPh$;

(17) $R^1$ is hydrogen or —$CH_2CH_2CH_2CF_3$;

(18) $R^x$ is preferably selected from halo, hydroxy, nitro, amino, $C_{1-3}$alkylamino, di-($C_{1-3}$alkyl)amino, cyano, trifluoromethyl, $C_{1-3}$alkyl [optionally substituted by 1 or 2 substituents independently selected from halo, cyano, amino, $C_{1-3}$alkylamino, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH and —S—$C_{1-3}$alkyl;

(19) $R^x$ is more preferably selected from halo (especially bromo), nitro and $C_{1-3}$alkyl (especially methyl);

(20) $R^x$ is selected from halo, hydroxy, nitro, amino, $C_{1-3}$alkylamino, di-($C_{1-3}$alkyl)amino, cyano, trifluoromethyl, $C_{1-3}$alkyl [optionally substituted by 1 or 2 substituents independently selected from halo, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-3}$alkyl, carboxy, $C_{1-3}$alkoxycarbonyl;

(21) $R^x$ is selected from halo, hydroxy, nitro, amino, cyano, mercapto, carboxy, sulphamoyl, formamido, ureido or carbamoyl or a group of formula (Ib):

A—B—C—           (Ib)

wherein:
A is $C_{1-6}$alkyl, $C_{2-6}$alkenyl, $C_{2-6}$alkynyl, $C_{3-8}$cycloalkyl, phenyl, heterocycle or heteroaryl, wherein said $C_{1-6}$alkyl, $C_{3-6}$alkenyl and $C_{3-6}$alkynyl are optionally substituted by one or more substituents selected from halo, nitro, mercapto, formamido, ureido, di-($C_{1-3}$alkyl)amino, trifluoromethyl, $C_{3-8}$cycloalkyl, phenyl, heterocycle or heteroaryl; wherein any phenyl, $C_{3-8}$cycloalkyl, heterocycle or heteroaryl may be optionally substituted by one or more halo, nitro, cyano, hydroxy, trifluoromethyl, trifluoromethoxy, amino, carboxy, carbamoyl, mercapto, formamido, ureido, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, $C_{1-4}$alkylamino, di-($C_{1-4}$alkyl)amino, $C_{1-4}$alkanoylamino, N—$C_{1-4}$alkylcarbamoyl, N,N-di-($C_{1-4}$alkyl)carbamoyl, $C_{1-4}$alkylthio, $C_{1-4}$alkylsulphinyl, $C_{1-4}$alkylsulphonyl and $C_{1-4}$alkoxycarbonyl;

B is —O—, —S—, —NH—, —N($C_{1-4}$alkyl)-, —C(O)NH—, —C(O)N($C_{1-4}$alkyl)-, —N($C_{1-4}$alkyl)C(O)— or B is a direct bond;

C is $C_{1-4}$alkylene or a direct bond;

(22) $R^x$ is selected from halo, hydroxy, nitro, amino, $C_{1-3}$alkylamino, di-($C_{1-3}$alkyl)amino, cyano, trifluoromethyl, $C_{1-3}$alkyl [optionally substituted by 1 or 2 substituents independently selected from halo, cyano, amino, $C_{1-3}$alkylamino, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, —SH, —S—$C_{1-3}$alkyl, carboxy;

(23) $R^x$ is selected from halo, nitro, amino, cyano or carboxy or a group of formula (Ib) (as depicted above) wherein A is $C_{1-6}$alkyl, $C_{2-6}$alkenyl, $C_{3-8}$cycloalkyl, phenyl, heterocycle or heteroaryl, wherein said $C_{1-6}$alkyl and $C_{3-6}$alkenyl are optionally substituted by one or more substituents selected formamido, ureido, $C_{1-3}$alkylamino, di-($C_{1-3}$alkyl)amino, hydroxy, phenyl, $C_{3-8}$cycloalkyl, or heteroaryl; wherein any phenyl, $C_{3-8}$cycloalkyl, heterocycle or heteroaryl may be optionally substituted by one or more halo and $C_{1-4}$alkyl; B is —O—, —S—, —C(O)—, —NH—, —C(O)NH— or —NHC(O)— or B is a direct bond; C is $C_{1-4}$alkyl or a direct bond;

(24) $R^x$ is selected from fluoro, chloro, bromo, nitro, amino, cyano or carboxy or a group of formula (Ib) (as depicted above) wherein A is methyl, isopropyl, propyl, ethyl, butyl, vinyl, allyl, cyclohexyl, phenyl, morpholino, imidazolyl, isoxazolyl, quinolinyl, benzothienyl, pyrazolyl, thiazolyl, tetrazolyl or furyl, wherein said methyl, isopropyl, propyl, ethyl, butyl, vinyl, allyl, are optionally substituted by one or more substituents selected formamido, ureido, methylamine, dimethylamino, diethylamino, hydroxy, phenyl, cyclopentyl, or heteroaryl; wherein any phenyl or isoxazolyl may be optionally substituted by one or more fluoro or methyl; B is —O—, —S—, —C(O)—, —NH—, —C(O)NH— or —NHC(O)— or B is a direct bond; C is methylene or a direct bond;

(25) $R^x$ is selected from fluoro, chloro, bromo, nitro, amino, cyano, carboxy, methyl, methoxy, ethoxy, ethoxymethyl, vinyl, allyloxymethyl, hydroxymethyl, 2-hydroxyethoxymethyl, 4-hydroxybutoxymethyl, dimethylaminomethyl, diethylaminomethyl, ureidomethyl, formamidomethyl, methylaminomethyl, isopropylaminocarbonyl, phenyl, benzyl, phenethyl, benzoylamino, 4-phenylbutyryl, 2-phenylvinyl (optionally substituted by fluoro), benzyloxymethyl, cyclohexyloxymethyl, 3-cyclopentylpropionyl, morpholino, furyl, imidazolylmethyl, isoxazolyloxymethyl (optionally substituted by methyl), quinolinylaminomethyl, benzothienylaminomethyl, pyrazolylaminomethyl, isoxazolylaminomethyl, thiazolylthiomethyl and tetrazolylthiomethyl;

(26) $R^x$ is selected from chloro, bromo, nitro, cyano and tetrazolylthiomethyl;

(27) $R^x$ is selected from fluoro, chloro, bromo and cyano;
(28) $R^x$ is bromo;
(29) Preferably in the substituent of formula (Ia') X is O, Y is OH and Z is —N($C_{1-4}$alkyl)$_2$; preferably n is 1 and m is 1;
(30) In the substituent of formula (Ia) X is —O—, $Y^1$ is OH, $Y^2$ is H and Z is —N($C_{1-4}$alkyl)$_2$; n is 1 and m is 1;
(31) Most preferably the substituent of formula (Ia') is 3-dimethylamino-2-hydroxypropoxy;
(32) Preferably there is one substituent of formula (Ia'), and this substituent is in ring $Q_1$ (i.e. a ring linked via —NH—);
(33) When $Q_1$ is phenyl the substituent of formula (Ia') must be in either the para- or meta-position relative to the —NH—, preferably in the para-position;
(34) In the substituent of formula (Ia) X is —O—, —NH—, —NR$^y$— [wherein R$^y$ is $C_{1-4}$alky], $Y^1$ is H, $C_{1-4}$alkyl or hydroxy, $Y^2$ is H or $C_{1-4}$alkyl, Z is R$^a$O—, R$^b$R$^c$N—, R$^e$R$^f$NNR$^g$—, a nitrogen linked heteroaryl or a nitrogen linked heterocycle [wherein said heterocycle is optionally substituted on a ring carbon or a ring nitrogen by $C_{1-4}$alkyl or $C_{1-4}$alkanoyl] wherein R$^a$, R$^b$, R$^c$, R$^e$, R$^f$ and R$^g$ are independently selected from hydrogen, $C_{1-4}$alkyl, $C_{2-4}$alkenyl, $C_{3-8}$cycloalkyl, and wherein said $C_{1-4}$alkyl are optionally substituted by one or more phenyl, n is 1 and m is 1;
(35) In the substituent of formula (Ia) X is —O—, —NH—, —NMe—, $Y^1$ is H, methyl or hydroxy, $Y^2$ is H or methyl, Z is R$^a$O—, R$^b$R$^c$N—, R$^e$R$^f$NNR$^g$—, imidazol-1-yl, morpholino, pyrrolidin-1-yl or piperazin-1-yl [wherein piperazin-1-yl is optionally substituted on a ring carbon or a ring nitrogen by methyl or acetyl] wherein R$^a$, R$^b$, R$^c$, R$^e$, R$^f$ and R$^g$ are independently selected from hydrogen, methyl, ethyl, isopropyl, isobutyl, tert-butyl, allyl, cyclopentyl, benzyl, n is 1 and m is 1;
(36) The substituent of formula (Ia) is 3-amino-2-hydroxypropoxy, 3-methylamino-2-hydroxypropoxy, 3-dimethylaminopropoxy, 3-dimethylamino-2-hydroxypropoxy, 3-ethylamino-2-hydroxypropoxy, 3-diethylaminopropoxy, 3-isopropylaminopropoxy, 3-isopropylamino-2-hydroxypropoxy, 3-isopropylamino-2-hydroxy-2-methylpropoxy, 3-isobutylamino-2-hydroxypropoxy, 3-t-butylamino-2-hydroxypropoxy, 3-ethoxy-2-hydroxypropoxy, 3-(N-isopropyl-N-benzylamino)-2-hydroxypropoxy, 3-(N-allyl-N-methylamino)-2-hydroxypropoxy, 3-(4-methylpiperazin-1-yl)propoxy, 3-(4-methylpiperazin-1-yl)-2-hydroxypropoxy, 3-(4-acetylpiperazin-1-yl)-2-hydroxypropoxy, 3-morpholinopropoxy, 3-morpholino-2-hydroxypropoxy, 3-cyclopentylamino-2-hydroxypropoxy, 3-pyrrolidin-1-yl-2-hydroxypropoxy, 3-imidazol-1-ylpropoxy, 3-(N'N'-dimethylhydrazino)-2-hydroxypropoxy, 3-N',N'-dimethylaminopropylamino, 3-N', N'-dimethylamino-2,2-dimethylpropylamino, 3-N',N'-dimethylamino-2-hydroxy-N-methylpropylamino, 3-N'-isopropylaminopropylamino or 3-imidazol-1-ylpropylamino;
(37) The substituent of formula (Ia) is 3-amino-2-hydroxypropoxy, 3-dimethylaminopropoxy, 3-dimethylamino-2-hydroxypropoxy, 3-isopropylaminopropoxy, 3-isopropylamino-2-hydroxypropoxy, 3-isopropylamino-2-hydroxy-2-methylpropoxy, 3-isobutylamino-2-hydroxypropoxy, 3-t-butylamino-2-hydroxypropoxy, 3-cyclopentylamino-2-hydroxypropoxy, 3-N',N'-dimethylaminopropylamino, 3-N'-isopropylaminopropylamino or 3-imidazol-1-ylpropylamino;
(38) The substituent of formula (Ia) is 3-dimethylamino-2-hydroxypropoxy, 3-isopropylaminopropoxy, 3-isopropylamino-2-hydroxypropoxy, 3-isopropylamino-2-hydroxy-2-methylpropoxy or 3-imidazol-1-ylpropylamino;
(39) The substituent of formula (Ia) is 3-dimethylaminopropoxy, 3-dimethylamino-2-hydroxypropoxy, 3-diethylaminopropoxy or 3-isopropylamino-2-hydroxypropoxy;
(40) Preferable further substituents for $Q_2$ include halo, hydroxy-$C_{1-3}$alkyl, fluoro-$C_{1-4}$alkyl (especially trifluoromethyl), morpholino and $C_{1-4}$alkyl (especially methyl);
(41) More preferable further substituents for $Q_2$ include halo, morpholino and $C_{1-4}$alkyl (especially methyl);
(42) Further substituents for $Q_2$ include halo, hydroxy, cyano, $C_{1-6}$alkyl, hydroxy-$C_{1-3}$alkyl, fluoro-$C_{1-4}$alkyl, $C_{1-4}$alkoxy-$C_{1-3}$alkyl, morpholino, $C_{1-4}$alkoxy, 2-morpholino-ethoxy, 2-imidazo-1-yl-ethoxy, $C_{1-4}$alkylthio, carbamoyl, amino, $C_{2-4}$alkanoylamino, sulphamoyl, phenyl-$C_{1-4}$alkyl, phenyl-$C_{1-4}$alkoxy, phenyl and phenoxy;
(43) Further substituents for $Q_2$ include fluoro, chloro, bromo, hydroxy, cyano, methyl, hydroxymethyl, hydroxyethyl, trifluoromethyl, butoxymethyl, morpholino, methoxy, butoxy, 2-morpholinoethoxy, 2-imidazo-1-ylethoxy, methylthio, carbamoyl, amino, acetylamino, sulphamoyl, benzyl, benzyloxy, phenyl and phenoxy;
(44) A further substituent for $Q_2$ is methyl;
(45) $Q_2$ is unsubstituted or substituted by methyl;
(46) Further substituents for $Q_2$ include fluoro, chloro, bromo, cyano, methyl, hydroxymethyl, methoxy;
(47) Further substituents for $Q_2$ include fluoro, bromo, methyl, hydroxymethyl, methoxy, 2-imidazo-1-ylethoxy and phenyl;
(48) A further substituent for $Q_2$ is chloro.
(49) $Q_2$ is unsubstituted or substituted by chloro;
(50) Preferably the ring $Q_1$ or $Q_2$ not bearing the substituent of formula (Ia') is substituted by one or two further substituents, preferably halo, morpholino and/or $C_{1-4}$alkyl (especially methyl);
(51) Most preferably the ring $Q_1$ bears the substituent of formula (Ia') and $Q_2$ is substituted by one or two further substituents, selected preferably from halo, hydroxy-$C_{1-3}$alkyl, fluoro-$C_{1-4}$alkyl (especially trifluoromethyl), morpholino and $C_{1-4}$alkyl (especially methyl);
(52) A further substituent for $Q_1$ is halo;
(53) A further substituent for $Q_1$ is fluoro;
(54) $Q_1$ is unsubstituted except for a substituent of formula (Ia) or (Ia').

A preferred compound of the invention is a pyrimidine derivative of the formula (I), or pharmaceutically acceptable salt or in vivo hydrolysable ester thereof, wherein:

$Q_1$ and $Q_2$ are both phenyl;

$R^x$ is bromo, nitro or methyl (especially bromo or nitro);

$R^1$ is $C_{1-4}$alkyl substituted by one cyano group (especially cyanomethyl);

or alternatively $R^1$ —$CH_2CH$=$CHBr$ or —$CH_2CH_2CH_2CF_3$ (especially —$CH_2CH_2CH_2CF_3$);

$Q_1$ bears one substituent of formula (Ia') (especially 3-dimethylamino-2-hydroxypropoxy), preferably in the para-position; and $Q_2$ bears one or two substituents independently selected from halo, morpholino and $C_{1-4}$alkyl (especially methyl).

In one aspect of the invention, a preferred compound of the invention is a pyrimidine derivative of the formula (I), or pharmaceutically acceptable salt or in vivo hydrolysable ester thereof, wherein:

$Q_1$ and $Q_2$ are both phenyl or both pyridyl or $Q_1$ is phenyl and $Q_2$ is indanyl, pyridyl, indazolyl, indolyl, quinolyl, pyrazolyl or thiazolyl or $Q_1$ is pyridyl and $Q_2$ is phenyl;

$R^1$ is hydrogen, methyl, —$CH_2CH_2CH_2CF_3$, —$CH_2CH$=$CHBr$ or —$CH_2CH$=$CHPh$;

$R^x$ is fluoro, chloro, bromo, nitro, amino, cyano, carboxy, methyl, methoxy, ethoxy, ethoxymethyl, vinyl, allyloxymethyl, hydroxymethyl, 2-hydroxyethoxymethyl, 4-hydroxybutoxymethyl, dimethylaminomethyl, diethylaminomethyl, ureidomethyl, formamidomethyl, methylaminomethyl, isopropylaminocarbonyl, phenyl, benzyl, phenethyl, benzoylamino, 4-phenylbutyryl, 2-phenylvinyl (optionally substituted by fluoro), benzyloxymethyl, cyclohexyloxymethyl, 3-cyclopentylpropionyl, morpholino, furyl, imidazolylmethyl, isoxazolyloxymethyl (optionally substituted by methyl), quinolinylaminomethyl, benzothienylaminomethyl, pyrazolylaminomethyl, isoxazolylaminomethyl, thiazolylthiomethyl or tetrazolylthiomethyl;

$Q_1$ is optionally substituted by fluoro and is substituted by a group of formula (Ia) which is 3-amino-2-hydroxypropoxy, 3-methylamino-2-hydroxypropoxy, 3-dimethylaminopropoxy, 3-dimethylamino-2-hydroxypropoxy, 3-ethylamino-2-hydroxypropoxy, 3-diethylaminopropoxy, 3-isopropylaminopropoxy, 3-isopropylamino-2-hydroxypropoxy, 3-isopropylamino-2-hydroxy-2-methylpropoxy, 3-isobutylamino-2-hydroxypropoxy, 3-t-butylamino-2-hydroxypropoxy, 3-ethoxy-2-hydroxypropoxy, 3-(N-isopropyl-N-benzylamino)-2-hydroxypropoxy, 3-(N-allyl-N-methylamino)-2-hydroxypropoxy, 3-(4-methylpiperazin-1-yl)propoxy, 3-(4-methylpiperazin-1-yl)-2-hydroxypropoxy, 3-(4-acetylpiperazin-1-yl)-2-hydroxypropoxy, 3-morpholinopropoxy, 3-morpholino-2-hydroxypropoxy, 3-cyclopentylamino-2-hydroxypropoxy, 3-pyrrolidin-1-yl-2-hydroxypropoxy, 3-imidazol-1-ylpropoxy, 3-(N',N'-dimethylhydrazino)-2-hydroxypropoxy, 3-N',N'-dimethylaminopropylamino, 3-N',N'-dimethylamino-2,2-dimethylpropylamino, 3-N',N'-dimethylamino-2-hydroxy-N-methylpropylamino, 3-N'-isopropylaminopropylamino or 3-imidazol-1-ylpropylamino; and $Q_2$ is optionally substituted by one or two halo, hydroxy, cyano, $C_{1-6}$alkyl, hydroxy-$C_{1-3}$alkyl, fluoro-$C_{1-4}$alkyl, $C_{1-4}$alkoxy-$C_{1-3}$alkyl, morpholino, $C_{1-4}$alkoxy, 2-morpholino-ethoxy, 2-imidazo-1-yl-ethoxy, $C_{1-4}$alkylthio, carbamoyl, amino, $C_{2-4}$alkanoylamino, sulphamoyl, phenyl-$C_{1-4}$alkyl, phenyl-$C_{1-4}$alkoxy, phenyl and phenoxy.

In another aspect of the invention, a preferred compound of the invention is a pyrimidine derivative of the formula (I), or pharmaceutically acceptable salt or in vivo hydrolysable ester thereof, wherein:

$Q_1$ and $Q_2$ are both phenyl or $Q_1$ is phenyl and $Q_2$ is indanyl, pyridyl or thiazolyl;

$R^1$ is hydrogen;

$R^x$ is selected from chloro, bromo, nitro, cyano and tetrazolylthiomethyl;

$Q_1$ is substituted by a group of formula (Ia) which is 3-dimethylamino-2-hydroxypropoxy, 3-isopropylaminopropoxy, 3-isopropylamino-2-hydroxypropoxy, 3-isopropylamino-2-hydroxy-2-methylpropoxy or 3-imidazol-1-ylpropylamino; and $Q_2$ is optionally substituted by one or two fluoro, bromo, methyl, hydroxymethyl, methoxy, 2-imidazo-1-ylethoxy and phenyl.

In another aspect of the invention, a preferred compound of the invention is a pyrimidine derivative of the formula (I), or pharmaceutically acceptable salt or in vivo hydrolysable ester thereof, wherein:

$Q_1$ and $Q_2$ are both phenyl or $Q_1$ is phenyl and $Q_2$ is indanyl, pyridyl or indazolyl;

$R^1$ is hydrogen or —$CH_2CH_2CH_2CF_3$;

$R^x$ is selected from fluoro, chloro, bromo and cyano;

$Q_1$ is substituted by a group of formula (Ia) which is 3-dimethylaminopropoxy, 3-dimethylamino-2-hydroxypropoxy, 3-diethylaminopropoxy or 3-isopropylamino-2-hydroxypropoxy; and $Q_2$ is optionally substituted by one or two fluoro, bromo, methyl, hydroxymethyl, methoxy, 2-imidazo-1-ylethoxy and phenyl.

A specific preferred compound of the invention is the following pyrimidine derivative of the formula (I):

2-{4-[3-(N,N-Dimethyl)amino-2-hydroxy-propoxy]anilino}-4-(4-bromoanilino)-5-bromo-pyrimidine;

2-{4-[3-(N,N-Dimethyl)amino-2-hydroxy-propoxy]anilino}-4-(2-fluoro-5-methylanilino)-5-bromo-pyrimidine;

or pharmaceutically acceptable salt or in vivo hydrolysable ester thereof.

In one aspect of the invention preferred compounds of the invention are those of Examples 3, 118, 151, 188, 218, 234 or pharmaceutically acceptable salt or in vivo hydrolysable ester thereof.

In another aspect of the invention preferred compounds of the invention are those of Examples 47 or 111 or pharmaceutically acceptable salt or in vivo hydrolysable ester thereof.

In a further aspect of the invention preferred compounds of the invention include any one of the Examples or pharmaceutically acceptable salt or in vivo hydrolysable ester thereof.

Preferred aspects of the invention are those which relate to the compound or a pharmaceutically acceptable salt thereof.

A pyrimidine derivative of the formula (I), or a pharmaceutically acceptable salt or an in vivo hydrolysable ester thereof, may be prepared by any process known to be applicable to the preparation of chemically-related compounds. Such processes, when used to prepare a pyrimidine derivative of the formula (I), or a pharmaceutically acceptable salt or an in vivo hydrolysable ester thereof, are provided as a further feature of the invention and are illustrated by the following representative examples in which, unless otherwise stated $R^1$, $Q_1$, $Q_2$, $R^x$, X, $Y^1$, $Y^2$, Z, m and n have any of the meanings defined hereinbefore for a pyrimidine derivative of the formula (I) and unless another substituent is drawn on ring $Q_1$ or $Q_2$ the ring may bear any of the substituents described hereinbefore (optionally protected as necessary). Where a substituent is drawn on ring $Q_1$, this includes (unless stated otherwise) the possibilities of the substituent being on ring $Q_2$ in addition to, or instead of the substituent being on ring $Q_1$. Where X is defined in this section as —NH— it is to be understood that this also includes the posibility of X as —NR$^y$—. Necessary starting materials may be obtained by standard procedures of organic chemistry (see for example, Advanced Organic Chemistry (Wiley-Interscience), Jerry March—also useful for general guidance on reaction conditions and reagents). The preparation of such starting materials is described within the accompanying non-limiting processes and Examples. Alternatively necessary starting materials are obtainable by analogous procedures to those illustrated which are within the ordinary skill of an organic chemist.

Thus, as a further feature of the invention there are provided the following processes which comprises of:

a) reacting a pyrimidine of formula (II):

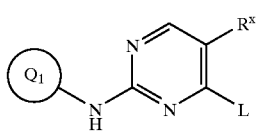
(II)

wherein L is a displaceable group as defined below, with a compound of formula (III):

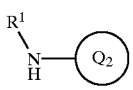
(III)

b) reaction of a pyrimidine of formula (IV):

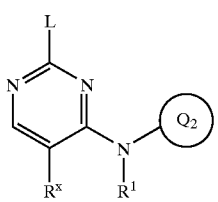
(IV)

wherein L is a displaceable group as defined below, with a compound of formula (V):

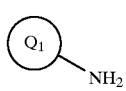
(V)

c) for compounds of formula (I) where n is 1, 2 or 3, m=1, $Y^2$ is H and $Y^1$ is OH, $NH_2$ or SH by reaction of a 3-membered heteroalkyl ring of formula (VI):

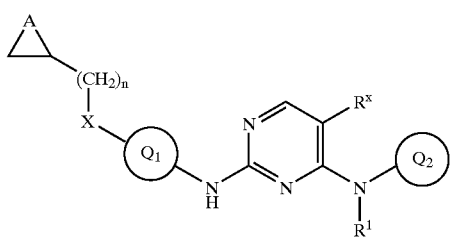
(VI)

wherein A is O, S or NH; with a nucleophile of formula (VII):

Z—D  (VII)

wherein D is H or a suitable counter-ion;

d) for compounds of formula (I) where X is oxygen: by reaction of an alcohol of formula (VIII):

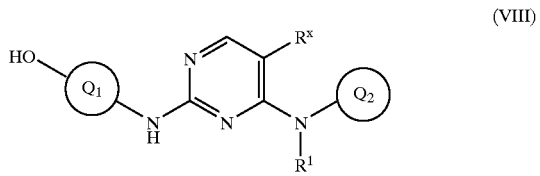
(VIII)

with an alcohol of formula (IX):

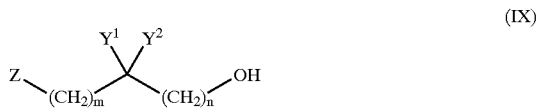
(IX)

e) for compounds of formula (I) wherein X is —$CH_2$—, —O—, —NH— or —S—, $Y^1$ is OH, $Y^2$ is H and m is 2 or 3; reaction of a compound of formula (X):

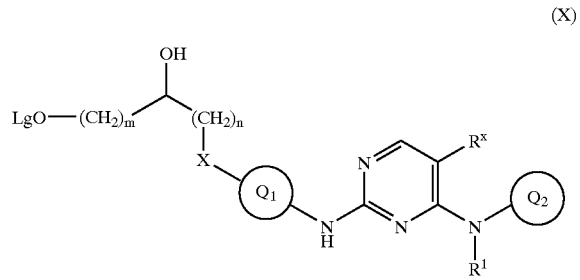
(X)

wherein LgO is a leaving group as defined below; with a nucleophile of formula (VII);

f) for compounds of formula (I) wherein X is —$CH_2$—, —O—, —NH— or —S—; $Y^1$ and $Y^2$ are H; n is 1, 2 or 3 and m is 1, 2 or 3; reaction of a compound of formula (XI):

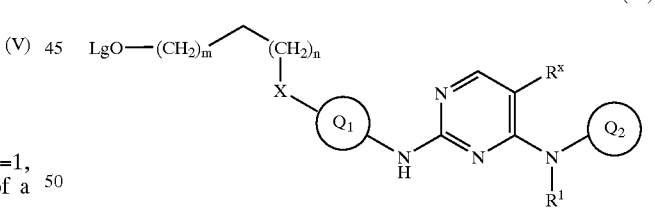
(XI)

wherein LgO is a leaving group as defined below; with a nucleophile of formula (VII);

g) for compounds of formula (I) wherein X is —O—, —NH— or —S—; $Y^1$ and $Y^2$ are H; n is 1, 2 or 3 and m is 1, 2 or 3; reaction of a compound of formula (XII):

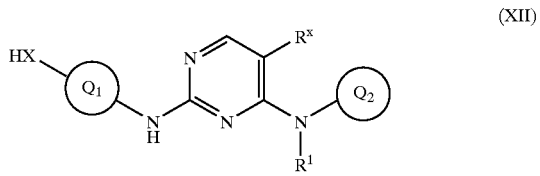
(XII)

with a compound of formula (XIII)

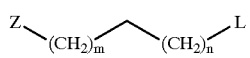
(XIII)

wherein L is a displaceable group as defined below;
h) for compounds of formula (I) in which Z is HS—, by conversion of a thioacetate group in a corresponding compound; and thereafter if necessary:
  i) converting a compound of the formula (I) into another compound of the formula (I);
  ii) removing any protecting groups;
  iii) forming a pharmaceutically acceptable salt or in vivo hydrolysable ester.

L is a displaceable group, suitable values for L are for example, a halo or sulphonyloxy group, for example a chloro, bromo, methanesulphonyloxy or toluene-4-sulphonyloxy group. Alternative suitable groups for L include halo, mesyl, methylthio and methylsulphinyl.

D is hydrogen or a counter-ion. When D is a counter-ion, suitable values for D include sodium and potassium.

LgO is a leaving group. Suitable values for LgO include mesylate and tosylate.

Specific reaction conditions for the above reactions are as follows:

Process a)

Pyrimidines of formula (II) and anilines of formula (III) may be reacted together:
  i) optionally in the presence of a suitable acid, for example an inorganic acid such as hydrochloric acid or sulphuric acid, or an organic acid such as acetic acid or formic acid. The reaction is preferably carried out in a suitable inert solvent or diluent, for example dichloromethane (DCM), acetonitrile, butanol, tetramethylene sulphone, tetrahydrofuran, 1,2-dimethoxyethane, N,N-dimethylformamide, N,N-dimethylacetamide or N-methylpyrrolidin-2-one, and at a temperature in the range, for example, 0° to 150° C., conveniently at or near reflux temperature; or
  ii) under standard Buchwald conditions (for example see J. Am. Chem. Soc., 118, 7215; J. Am. Chem. Soc., 119, 8451; J. Org. Chem., 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis (diphenylphosphino)-1,1'-binaphthyl and at a temperature in the range of 25 to 80° C.

Pyrimidines of the formula (II) may be prepared according to the following scheme:

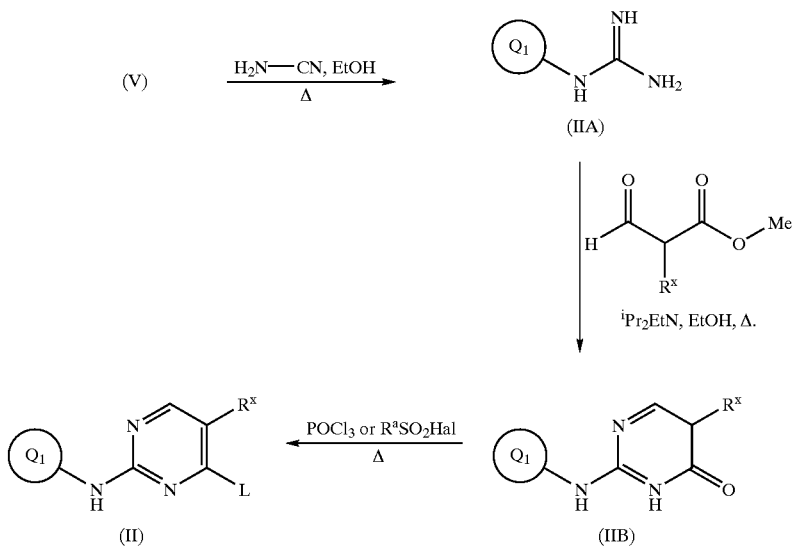

wherein $R^a$ is an optionally substituted alkyl or aryl group and L is a displaceable group as defined above. Preferably $R^a$ is methyl, ethyl or p-tolyl.

Anilines of formula (III) are commercially available or are prepared by processes known in the art.

Process b)

Pyrimidines of formula (IV) and anilines of formula (V) may be reacted together, i) in the presence of a suitable solvent for example a ketone such as acetone or an alcohol such as ethanol or butanol or an aromatic hydrocarbon such as toluene or N-methyl pyrrolidine, optionally in the presence of a suitable acid such as those defined above (or a suitable Lewis acid) and at a temperature in the range of 0° C. to reflux, preferably reflux; or ii) under standard Buchwald conditions as described above.

Pyrimidines of formula (IV) are prepared according to the following scheme:

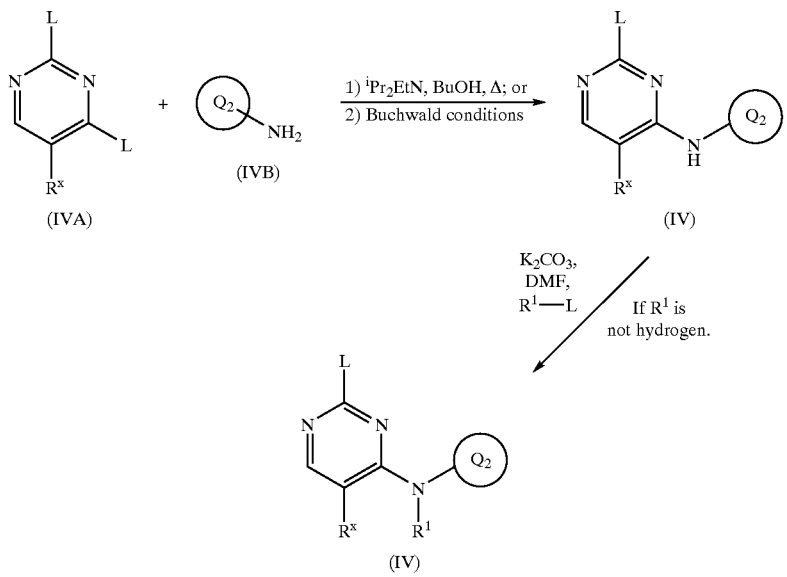

wherein L is a displaceable group as defined above and $R^1$ is not hydrogen.

The anilines of formula (V) are commercially available or are prepared by processes known in the art.

Pyrimidines of the formula (IVA) are commercially available or may be prepared by, for example, reacting a compound of formula (IVA) in which L is —OH (i.e. a uracil), with $POCl_3$ to give a compound of formula (IVA) in which L is —Cl.

Process c)

Three membered heteroalkyl rings of formula (VI) and nucleophiles of formula (VII) are reacted together at a temperature in the range of 20° to 100° C., preferably 20° to 50° C., optionally in the presence of a suitable solvent, for example N,N-dimethylformamide, dimethyl sulphoxide or tetrahydrofuran.

Compounds formula (VI) may be prepared according to the following schemes:

Scheme I)

For compounds of formula (VI) where A is O, and X is not carbon:

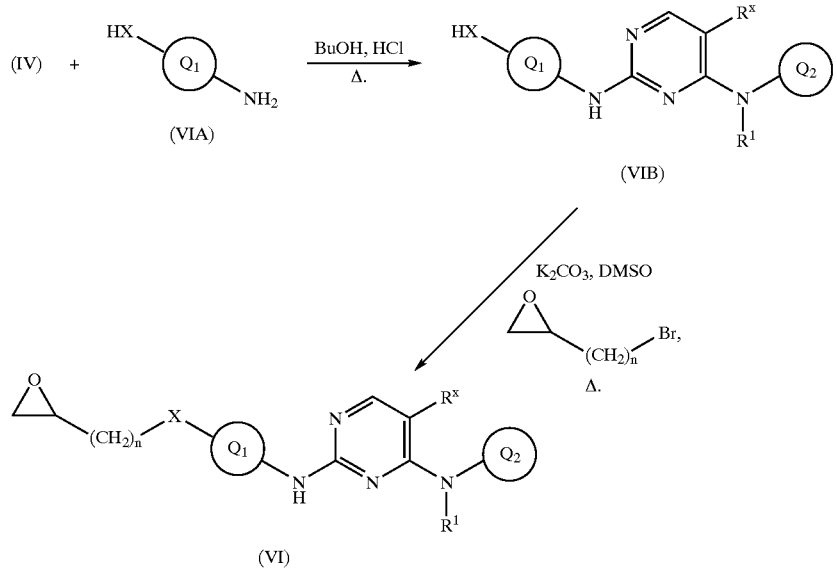

The conversion of (VIB) to (VI) may also be achieved by reaction with Br—$(CH_2)_n$—CHO, or an equivalent ester, in DMF and the presence of a base, followed by reaction with a sulphur ylide such as ($Me_2SOCH_2$) in an inert solvent such as THF (see scheme V).

Scheme II)

For compounds of formula (VI) where A is NH, and X is not carbon:

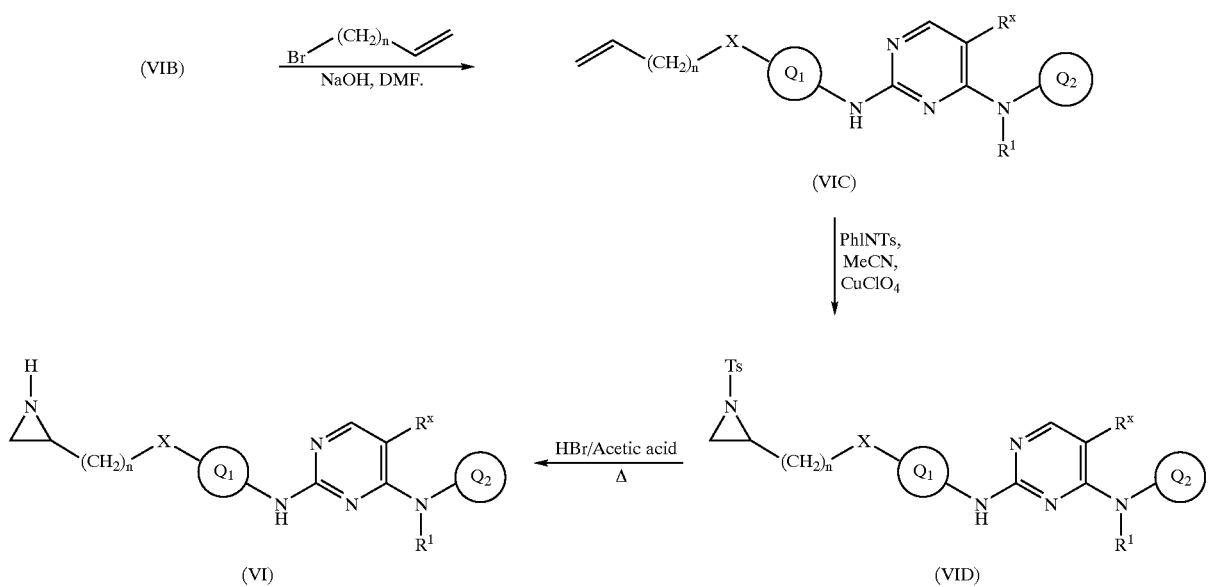
(for PhINTs see, for example, Tet. Let., 1997, 38 (39), 6897–6900; compounds of formula (VIC) may also be oxidised to the epoxide using conditions similar to that in Scheme IV) below);
Scheme III)
For compounds of formula (VI) where A is S, and X is not carbon:
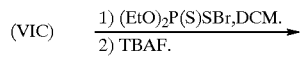
(for example see *Synlett*, 1994, 267–268);
Scheme IV)
For compounds of formula (VI) where X is carbon
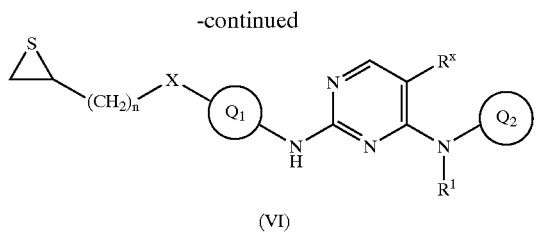
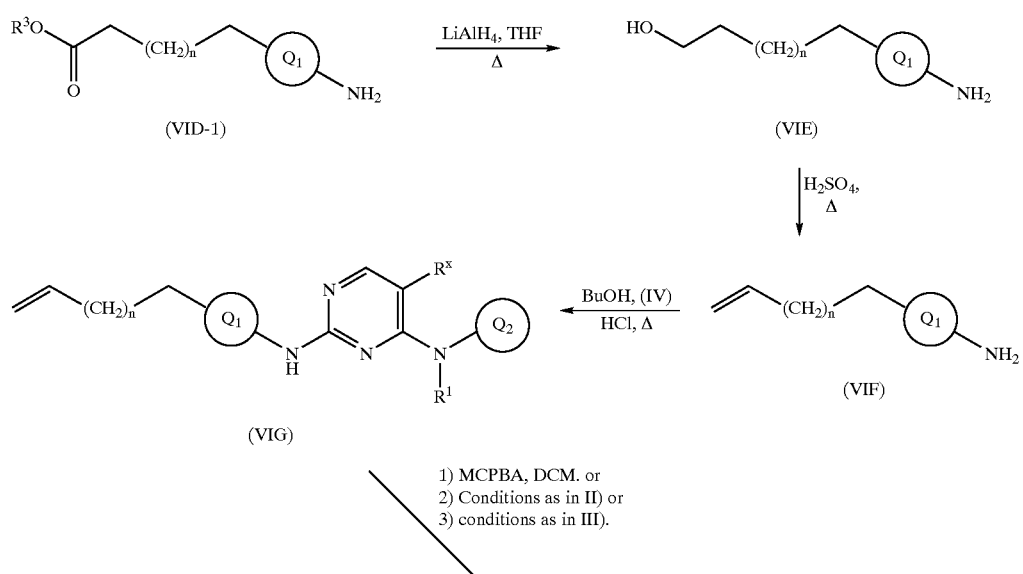
1) MCPBA, DCM. or
2) Conditions as in II) or
3) conditions as in III).

-continued

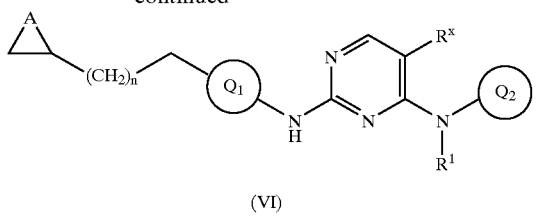

(VI)

wherein R³ together with the —COO— group to which it is attached forms an ester moiety, for example a methyl ester or an ethyl ester.

Scheme V)

For compounds of formula (VI) wherein X is $CH_2$, O, NH or S; Y is OH; n is 1, 2 or 3 and m is 1:

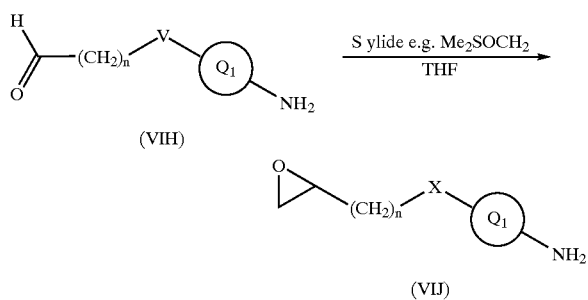

Alcohols of formula (VIII) are made according to the process in I) above for the synthesis of intermediate (VIB) (where X is oxygen).

Alcohols of formula (IX) are commercially available or are made by processes known in the art.

In a process analogous to process d), compounds in which X is —S— may be prepared by reaction of a compound of formula (VIII) in which the hydroxy group is —SH, with a compound of formula (IX) in which the hydroxy group is a leaving group such as mesylate or tosylate.

Process e)

Compounds of formula (X) wherein X is —$CH_2$—, —O—, —NH— or —S—; $Y^1$ is OH, $Y^2$ is H and m is 2 or 3 and nucleophiles of formula (VII) are reacted together at a temperature in the range of 20° to 100° C., preferably 20° to 50° C., optionally in the presence of a suitable solvent, for example N,N-dimethylformamide, dimethyl sulphoxide or tetrahydrofuran, and optionally in the presence of a suitable base, such as potassium carbonate.

Compounds of formula (X) are prepared according to the following scheme (m is 2 or 3):

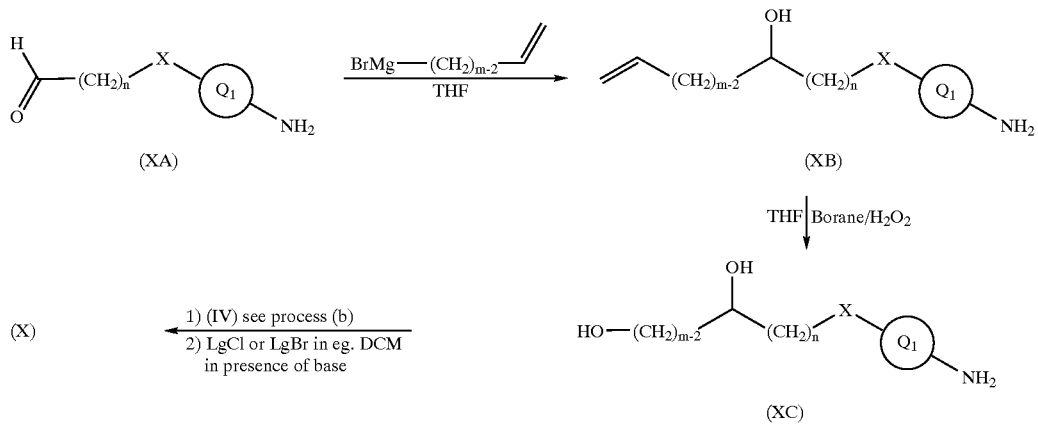

(XB) is reacted with (IV) (see Scheme I) to give (VI).

An equivalent ester of (VIH) may also be used. See also Russ. Chem. Rev. 47, 975–990, 1978.

Compounds of formula (VIH), (VII), (VIA) and (VID-1) are commercially available or are prepared by processes known in the art.

Process d)

Alcohols (e.g. phenols) of formula (VIII) and alcohols of formula (IX) can be reacted together under standard Mitsunobu conditions. For example in the presence of diethyl azodicarboxylate and triphenyl phosphine, in a suitable solvent such as dichloromethane, toluene or tetrahydrofuran, and at a temperature in the range of 0 to 80° C., preferably in the range of 20 to 60° C. Alternatively, alcohols (phenols) of formula (VIII) may be alkylated with a suitable compound of formula (IX) in which the terminal hydroxy group has been replaced by a suitable leaving group.

The order of steps 1) and 2) in the final step may be reversed. A suitable base for step 2) is triethylamine.

Compounds of formula (XA) and (VII) are commercially available or are prepared by processes known in the art. For example, compounds of formula (XA) in which X is —NH—, —O— or —S— may be prepared by reaction of a compound of formula (VIA) with a suitable haloaldehyde or equivalent ester under standard conditions for such reactions.

Process f)

Compounds of formula (XI) and nucleophiles of formula (VII) are reacted together as described for process e) above.

Compounds of formula (XI) are prepared in an analogous manner to step 2) in the final step of the process for preparing compounds of formula (X) above. The necessary primary alcohol starting materials are commercially available or are prepared by processes known in the art.

Process g)

Compounds of formula (XII) and (XIII) are reacted in an inert solvent such as DMF in the presence of a base such as potassium carbonate.

Compounds of formula (XII) are of the same generic formula as compounds of formula (VIB) described herein and are prepared as described for those compounds (see Scheme I). Compounds of formula (XIII) are commercially available or are prepared by processes known in the art.

Process h)

For the compounds of formula (I) in which Z is SH, the conversion of a thioacetate group in a corresponding compound is carried out as described herein for the conversion of compounds of formula (IJ) into (IK).

Suitable starting materials containing a thioacetate group are prepared from corresponding compounds containing a leaving group such as mesylate or tosylate (prepared using standard conditions from the corresponding hydroxy compound) using thiol acetic acid as described herein for the conversion of compounds of formula (IG) into (IJ).

Examples of conversions of a compound of formula (I) into another compound of formula (I) are:

i) conversion of $R^1$ as hydrogen into other $R^1$ for example:

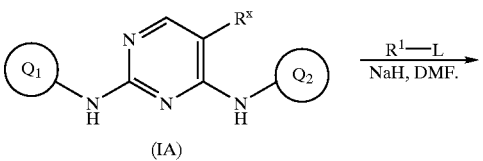

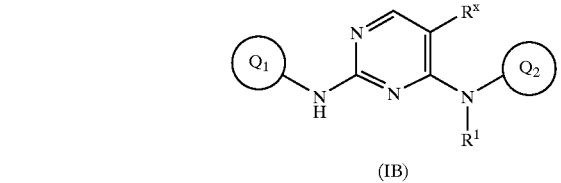

wherein L is a displaceable group as defined above and $R^1$ in the above diagram is not equal to hydrogen;

ii) conversion of $R^1$ as a substituted side chain into another substituted side chain, for example:

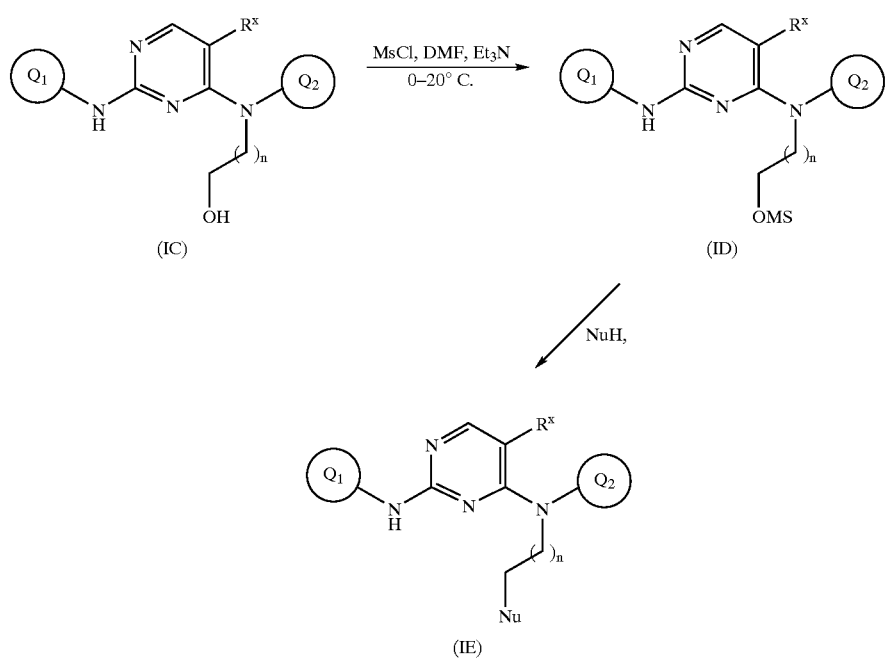

wherein Ms is methanesulphonyl, and Nu is a nucleophile that introduces a substituent that is an optional substituent for $R^1$ as defined in formula (I), such as Nu is —$NH_2$, —$NHC_{1-4}$alkyl, —$N(C_{1-4}$alkyl$)_2$ or —CN (NB the hydroxyl moiety does not necessarily have to be on the terminal carbon as depicted above);

iii) conversion of one side chain of formula (Ia) into another side chain of formula (Ia), for example:

I) for compounds of formula (I) where $Y^2$ is H and $Y^1$ is $NH_2$ (depicted below using ammonia), $C_{1-4}$alkoxy, $C_{1-4}$alkylthio, —$NHC_{1-4}$alkyl, —$N(C_{1-4}$alkyl$)_2$, —$NHC_{3-8}$cycloalkyl, pyrrolidin-1-yl, piperidin-1-yl, piperazin-1-yl, morpholino or thiomorpholino;

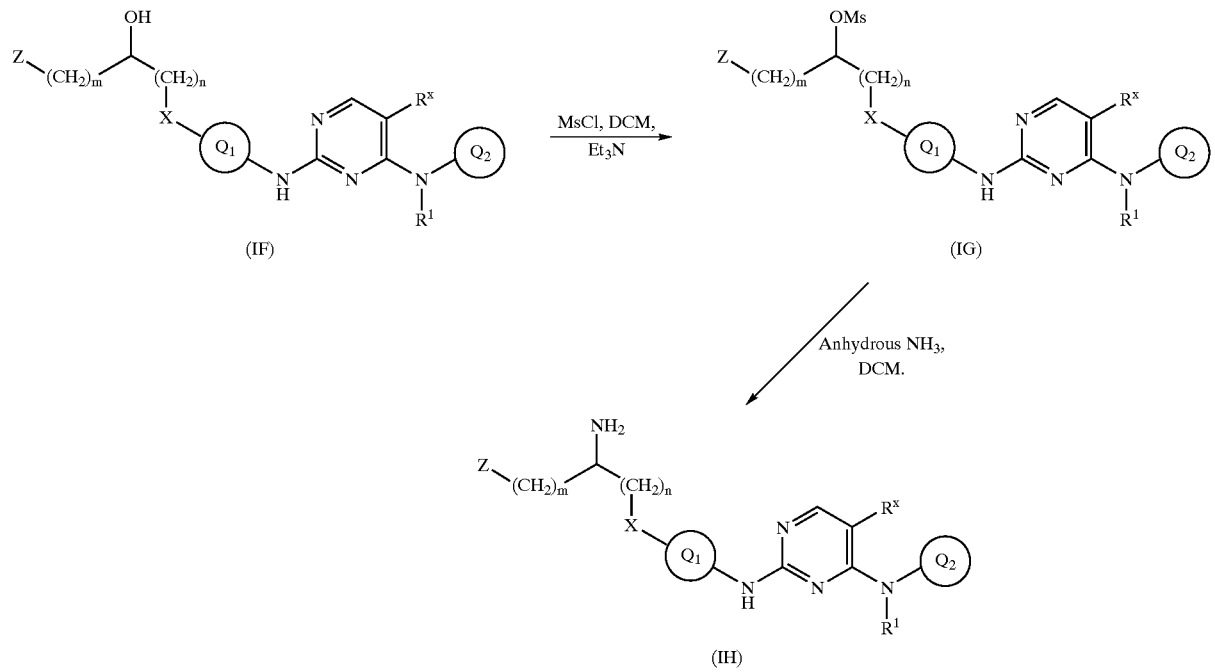
or:
II) for compounds of formula (I) where $Y^2$ is H and $Y^1$ is S:
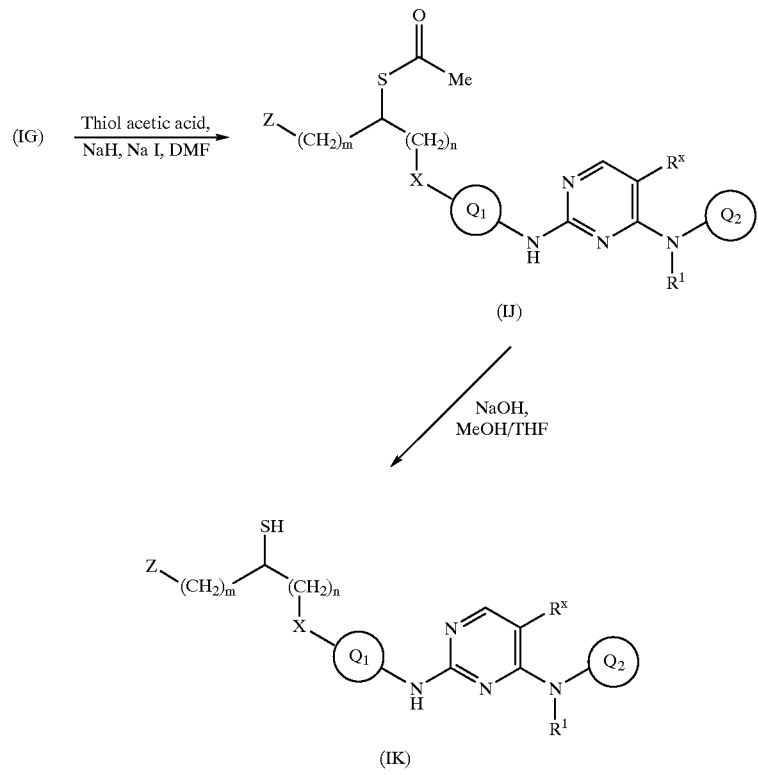

III) for compounds of formula (I) where $Y^2$ is H and $Y^1$ is H:

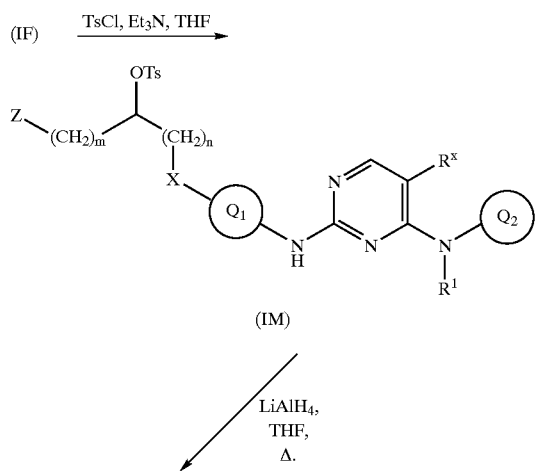

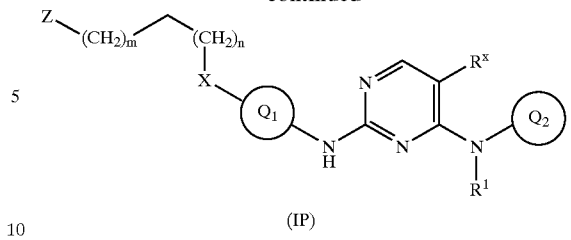

It will be appreciated that these reactions are also suitable for conversion of one side chain of formula (Ia') into another side chain of formula (Ia').

iv) conversion of one value of $R^x$ into another value of $R^x$, using standard techniques, for example, conversion of $R^x$ as hydroxy into $C_{1-3}$alkoxy.

The skilled reader will appreciate that the manipulation of the side chain (Ia) or (Ia') described in Processes c), d), e), f), g) and h) and iii) above and of the sidechain $R^1$ in i) and ii) above may also be performed on intermediates for example to make intermediates of formula (II), (IIA), (IIB), or (V). For example:

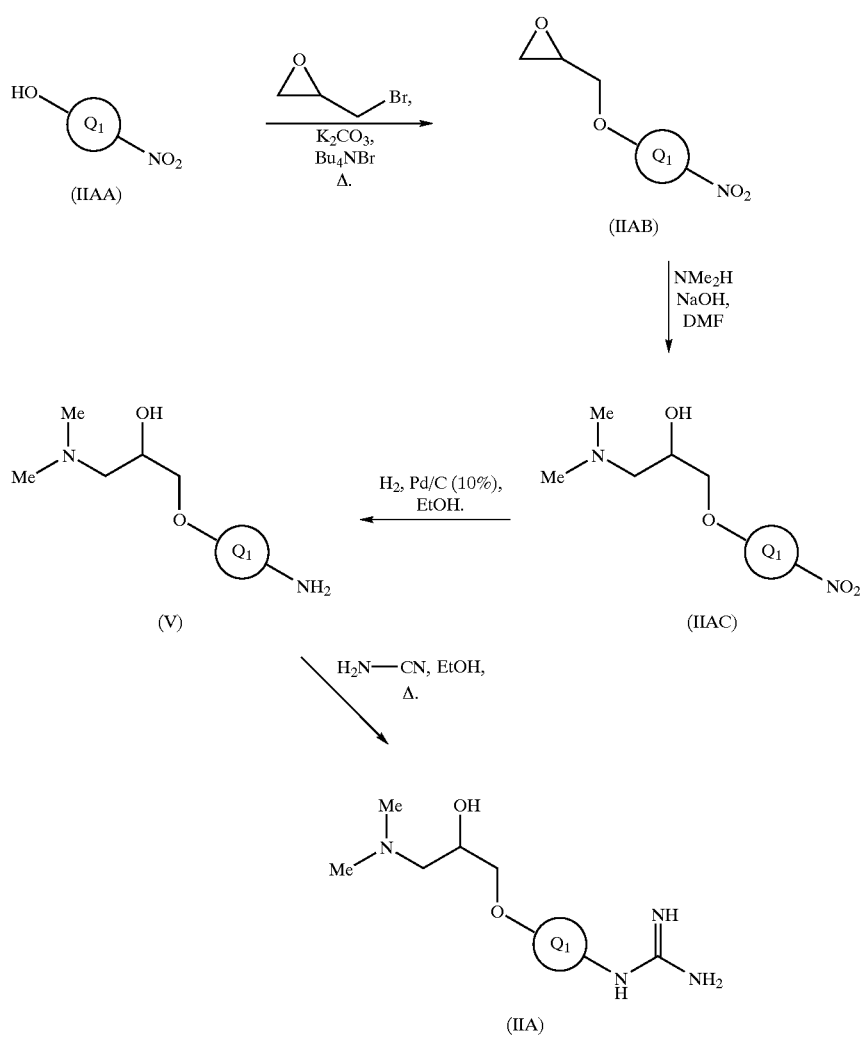

A preferred process of the invention is Process b).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel, for example, those of the formula II and IV and these are provided as a further feature of the invention.

Assays

As stated hereinbefore the pyrimidine derivative defined in the present invention possesses anti-cell-proliferation activity such as anti-cancer activity which is believed to arise from the CDK and/or FAK inhibitory activity of the compound. These properties may be assessed, for example, using the procedure set out below:

CDK4 Inhibition Assay

The following abbreviations have been used:

HEPES is N-(2-Hydroxyethyl)piperazine-N'-(2-ethanesulfonic acid)

DTT is Dithiothretiol

PMSF is Phenylmethylsulfonyl fluoride

The compounds were tested in an in vitro kinase assay in 96 well format using Scintillation Proximity Assay (SPA-obtained from Amersham) for measuring incorporation of [γ-33-P]-Adenosine Triphosphate into a test substrate (GST-Retinoblastoma). In each well was placed the compound to be tested (diluted in DMSO and water to correct concentrations) and in control wells either p16 as an inhibitor control or DMSO as a positive control.

Approximately 0.5 μl of CDK4/Cyclin D1 partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM MnCl$_2$, 1 mM DTT, 100 μM Sodium vanadate, 100 μM NaF, 10 mM Sodium Glycerophosphate, BSA (1 mg/ml final).

As a control, another known inhibitor of CDK4 may be used in place of p16.

Test Substrate

In this assay only part of the retinoblastoma (Science Mar. 13, 1997;235(4794):1394–1399; Lee W. H., Bookstein R., Hong F., Young L. J., Shew J. Y., Lee E. Y.) was used, fused to a GST tag. PCR of retinoblastoma amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac I$^q$ gene for use in any E.Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E.Coli (BL21 (DE3) pLysS cells) using standard inducible expression techniques, and purified as follows.

E.coli paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, imM PMSF, 1 ug/ml leupeptin, 1 ug/ml aprotinin and 1 ug/ml pepstatin) the protein was eluted with 50 mM reduced glutathioiie in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK4 and Cyclin D1

CDK4 and Cyclin D1 were cloned from RNA from MCF-7 cell line (obtained from ATCC number:HTB22, breast adenocarcinoma line) as follows. The RNA was prepared from MCF-7 cells, then reverse transcribed using oligo dT primers. PCR was used to amplify the complete coding sequence of each gene [CDK4 amino acids 1–303; Ref. Cell Oct. 16, 1992; 71(2): 323–334; Matsushime H., Ewen M. E., Stron D. K., Kato J. Y., Hanks S. K., Roussel M. F., Sherr C. J. and Cyclin D1 amino acids 1–296; Ref. Cold Spring Harb. Symp. Quant. Biol., 1991; 56:93–97; Arnold A., Motokura T., Bloom T., Kronenburg, Ruderman J., Juppner H., Kim H. G.].

After sequencing the PCR products were cloned using standard techniques into the insect expression vector pVL1393 (obtained from Invitrogen 1995 catalogue number: V 1392-20). The PCR products were then dually expressed [using a standard virus Baculogold co-infection technique] into the insect SF21 cell system (Spodoptera Frugiperda cells derived from ovarian tissue of the Fall Army Worm—Commercially available).

The following Example provides details of the production of Cyclin D1/CDK4 in SF21 cells (in TC100+10% FBS (TCS)+0.2% Pluronic) having dual infection MOI 3 for each virus of Cyclin D1 & CDK4.

Example Production of Cyclin D1/CDK4

SF21 cells grown in a roller bottle culture to $2.33 \times 10^6$ cells/ml were used to inoculate 10×500 ml roller bottles at $0.2 \times 10E6$ cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

10×500 ml were infected with JS303 Cyclin D1 virus titre—9×10E7 pfu/ml. JS304 CDK4 virus titre—1×10E8 pfu/ml.

Cyclin D1 1.86×10E6×500×3=31 ml of virus for each 500 ml. bottle. $0.9 \times 10^8$ CDK4 1.86×10E6×500×3=28 ml of virus for each 500 ml. bottle. $1 \times 10^8$ The viruses were mixed together before addition to the cultures, and the cultures returned to the roller rig 28° C.

After 3 days (72 hrs.) post infection the 5 Liters of culture was harvested. The total cell count at harvest was 1.58×10E6 cells/ml.(99% viable). The cells were spun out at 2500 rpm, 30 mins., 4° C. in Heraeus Omnifuge 2.0 RS in 250 mls. lots. The supernatant was discarded.

20 pellets of ~4×10E8 cells/pellet were snap frozen in $LN_2$ and stored at −80° C. in CCRF cold room. The SF21 cells were then hypotonically lysed by resuspending in lysis buffer (50 mM HEPES pH 7.5, 10 mM magnesium chloride, 1 mM DTT, 10 mM glycerophosphate, 0.1 mM PMSF, 0.1 mM sodium fluoride, 0.1 mM sodium orthovanadate, 5 ug/ml aprotinin, 5 ug/ml leupeptin and 20% w/v sucrose), and adding ice cold deionised water. After centrifugation, the supernatant was loaded onto a Poros HQ/M 1.4/100 anion exchange column (PE Biosystems, Hertford, UK). CDK4 and Cyclin D1 were coeluted with 375 mM NaCl in lysis buffer, and their presence checked by western blot, using suitable anti-CDK4 and anti-Cyclin D1 antibodies (obtained from Santa Cruz Biotechnology, California, US).

p16 Control (Nature 366:704–707; 1993; Serrano M. Hannon G J. Beach D)

p16 (the natural inhibitor of CDK4/Cyclin D1) was amplified from HeLa cDNA (Hela cells obtained from ATCC CCL2, human epitheloid carcinoma from cervix; Cancer Res. 12: 264, 1952), cloned into pTB 375 NBSE which had a 5' His tag, and transformed using standard techniques into BL21 (DE3) pLysS cells (obtained from Promega; Ref. Studier F. W. and Moffat B. A., J. Mol. Biol., 189, 113, 1986). A 1 liter culture was grown to the appropriate OD then induced with IPTG to express p16 overnight. The cells were then lysed by sonication in 50 mM sodium phosphate, 0.5 M sodium chloride, PMSF, 0.5 $\mu$g/ml leupeptin and 0.5 $\mu$g/ml aprotinin. The mixture was spun down, the supernatant added to nickel chelate beads and mixed for 1½ hours. The beads were washed in sodium phosphate, NaCl pH 6.0 and p16 product eluted in sodium phosphate, NaCl pH 7.4 with 200 mM imidazole.

The pTB NBSE was constructed from pTB 375 NBPE as follows:

p TB375

The background vector used for generation of pTB 375 was pZEN0042 (see UK patent 2253852) and contained the tetA/tetR inducible tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

pTB 375 NBPE

The unique EcoRI restriction site present in pTB 375 was removed. A new multiple cloning site containing the recognition sequences for the restriction enzymes NdeI, BamHI, PstI and EcoRI was introduced into pTB 375 between the NdeI and BamHI sites destroying the original BamHI site present in pTB 375.

pTB 375 NBSE

A new multiple cloning site containing the recognition sequences for the restriction enzymes NdeI, BamHI, SmaI and EcoRI was introduced into pTB 375 NBPE between the NdeI and EcoRI sites. The oligonucleotide containing these restriction sites also contained 6 histidine codons located between the NdeI and BamHI sites in the same reading frame as the inititiator codon (ATG) present within the NdeI site.

By analogy to the above, assays designed to assess inhibition of CDK2 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

If using CDK2 with Cyclin E partial co-purification may be achieved as follows: Sf21 cells are resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homogeniser. After centrifugation, the supernatant is loaded onto a Poros HQ/M 1.4/100 anion exchange column (PE Biosystems, Hertford, UK). CDK2 and Cyclin E are coeluted at the beginning of a 0–1 M NaCl gradient (run in lysis buffer minus protease inhibitors) over 20 column volumes. Co-elution is checked by western blot using both anti-CDK2 and anti-Cyclin E antibodies (Santa Cruz Biotechnology, California, US).

FAK3 Kinase Inhibition Assay

This assay determines the ability of a test compound to inhibit tyrosine kinase activity of human Focal Adhesion Kinase (FAK).

DNA encoding FAK is obtained by total gene synthesis (Edwards M, International Biotechnology Lab 5(3), 19–25, 1987) or by cloning. These are then expressed in a suitable expression system to obtain polypeptide with tyrosine kinase activity. For example, FAK, obtained by expression of recombinant protein in insect cells, was found to display intrinsic tyrosine kinase activity.

FAK (full length human cDNA described by Andre et al (Biochemical and Biophysical Research Communications, 1993, 190 (1): 140–147; EMBL/GenBank Accession Number L05186)) was modified such that the resulting protein when translated had a 6-histidine tag at the N-terminus immediately preceding the start methionine. Active FAK protein has been previously expressed in a baculovirus system using a similar N-terminal 6-histidine tag (Protein Expression And Purification, 1996, 7: 12–18). The human FAK cDNA was cloned into the baculovirus transplacement vector, pFastbac 1 (Life Technologies), and the recombinant construct was co-transfected into insect cells (for example *Spodoptera frugiperda* 21(Sf21)) with viral DNA to prepare recombinant baculovirus (details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York. Details specific to the use of the pFastbac ('Bac to Bac') system are provided in Anderson et al., 1995, FOCUS (Life Technologies Bulletin Magazine), 17, p53.)

For expression of biologically active human FAK protein, Sf21 cells were infected with plaque-pure FAK recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold lysis buffer (50 mM HEPES pH7.5, 1 mM Dithiothreitol, 100 uM Sodium Fluoride, 100 uM Sodium Orthovanadate, 10 mM Glycerophosphate, 100 uM Phenylmethylsulphonylfluoride (PMSF), 5 ug/ml Aprotinin, 5 ug/ml Leupeptin, 1% Tween; the PMSF being added just before use from a freshly-prepared 100 mM solution in methanol) using 250 ul lysis buffer per 10 million cells. The suspension was then incubated on ice for 15 minutes and centrifuged for 10 minutes at 13,000 rpm at 4° C. The supernatant (enzyme stock) was removed and aliquots made which were snap frozen in liquid nitrogen and then stored at −70° C. For a typical batch, stock enzyme was diluted 1 in 250 with enzyme diluent ((100 mM HEPES pH 7.4, 0.2 mM Dithiothreitol, 200 uM Sodium Orthovanadate, 0.1% Triton X-100) and 50 ml of freshly diluted enzyme was used for each assay well (see FAK3 protocol, below).

FAK3: In vitro Enyme Assay Protocol

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Maxisorp 96 well immunoplates Life technologies, Cat. No. 439454A) which were sealed with plate sealers and left overnight at 4° C.

On the day of the assay the substrate solution was discarded and the assay plate wells were washed once with 200 ul PBST (PBS containing 0.05% v/v Tween 20) and once with 200 ul 50 mM Hepes pH7.4.

Test compounds were made up as 10 mM or 30 mM stocks in DMSO and then further diluted in glass distilled water diluted to a concentration 10 fold higher than the final assay concentration. 10 µl of diluted compound was transferred to wells in the washed assay plates. "No compound" control wells contained 10 ul glass distilled water instead of compound.

Forty microliters of 25 mM manganese chloride containing 6.25 µM adenosine-5'-triphosphate (ATP) was added to all test wells. To start the reactions 50 µl of freshly diluted enzyme was added to each well and the plates were incubated at 23 C. for 90 minutes. Then the reaction was stopped by adding 100 ul of PBS containing 20 mM EDTA. The liquid was then discarded and the wells were washed twice with PBST.

One hundred microliters of mouse HRP-linked anti-phosphotyrosine antibody (Santa Cruz, Product SC 7020-HRP), diluted 1 in 1500 with PBST containing 0.5% w/v bovine serum albumin (BSA), was added to each well and the plates were incubated for 1 hour at room temperature before discarding the liquid and washing the wells twice with 200 ul PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the absorbance value of the "no compound" control wells, measured at 405 nm using a plate reading spectrophotometer, was approximately 1.0.

Dose response curves were generated from the absorbance readings using Origin Software. Compounds were ranked for potency using the Inhibitory Concentration 50 (IC50), as defined by Origin Software analysis.

Although the pharmacological properties of the compounds of the formula (I) vary with structural change, in general activity possessed by compounds of the formula (I) in the above assays may be demonstrated at $IC_{50}$ concentrations or doses in the range 250 μM to 1 nM.

When tested in the above in vitro assay the CDK4 inhibitory activity of Example 3 was measured as $IC_{50}$=0.07 μM and that of Example 5 as $IC_{50}$=0.02 μM. When tested in the above in vitro assay the FAK inhibitory activity of Example 6 was measured as $IC_{50}$=0.032 μM and that of Example 220 as $IC_{50}$=0.07 μM.

The in-vivo activity of the compounds of the present invention may be assessed by standard techniques, for example by measuring inhibition of cell growth and assessing cytotoxicity. For example, further details may be found in the following references:

a) Attenution of the Expression of the Focal Adhesion Kinase induces Apoptosis in Tumor Cells. Xu L-h et al. Cell Growth & Differentiation (1996) 7, p413–418;

b) The COOH-Terminal Domain of the Focal Adhesion Kinase Induces Loss of Adhesion and Cell Death in Human Tumour Cells. Xu L-h et al. Cell Growth & Differentiation (1998) 9, p999–1005;

c) Inhibition of pp125-FAK in Cultured Fibroblasts Results in Apoptosis. Hungerford J. E et al. The Journal of Cell Biology (1996) 135, p1383–1390;

d) Inhibition of Focal Adhesion Kinase (FAK) Signalling in Focal Adhesions Decreases Cell Motility and Proliferation. Gilmore A. P and Romer L. H. Molecular Biology of the Cell (1996) 7, p1209–1224.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 μl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% CO2) for three days.

At the end of three days TCA was added to the plates to a final concentration of 16% (v/v). Plates were then incubated at 4° C. for 1 hour, the supernatant removed and the plates washed in tap water. After drying, 100 μl SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pyrimidine derivative of the formula (I), or a pharmaceutically acceptable salt or in vivo hydrolysable ester thereof, as defined hereinbefore for use in a method of treatment of the human or animal body by therapy.

We have found that the pyrimidine derivatives defined in the present invention, or a pharmaceutically acceptable salt or in vivo hydrolysable ester thereof, are effective cell cycle inhibitors (anti-cell proliferation agents), which property (without being bound by theory) is believed to arise from their (G1-S phase) CDK inhibitory properties. The compounds are also effective inhibitors of FAK. Accordingly the compounds of the present invention are expected to be useful in the treatment of diseases or medical conditions mediated alone or in part by CDK and/or FAK enzymes, i.e. the compounds may be used to produce a CDK and/or FAK inhibitory effect in a warm-blooded animal in need of such treatment. Thus the compounds of the present invention provide a method for treating the proliferation and/or migration of malignant cells characterised by inhibition of CDK and/or FAK enzymes, i.e. the compounds may be used to produce an anti-proliferative/migration effect mediated alone or in part by the inhibition of CDKs and/or FAK. The compounds may also be useful as FAK inhibitors by inducing cell-death (apoptosis). Such a pyrimidine derivative of the invention is expected to possess a wide range of anti-cancer properties as CDKs and/or FAK have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDK and/or FAK, especially those tumours which are significantly dependent on CDK and/or FAK for their growth and spread, including for example, certain tumours of the colon, breast, prostate, lung, vulva and skin.

It is further expected that a pyrimidine derivative of the present invention will possess activity against other cell-proliferation/migration diseases in a wide range of other disease states including leukemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a pyrimidine derivative of the formula (I), or a pharmaceutically acceptable salt or in vivo hydrolysable ester thereof, as defined hereinbefore for use as a medicament; and the use of a pyrimidine derivative of the formula (I), or a pharmaceutically acceptable salt or in vivo hydrolysable ester thereof, as defined hereinbefore in the manufacture of a medicament for use in the production of an anti-cancer, cell cycle inhibitory (anti-cell-proliferation) effect and/or a FAK inhibitory (anti-cell migration and/or apoptosis inducing) effect in a warm-blooded animal such as man. Particularly, a cell cycle inhibitory effect is produced at the G1-S phase by inhibition of CDK2, CDK4 and/or CDK6, especially CDK4 and CDK6.

According to a further feature of this aspect of the invention there is provided a method for producing an anti-cancer, cell cycle inhibitory (anti-cell-proliferation) effect and/or a FAK inhibitory (anti-cell migration and/or apoptosis inducing) effect in a warm-blooded animal, such as man, in need of such treatment which comprises administering to said animal an effective amount of a pyrimidine derivative as defined immediately above. Particularly, an inhibitory effect is produced at the G1-S phase by inhibition of CDK2, CDK4 and/or CDK6, especially CDK4 and CDK6.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK and/or FAK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a pyrimidine derivative of the formula (I) as defined hereinbefore and an additional anti-tumour substance as defined hereinbefore for the conjoint treatment of cancer. An anti-emetic may also be usefully administered, for example when using such conjoint treatment as described above.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DMSO-$\delta_6$ (unless otherwise stated) on the delta scale (ppm downfield from tetramethylsilane) using a Varian Gemini 2000 spectrometer operating at a field strength of 300 MHz, or a Bruker AM250 spectrometer operating at a field strength of 250 MHz; and peak multiplicities are shown as follows: s, singlet; d, doublet; dd, double doublet; t, triplet; tt, triple triplet; q, quartet; tq, triple quartet; m, multiplet; br, broad; mass spectrometry (MS) was performed by electrospray on a VG platform;

(vi) unless further details are specified in the text, analytical high performance liquid chromatography (HPLC) was performed on a Waters Spherisorb ODS1 125 cm column, at a flow rate of 2 ml/minute using acetonitrile/water/trifluoroacetic acid (60:40:0.1 v/v) as eluent, detection was at a wavelength of 254 nm, and data are quoted as retention time (RT) in minutes;

(vii) intermediates were not generally fully characterised and purity was assessed by thin layer chromatography (TLC), HPLC, infra-red (IR), MS or NMR analysis;

(viii) where solutions are dried magnesium sulphate was the drying agent;

(ix) the following abbreviations may be used hereinbefore or hereinafter:
DCM dichloromethane;
DMF N,N-dimethylformamide;
DMSO dimethylsulphoxide;
NMP N-methylpyrrolidin-2-one;
THF tetrahydrofuran.

EXAMPLE 1

5-Bromo-2-{4-[2-hydroxy-3-(N,N-dimethylamino) propoxy]anilino}-4-(indan-5-ylamino)pyrimidine A hot solution of 4-[2-hydroxy-3-(N,N-dimethylamino) propoxy]aniline hydrochloride (Method 89, 156 mg, 0.56 mmol) in methanol (2 ml) was added to a solution of 5-bromo-2-chloro-4-(indan-5-ylamino)pyrimidine (Method 15, 200 mg, 0.62 mmol) in n-butanol (20 ml). The mixture was heated at 100° C. for 18 hours and silica.(1 g) was added. Volatile material was removed by evaporation and the residue was purified by column chromatography, eluting with 0–10% 2.0M methanolic ammonia solution in DCM, to give the product as a colourless solid (117 mg, 42%). NMR: 2.03 (m, 2H), 2.18 (s, 6H), 2.32 (m, 2H), 2.83 (m, 4H), 3.80 (m, 3H), 4.76 (d, 1H), 6.70 (d, 2H), 7.17 (m, 1H), 7.23 (m, 1H), 7.41 (m, 3H), 8.10 (s, 1H), 8.35 (s, 1H), 9.03 (s, 1H); MS (MH$^+$): 498.4, 500.4.

EXAMPLES 2–41

The following compounds were prepared by an analogous method to that described in Example 1, using 4-[2-hydroxy-3-(N,N-dimethylamino)propoxy]aniline hydrochloride and the appropriate 5-substituted 4-anilino-2-chloropyrimidine (Methods 7, 9, 11–45, 62–64, or obtained as described in J. Chem. Soc. Perkin Trans. I, 1974, 1970):

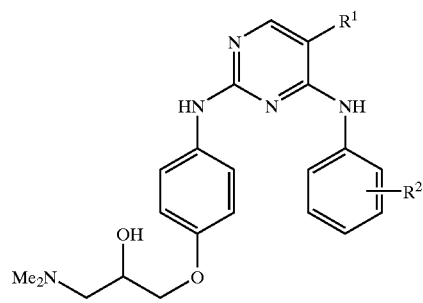

| Ex | R$^1$ | R$^2$ | NMR | MS (MH$^+$) |
|---|---|---|---|---|
| 2 | Me | H | 2.09(s, 3H), 2.18(s, 6H), 2.30(m, 2H), 3.78 (m, 3H), 4.76(d, 1H), 6.76(d, 2H), 7.02(t, 1H), 7.29(t, 2H), 7.52(d, 2H), 7.69(d, 2H), 7.83(s, 1H), 8.17(s, 1H), 8.72(s, 1H) | 394.2 |

-continued

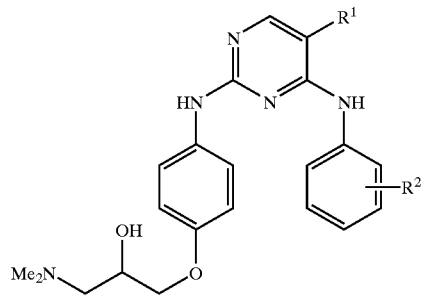

| Ex | R¹ | R² | NMR | MS (MH⁺) |
|---|---|---|---|---|
| 3 | Br | H | 2.19(s, 6H), 2.31(m, 2H), 3.82(m, 3H), 4.75 (d, 1H), 6.74(d, 2H), 7.12(t, 1H), 7.34(t, 2H), 7.43(d, 2H), 7.61(d, 2H), 8.16(s, 1H), 8.44(s, 1H), 9.09(s, 1H) | 458.3, 460.3 |
| 4 | Br | 2-Ph | 2.18(s, 6H), 2.31(m, 2H), 3.80(m, 3H), 4.74 (d, 1H), 6.63(d, 2H), 7.36(m, 10H), 7.68(d, 1H), 7.98(s, 1H), 8.20(s, 1H), 8.98(s, 1H) | 534.5, 536.5 |
| 5 | Br | 2-F, 5-Me | 2.18(s, 6H), 2.29(m, 5H), 3.78(m, 3H), 4.73 (d, 1H), 6.62(d, 2H), 7.09(m, 1H), 7.18(m, 1H), 7.34(m, 3H), 8.14(s, 1H), 8.38(s, 1H), 9.05(s, 1H) | 490.4, 492.4 |
| 6 | NO₂ | 2-F | 2.19(s, 6H), 2.31(m, 2H), 3.82(m, 3H), 4.77 (br, 1H), 6.67(m, 2H), 7.22(m, 1H), 7.37(m, 4H), 7.68(m, 1H), 9.03(s, 1H) | 443.4 |
| 7 | ![structure: CH3-C(=O)-NH-CH(Me)2] | H | 1.18(d, 6H), 2.18(s, 6H), 2.32(m, 2H), 3.83 (m, 3H), 4.08(m, 1H), 4.76(d, 1H), 6.81(d, 2H), 7.04(t, 1H), 7.29(t, 2H), 7.52(d, 2H), 7.63(d, 2H), 8.16(d, 1H), 8.64(s, 1H), 9.43(s, 1H) | 465.5 |
| 8 | Br | 2-Br, 4-Me | 2.18(s, 6H), 2.31(m, 5H), 3.78(m, 3H), 4.75 (d, 1H), 6.60(d, 2H), 7.24(m, 3H), 7.58(m, 2H), 8.12(s, 1H), 8.39(s, 1H), 9.06(s, 1H) | 550.4, 552.4, 554.4 |
| 9 | Br | 2-morpholino | 2.18(s, 6H), 2.31(m, 2H), 2.82(m, 4H), 3.80 (m, 5H), 3.90(m, 2H), 4.76(br, 1H), 6.83(d, 2H), 7.08(m, 2H), 7.30(m, 1H), 7.49(d, 2H), 8.19(s, 1H), 8.82(s, 1H), 9.20(s, 1H) | 543.5, 545.5 |
| 10 | Br | 4-Br | 2.18(s, 6H), 2.32(m, 2H), 3.83(m, 3H), 4.76 (d, 1H), 6.77(d, 2H), 7.40(d, 2H), 7.46(m, 2H), 7.59(m, 2H), 8.16(s, 1H), 8.38(s, 1H), 9.10(s, 1H) | 536.5, 538.4, 540.4 |
| 11 | Me | 3-Cl | 2.08(s, 3H), 2.18(s, 6H), 2.2–2.45(m, 2H), 3.75–3.9(m, 3H), 4.73(br s, 1H), 6.78(d, 2H), 7.04(d, 2H), 7.30(dd, 1H), 7.49(d, 2H), 7.69 (d, 1H), 7.82(s, 1H), 7.87(s, 1H), 8.28(s, 1H), 8.80(s, 1H) | 428.2, 430.2 |
| 12 | Me | 3,4-di-Cl | 2.07(s, 3H), 2.18(s, 6H), 2.2–2.45(m, 2H), 3.75–3.9(m, 3H), 4.74(br s, 1H), 6.80(d, 2H), 7.45-7.55(m, 3H), 7.74(dd, 1H), 7.89(s, 1H), 8.05(d, 1H), 8.37(s, 1H), 8.84(s, 1H) | 461.8, 463.7 |
| 13 | Cl | H | 2.18(s, 6H), 2.30(m, 2H), 3.82(m, 3H), 4.76 (d, 1H), 6.77(d, 2H), 7.12(t, 1H), 7.34(t, 2H), 7.46(d, 2H), 7.64(d, 2H), 8.07(s, 1H), 8.71(s, 1H), 9.07(s, 1H) | 414.4, 416.4 |
| 14 | Cl | 2-Cl, 5-Me | 2.18(s, 6H), 2.30(m, 5H), 3.79(m, 3H), 4.76 (d, 1H), 6.62(d, 2H), 7.10(m, 1H), 7.31(d, 2H), 7.42(d, 1H), 7.54(s, 1H), 8.06(s, 1H), 8.55(s, 1H), 9.08(s, 1H) | 462.4, 464.4, 466.4 |
| 15 | Cl | 2-morpholino | 2.19(s, 6H), 2.33(m, 2H), 2.82(s, 4H), 3.82 (m, 7H), 4.77(d, 1H), 6.83(d, 2H), 7.09(m, 2H), 7.38(m, 1H), 7.49(m, 2H), 8.16(s, 1H), 8.48(m, 1H), 8.80(s, 1H), 9.21(s, 1H) | 499.5, 501.5 |
| 16 | Cl | 4-Br | 2.19(s, 6H), 2.33(m, 2H), 3.84(m, 3H), 4.77 (d, 1H), 6.78(d, 2H), 7.42(m, 4H), 7.63(d, 2H), 8.09(s, 1H), 8.82(s, 1H), 9.12(s, 1H) | 492.4, 494.4, 496.4, |

-continued

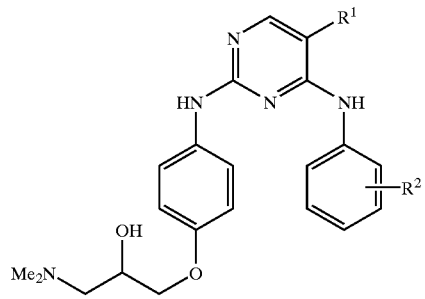

| Ex | R¹ | R² | NMR | MS (MH⁺) |
|---|---|---|---|---|
| 17 | Br | 2-PhCH₂— | 2.15(s, 6H), 2.3(m, 2H), 3.7(m, 1H), 3.85(m, 2H), 3.9(s, 2H), 4.7(d, 1H), 6.6(d, 2H), 7.0–7.3(m, 10H), 7.4(d, 1H), 8.05(s, 1H), 8.25(s, 1H), 9.0(s, 1H) | 548, 550 |
| 18 | Br | 2-PhO— | 2.8(s, 6H), 3.2(m, 2H), 3.9(m, 2H), 4.2(s, 1H), 5.9(s, 1H), 6.8(d, 2H), 6.95(m, 3H), 7.1 (t, 1H), 7.2(m, 2H), 7.3(t, 2H), 7.45(d, 2H), 8.05(s, 1H), 8.1(m, 1H), 9.2(s, 1H) | 550, 552 |
| 19 | Br | 2-PhCH₂O— | 2.2(s, 6H), 2.4(m, 2H), 3.8(m 1H), 3.9(m, 2H), 4.8(s, 1H), 5.2(s, 2H), 6.8(d, 2H), 6.95 (t, 1H), 7.1(t, 1H), 7.2(m, 1H), 7.3(m, 3H), 7.55(m, 4H), 8.1(s, 1H), 8.2(m, 2H), 9.2(s, 1H) | 564, 566 |
| 20 | NO₂ | H | 2.1(s, 6H), 2.3(m, 2H), 3.8–4.0(m, 3H), 4.8 (d, 1H), 6.7(m, 2H), 7.15(t, 1H), 7.4(m, 4H), 7.6(d, 2H), 9.1(s, 1H) | 425 |
| 21 | F | H | 2.19(s, 6H), 2.34(m, 2H), 3.82(m, 3H), 4.76 (d, 1H), 6.79(d, 2H), 7.03(t, 1H), 7.30(t, 2H), 7.50(d, 2H), 7.77(d, 2H), 8.03(d, 1H), 8.94 (s, 1H), 9.22(s, 1H) | 398.4 |
| 22 | F | 2-Cl, 5-Me | 2.17(s, 6H), 2.30(m, 5H), 3.78(m, 3H), 4.76 (d, 1H), 6.62(d, 2H), 7.09(m, 1H), 7.39(m, 4H), 8.02(d, 1H), 8.89(m, 2H) | 446.4, 448.4 |
| 23 | F | 2-morpholino | 2.18(s, 6H), 2.34(m, 2H), 2.83(m, 4H), 3.71 (m, 4H), 3.82(m, 3H), 4.76(d, 1H), 6.80(d, 2H), 7.09(m, 2H), 7.26(m, 1H), 7.51(d, 2H), 8.07(d, 1H), 8.33(m, 1H), 8.50(d, 1H), 9.03 (s, 1H) | 483.5 |
| 24 | F | 4-Br | 2.18(s, 6H), 2.32(m, 2H), 3.78(m, 3H), 4.77 (d, 1H), 6.81(d, 2H), 7.44(m, 4H), 7.76(m, 2H), 8.07(d, 1H), 8.98(s, 1H), 9.38(s, 1H) | 476.4, 478.4 |
| 25 | morpholino | H | 2.8(m, 10H), 3.2(m, 2H), 3.8(m, 4H), 3.9(s, 2H), 4.2(s, 1H), 5.9(s, 1H), 6.8(d, 2H), 7.0(t, 1H), 7.3(t, 2H), 7.6(d, 2H), 7.8(d, 2H), 8.0(s, 1H), 8.3(s, 1H), 8.9(s, 1H) | 465.5 |
| 26 | Br | 4-PhCH₂O— | 2.35(s, 6H), 2.6(m, 2H), 3.8(m, 2H), 4.0(m, 1H), 5.1(s, 2H), 6.6(d, 2H), 7.0(d, 2H), 7.3–7.5(m, 9H), 8.1(s, 1H), 8.4(s, 1H), 9.05(s, 1H) | 564, 566 |
| 27 | Br | 3-PhO— | 2.15(s, 6H), 2.3(m, 2H), 3.7–3.9(m, 3H), 4.7 (s, 1H), 6.7(m, 3H), 7.0–7.2(m, 3H), 7.3–7.6 (m, 7H), 8.2(s, 1H), 8.5(s, 1H), 9.1(s, 1H) | 550, 552 |
| 28 | Br | 4-PhO— | 2.5(s, 6H), 2.8(m, 2H), 3.8(m, 1H), 4.0(m, 2H), 6.7(d, 2H), 7.0(m, 4H), 7.1(t, 1H), 7.4 (m, 4H), 7.6(d, 2H), 8.1(s, 1H), 8.5(s, 1H), 9.1(s, 1H) | 550, 552 |
| 29 | Br | 3-PhCH₂O— | 2.1(s, 6H), 2.3(m, 2H), 3.75(m, 1H), 3.85(m, 2H), 4.65(s, 1H), 5.0(s, 2H), 6.75(m, 3H), 7.2–7.5(m, 10H), 8.15(s, 1H), 8.3(s, 1H), 9.1 (s, 1H) | 564, 566 |

-continued

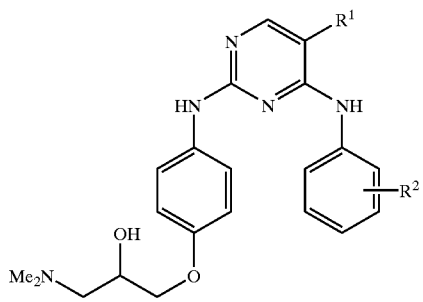

| Ex | R¹ | R² | NMR | MS (MH⁺) |
|---|---|---|---|---|
| 30[1] | Br | 4-PhCH₂— | 2.8(s, 6H), 3.2(m, 2H), 3.85(m 2H), 3.95(s, 2H), 4.2(s, 1H), 5.9(d, 1H), 6.7(d, 2H), 7.1–7.3(m, 7H), 7.5(t, 4H), 8.1(s, 1H), 8.35(s, 1H), 9.1(s, 1H) | 548, 550 |
| 31 | Cl | 3,4-di-Cl | 2.19(s, 6H), 2.34(m, 2H), 3.84(m, 3H), 4.76 (br, 1H), 6.80(d, 2H), 7.41(d, 2H), 7.50(d, 1H), 7.69(m, 1H), 8.00(m, 1H), 8.14(s, 1H), 8.9(s, 1H), 9.19(s, 1H) | 482.4, 484.4, 486.4 |
| 32 | Cl | 2-F, 5-Me | 2.18(s, 6H), 2.28(m, 5H), 3.79(m, 3H), 4.76 (d, 1H), 6.62(d, 2H), 7.14(m, 2H), 7.32(m, 3H), 8.05(s, 1H), 8.61(s, 1H), 9.07(s, 1H) | 446.4, 448.4 |
| 33 | Cl | 3,4-(CH₂)₃—** | 2.03(m, 2H), 2.18(s, 6H), 2.31(m, 2H), 2.82 (m, 4H), 3.82(m, 3H), 4.76(d, 1H), 6.74(d, 2H), 7.16(d, 1H), 7.28(m, 1H), 7.43(d, 2H), 7.49(br, 1H), 8.04(s, 1H), 8.59(s, 1H), 9.03 (s, 1H) | 454.5, 456.5 |
| 34 | Cl | 2-CN | 2.18(s, 6H), 2.30(m, 2H), 3.78(m, 3H), 4.76 (d, 1H), 6.62(d, 2H), 7.27(d, 2H), 7.43(m, 1H), 7.62(m, 1H), 7.74(m, 1H), 7.88(m, 1H), 8.12(s, 1H), 9.13(s, 1H), 9.19(br, 1H) | 439.4, 441.4 |
| 35 | PhCH₂— | H | 2.18(s, 6H), 2.2–2.45(m, 2H), 3.75–3.9(m, 3H), 3.92(s, 2H), 4.73(br s, 1H), 6.74(d, 2H), 7.01(t, 1H), 7.1–7.35(m, 7H), 7.50(d, 2H), 7.62(d, 2H), 7.79(s, 1H), 8.17(s, 1H), 8.81(s, 1H) | 470.5 |
| 36 | EtO— | H | 1.4(t, 3H), 2.2(s, 6H), 2.25(dd, 1H), 2.4(dd, 1H), 3.75–3.9(m, 3H), 4.05(q, 2H), 6.8(d, 2H), 7.0(t, 1H), 7.3(t, 2H), 7.55(d, 2H), 7.8 (s, 1H), 7.85(d, 2H), 8.4(s, 1H), 8.65(s, 1H) | 424.5 |
| 37 | Br | 4-HOCH₂— | 2.18(s, 6H), 2.2–2.45(m, 2H), 3.75–3.9(m, 3H), 4.49(d, 2H), 4.74(d, 1H), 5.13(t, 1H), 6.74(d, 2H), 7.27(d, 2H), 7.44(d, 2H), 7.54 (d, 2H), 8.13(s, 1H), 8.43(s, 1H), 9.07(s, 1H) | 488.1, 490.1 |
| 38[2] | Br | 4-ⁿBuOCH₂— | 0.89(t, 3H), 1.36(tq, 2H), 1.54(tt, 2H), 2.18 (s, 6H), 2.2–2.45(m, 2H), 3.44(t, 2H), 3.75–3.9 (m, 3H), 4.44(s, 2H), 4.78(d, 1H), 6.74(d, 2H), 7.29(d, 2H), 7.45(d, 2H), 7.59(d, 2H), 8.17(s, 1H), 8.53(s, 1H), 9.13(s, 1H) | 544.6, 546.6 |
| 39 | CH₂=CH— | H | 2.2(s, 6H), 2.3(dd, 1H), 2.4(dd, 1H), 3.75–3.95(m, 3H), 4.75(br d, 1H), 5.15(d, 1H), 5.6 (d, 1H), 6.75(d, 2H), 6.95(dd, 1H), 7.05(t, 1H), 7.3(t, 2H), 7.55(d, 2H), 7.65(d, 2H), 8.25(s, 1H), 8.6(s, 1H), 9.0(s, 1H) | 406.5 |
| 40 | MeO | H | 2.2(s, 6H), 2.3(dd, 1H), 2.4(dd, 1H), 3.8–4.0 (m, 6H), 6.8(d, 2H), 7.0(t, 1H), 7.3(t, 2H), 7.6(d, 2H), 7.8(s, 1H), 7.85(d, 2H), 8.6(s, 1H), 8.65(s, 1H) | 410.4 |
| 41[3] | CN | H | 2.17(s, 6H), 2.2–2.4(m, 2H), 3.75–3.9(m, 3H), 4.76(d, 1H), 6.76(br d, 2H), 7.14(t, 1H), 7.34 (dd, 2H), 7.45(d, 2H), 7.55(br d, 2H), 8.44(s, 1H), 9.39(br s, 1H), 9.71(br s, 1H) | 405.4 |

[1]Isolated as hydrochloride salt.
[2]Obtained as a by-product from Example 37 by evaporation of the less polar chromatography fractions.
[3]Prepared from 4-anilino-5-cyano-2-(methanesulphonyl)pyrimidine (Method 64).
**Such that R² and the phenyl ring to which it is attached forms indan-5-yl.

EXAMPLES 42–43

The following compounds were prepared by an analogous method to that described in Example 1, using 4-[2-hydroxy-3-(N,N-dimethylamino)propoxy]aniline hydrochloride and the appropriate 4-anilino-5-bromo-2-chloropyrimidine (Methods 46–47):

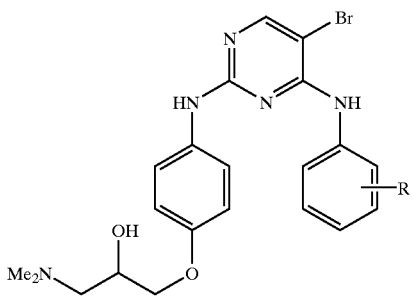

| Ex | R | MS (MH+) | HPLC (RT)[1] |
|---|---|---|---|
| 42[2] | 3-CF3 | 526, 528 | 1.75 |
| 43 | 4-CF3 | 526, 528 | 1.74 |

[1] Data obtained from a Hypersil 10 cm base deactivated reverse phase column, using 5–95% acetonitrile/water gradient, flow rate 1 ml/min over 10 minutes.
[2] The product obtained after chromatography was washed with t-butylmethylether.

EXAMPLE 44

5-Bromo-4-(3-chloroanilino)-2-{4-[2-hydroxy-3-(N,N-dimethylamino)propoxy]anilino}pyrimidine A solution of 5-bromo-2,4-dichloropyrimidine (228 mg, 1.0 mmol), 3-chloroaniline (140 mg, 1.1 mmol) and N,N-diisopropylethylamine (148 mg, 1.15 mmol) in n-butanol (10 ml) was heated at 100° C. for 6 hours. A solution of 4-[2-hydroxy-3-(N,N-dimethylamino) propoxy]aniline hydrochloride (Method 89, 250 mg, 0.90 mmol) in methanol (3 ml) was added and the solution was heated at 100° C. for 20 hours and then concentrated to a volume of 5 ml. The solution was loaded on a Varian Mega Bond Elut column and the column was eluted with 0–4% 2.0M methanolic ammonia solution in DCM. Concentration of the appropriate fractions and recrystallization of the residue from a mixture of acetonitrile and ether gave the product, isolated as a hydrochloride salt (110 mg, 21%). NMR: 2.8 (s, 6H), 3.05–3.3 (m, 2H), 3.8–3.9 (m, 2H), 4.25–4.3 (m, 1H), 5.9 (d, 1H), 6.8 (d, 2H), 7.15 (d, 1H), 7.35 (t, 1H), 7.5 (d, 2H), 7.6 (d, 1H), 7.75 (s, 1H), 8.2 (s, 1H), 8.6 (s, 1H), 9.2 (s, 1H), 9.8 (br s, 1H); MS (MH+): 492, 494, 496.

EXAMPLES 45–78

The following compounds were prepared by an analogous method to that described in Example 44, using the appropriate 5-substituted 2,4-dichloropyrimidine, the appropriate substituted aniline and 4-[2-hydroxy-3-(N,N-dimethylamino)propoxy]aniline hydrochloride (Method 89).

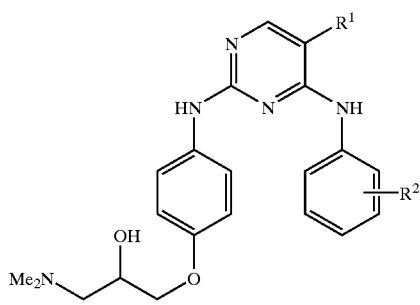

| Ex | R[1] | R[2] | NMR | MS (MH+) |
|---|---|---|---|---|
| 45 | Br | 4-F | 2.8(s, 6H), 3.15–3.25(m, 2H), 3.9(m, 2H), 4.25(m, 1H), 5.9(d, 1H), 6.8(d, 2H), 7.2(t, 2H), 7.4(d, 2H), 7.6(m, 2H), 8.15(s, 1H), 8.6 (s, 1H), 9.15(s, 1H), 9.75(br s, 1H) | 476, 478 |
| 46 | Br | 4-MeO— | 2.8(s, 6H), 3.15–3.25(m, 2H), 3.8(s, 3H), 3.9 (m, 2H), 4.25(m, 1H), 5.9(d, 1H), 6.7(d, 2H), 6.9(d, 2H), 7.5(dd, 4H), 8.1(s, 1H), 8.4(1H), 9.05(s, 1H), 9.8(br s, 1H) | 488, 490 |
| 47 | Br | 4-Cl | 2.8(s, 6H), 3.15–3.25(m, 2H), 3.9(m, 2H), 4.25(m, 1H), 5.9(d, 1H), 6.8(d, 2H), 7.35(d, 2H), 7.45(d, 2H), 7.65(d, 2H), 8.2(s, 1H), 8.6 (1H), 9.2(s, 1H), 9.8(br s, 1H) | 492, 494, 496 |
| 48 | Br | 3-Cl, 4-F | 2.8(s, 6H), 3.15–3.25(m, 2H), 3.9(m, 2H), 4.25(m, 1H), 5.9(d, 1H), 6.8(d, 2H), 7.35–7.45(m, 3H), 7.6(m, 1H), 7.85(m, 1H), 8.2(s, 1H), 8.65(1H), 9.2(s, 1H), 9.7(br s, 1H) | 510, 512, 514 |
| 49 | Br | 4-$^n$BuO— | 0.95(t, 3H), 1.4–1.45(m, 2H), 1.55–1.6(m, 2H), 2.8(m, 6H), 3.05–3.15(m, 2H), 3.9(m, 2H), 4.0(t, 2H), 4.2(m, 1H), 5.9(br s, 1H), 6.75(d, 2H), 6.9(d, 2H), 7.4(t, 4H), 8.1(s, 1H), 8.4(s, 1H), 9.05(s, 1H), 9.8(br s, 1H) | 530, 532 |

-continued

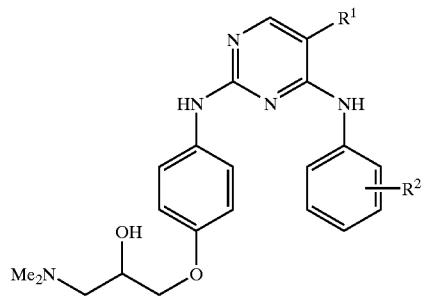

| Ex | R¹ | R² | NMR | MS (MH⁺) |
|---|---|---|---|---|
| 50[1] | Br | 3,4-CH=N—NH—** | 2.8(dd, 6H), 3.1–3.3(m, 2H), 3.8–3.9(m, 2H), 4.2–4.3(m, 1H), 6.6(d, 2H), 7.3(d, 2H), 7.4(dd, 1H), 7.6(d, 1H), 7.85(s, 1H), 8.1(s, 1H), 8.35(s, 1H), 9.75(br s, 1H), 9.9(br s, 1H), 10.2–10.4(br s, 1H) | 498, 500 |
| 51 | Br | 2-F | 2.8(s, 6H), 3.05–3.15(m, 2H), 3.8–3.9(m, 2H), 4.2–4.25(m, 1H), 5.9(d, 1H), 6.65(d, 2H), 7.2(m, 1H), 7.3–7.4(m, 3H), 7.5–7.6(t, 1H), 8.15(s, 1H), 8.5(s, 1H), 9.15(s, 1H), 9.8(br s, 1H) | 476, 478 |
| 52 | Br | 2-MeO— | 2.7(s, 6H), 2.9–3.2(m, 2H), 3.8(s, 3H), 3.95(d, 2H), 4.2(m, 1H), 6.8(d, 2H), 6.9(m, 1H), 7.1(m, 2H), 7.4(d, 2H), 7.4–7.9(br s, 1H), 8.0(s, 1H), 8.15(br s, 1H), 8.2(s, 1H) 9.2(s, 1H) | 488, 490 |
| 53 | Br | 3-MeO— | 2.8(s, 6H), 3.1–3.3(m, 2H), 3.7(s, 3H), 3.8–4.0(m, 2H), 4.15(m, 1H), 5.9(d, 1H), 6.7(m, 1H), 6.8(d, 2H), 7.2(m, 3H), 7.5(d, 2H), 8.15(s, 1H), 8.4(s, 1H), 9.2(s, 1H), 9.8–10.0(br s, 1H) | 488, 490 |
| 54 | Br | 2-Cl | 2.8(s, 6H), 3.1–3.3(m, 2H), 3.8–3.9(m, 2H), 4.3(m, 1H), 5.95(d, 1H), 6.7(d, 2H), 7.2–7.5(m, 3H), 7.6–7.7(d, 1H), 7.8(d, 1H), 8.2(s, 1H), 8.5(s, 1H) 9.25(s, 1H), 9.6–9.8(br s, 1H) | 492, 494, 496 |
| 55 | Br | 4-Cl, 2-F | 2.8(s, 6H), 3.1–3.3(m, 2H), 3.8–4.0(m, 2H), 4.3(m, 1H), 5.9(m, 1H), 6.7(d, 2H), 7.35(d, 2H), 7.5–7.6(m, 2H), 8.2(s, 1H), 8.7(s, 1H), 9.2(s, 1H), 9.7–9.9(br s, 1H) | 510, 512, 514 |
| 56 | Br | 4-Br, 2-F | 2.8(s, 6H), 3.05–3.2(m, 2H), 3.8–3.9(m, 2H), 4.2(br d, 1H), 5.8–6.0(br s, 1H), 6.7(d, 2H), 7.3(d, 2H), 7.4–7.5(m, 2H), 7.65(d, 1H), 8.2(s, 1H), 8.6(s, 1H), 9.15(s, 1H) | 554, 556, 558 |
| 57 | Br | 3-F | 2.8(s, 6H), 3.05–3.2(m, 2H), 3.9–4.0(m, 2H), 4.2–4.3(m, 1H), 5.9-(d, 1H), 6.8(d, 2H), 6.9(m, 1H), 7.3(m, 1H), 7.4–7.5(m, 2H), 7.65(d, 1H), 8.2(s, 1H), 8.6(s, 1H), 9.15(s, 1H), 9.7–9.8(br s, 1H) | 476, 478 |
| 58 | Br | 2-F, 4-Me | 2.8(s, 6H), 3.1–3.2(m, 2H), 3.8–3.9(m, 2H), 4.2(br s, 1H), 5.9(br s, 1H) 6.65(d, 2H) 7.0(d, 1H), 7.15(d, 1H), 7.35–7.4(m, 3H), 8.1(s, 1H), 8.45(s, 1H), 9.1(s, 1H) | 490, 492 |
| 59 | Br | 2,4-di-F | 2.8(S, 6H) 3.05–3.15(d, 2H), 3.8(m, 2H), 4.25(br s, 1H), 5.9(br d, 1H), 6.65(d, 2H), 7.05(t, 1H), 7.25(d, 2H), 7.3–7.6(m, 2H), 8.15(s, 1H), 8.6(s, 1H), 9.1(s, 1H), 9.7–9.8(br s, 1H) | 494, 496 |
| 60 | Br | 2,5-di-F | 2.8(s, 6H), 3.15–3.25(m, 2H), 3.8–4.0(m, 2H), 4.2(m, 1H), 5.9(d, 1H), 6.75(d, 2H), 7.1(m, 1H), 7.4(m, 3H), 7.6(m, 1H), 8.2(s, 1H), 8.5(s, 1H), 9.2(s, 1H), 9.7–9.8(br s, 1H) | 494, 496 |
| 61 | Br | 2,5-di-Me | 2.1(s, 3H), 2.3(s, 3H), 2.8(s, 6H), 3.1–3.3(m, 2H), 3.8–3.9(m, 2H), 4.2–4.3(m, 1H), 5.9(d, 1H), 6.6(d, 2H), 7.0(d, 1H), 7.2(m, 2H), 7.35–7.4(d, 2H), 8.05(s, 1H), 8.3(s, 1H), 9.05(s, 1H), 9.8(br s, 1H) | 486, 488 |
| 62[2] | Br | 3,4-CH=CH—NH—## | 2.2(s, 6H), 2.2–2.4(m, 2H), 3.7(m, 1H), 3.8(m, 2H), 4.7(d, 2H), 6.4(t, 1H), 6.6(d, 2H), 7.15(dd, 1H), 7.3–7.4(m, 3H), 7.7(d, 1H), 8.1(s, 1H), 8.4(s, 1H), 9.0(s, 1H), 11.05(br s, 1H) | 496, 498 |
| 63[2] | Br | 3,4-CH=CH—CH=N—^^ | 2.2(s, 6H), 2.2–2.45(m, 2H), 3.7(m, 1H), 3.85(m, 2H), 4.8(br s, 1H), 6.65(d, 2H), 7.4(d, 2H), 7.5(m, 1H), 7.95(q, 4H), 8.15(d, 1H), 8.2(s, 1H), 8.3(s, 1H), 8.8(m, 1H), 9.2(s, 1H) | 509, 511 |

-continued

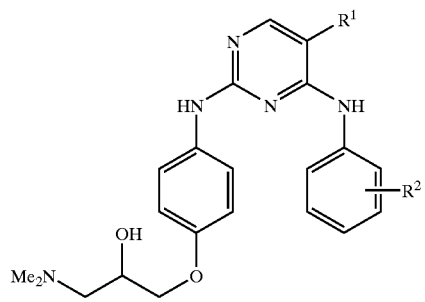

| Ex | R¹ | R² | NMR | MS (MH⁺) |
|---|---|---|---|---|
| 64 | Cl | 3-F | 2.8(s, 6H), 3.15–3.25(m, 2H), 3.9(m, 2H), 4.25(br s, 1H), 5.9(d, 1H), 6.8(d, 2H), 6.9(m, 1H), 7.35(m, 1H), 7.5(m, 3H), 7.7(d, 1H), 8.15(s, 1H), 8.9(s, 1H), 9.25(s, 1H), 9.8(br s, 1H) | 432, 434 |
| 65 | Cl | 4-F | 2.8(s, 6H), 3.15–3.2(m, 2H), 3.9(m, 2H), 4.3 (br s, 1H), 5.9(d, 1H), 6.8(d, 2H), 7.2(t, 2H), 7.5(d, 2H), 7.65(m, 2H), 8.1(s, 1H), 8.8(s, 1H), 9.15(s, 1H), 9.8(br s, 1H) | 432, 434 |
| 66 | Cl | 2,5-di-F | 2.9(s, 6H), 3.1–3.3(m, 2H), 3.9(m, 2H), 4.3 (br s, 1H), 6.0(br s, 1H), 6.8(m, 1H), 6.9(d, 2H), 7.2(m, 1H), 7.4(m, 1H), 7.5(d, 2H), 7.7 (m, 1H), 8.1(s, 1H), 8.8(s, 1H), 8.85(s, 1H), 9.9(br s, 1H) | 450, 452 |
| 67 | Cl | 4-MeO— | 2.8(s, 6H), 3.15–3.3(m, 2H), 3.75(s, 3H), 3.85 (m, 2H), 4, 25(br s, 1H), 5.9(d, 1H), 6.75(d, 2H), 6.9(d, 2H), 7.5(m, 4H), 8.05(s, 1H), 8.65 (s, 1H), 9.1(s, 1H), 9.8(br s, 1H) | 444, 446 |
| 68 | Cl | 4-ⁿBuOCH₂— | 0.9(t, 3H), 1.3(m, 2H), 1.5(m, 2H), 2.8(d, 6H), 3.1–3.3(m, 2H), 3.4(t, 2H), 3.9(m, 2H), 4.25(br s, 1H), 4.4(s, 2H), 5.9(br s, 1H), 5.9 (s, 1H), 6.8(d, 2H), 7.3(d, 2H), 7.5(d, 2H), 7.6 (d, 2H), 8.1(s, 1H), 8.8(s, 1H), 9.2(s, 1H), 9.8 (br s, 1H) | 500, 502 |
| 69³ | Br | 4-H₂NC(O)— | 2.81(dd, 6H), 3.15–3.30(m, 2H), 3.91(m, 2H), 4.28(m, 1H), 4.75(br s, 1H), 6.84(d, 2H), 7.30 (br s, 1H), 7.40(d, 2H), 7.68(d, 2H), 7.88(d, 2H), 7.98(br s, 1H), 8.31(s, 1H), 9.28(br s, 1H), 9.7–9.95(m, 2H) | 501.1, 503.2 |
| 70³ | Br | 4-OH | 2.81(dd, 6H), 3.15–3.30(m, 2H), 3.92(m, 2H), 4.27(m, 1H), 6.79(d, 2H), 6.81(d, 2H), 7.24 (d, 2H), 7.34(d, 2H), 8.29(s, 1H), 9.50(br s, 1H), 9.83(br s, 1H), 10.23(s, 1H) | 474.3, 476.3 |
| 71 | Br | 4-HOCH₂CH₂— | 2.18(s, 6H), 2.2–2.45(m, 2H), 2.72(t, 2H), 3.61(t, 2H), 3.75–3.9(m, 3H), 4.62(br s, 1H), 4.74(br s, 1H), 6.73(d, 2H), 7.18(d, 2H), 7.44 (d, 2H), 7.48(d, 2H), 8.12(s, 1H), 8.40(s, 1H), 9.06(s, 1H) | 502.3, 504.3 |
| 72 | Br | 3-HOCH₂— | 2.18(s, 6H), 2.2–2.4(m, 2H), 3.75–3.9(m, 3H), 4.50(d, 2H), 4.74(t, 1H), 5.15(m, 1H), 6.75 (d, 2H), 7.09(d, 1H), 7.30(dd, 1H), 7.44(d, 2H), 7.50(br s, 2H), 8.15(s, 1H), 8.44(s, 1H), 9.08(s, 1H) | 488.2, 490.2 |
| 73 | Br | 2-HOCH₂— | 2.18(s, 6H), 2.2–2.4(m, 2H), 3.75–3.9(m, 3H), 4.56(s, 2H), 4.74(d, 1H), 5.62(br s, 1H), 6.74 (d, 2H), 7.14(dd, 1H), 7.29(d, 1H), 7.34(dd, 1H), 7.43(d, 2H), 7.94(d, 1H), 8.17(s, 1H), 8.91(br s, 1H), 9.11(s, 1H) | 488.2, 490.2 |
| 74⁴ | Br | 4-H₂NSO₂— | 2.18(s, 6H), 2.2–2.4(m, 2H), 3.75–3.9(m, 3H), 4.75(br s, 1H), 6.80(d, 2H), 7.28(br s, 2H), 7.46(d, 2H), 7.74(d, 2H), 7.87(d, 2H), 8.13(s, 1H), 8.75(s, 1H), 9.20(s, 1H) | 537.2, 539.2 |
| 75 | Br | 4-CH₃C(O)NH— | 2.04(s, 3H), 2.18(s, 6H), 2.2–2.4(m, 2H), 3.75–3.9(m, 3H), 4.73(br s, 1H), 6.73(d, 2H), 7.4–7.55(m, 6H), 8.11(s, 1H), 8.43(s, 1H), 9.06(s, 1H), 9.91(s, 1H) | 515.2, 517.2 |
| 76⁵ | Br | 4-NH₂ | 2.18(s, 6H), 2.2–2.4(m, 2H), 3.75–3.9(m, 3H), 4.73(br s, 1H), 4.97(br s, 2H), 6.57(d, 2H), 6.70(d, 2H), 7.11(d, 2H), 7.44(d, 2H), 8.03(s, 1H), 8.17(s, 1H), 8.96(s, 1H) | 473.3, 475.3 |

-continued

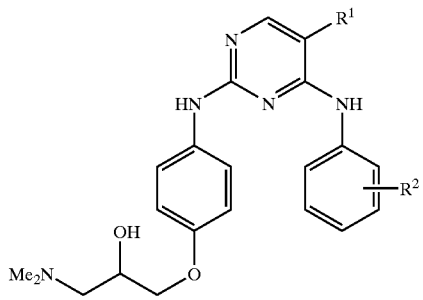

| Ex | R¹ | R² | NMR | MS (MH⁺) |
|---|---|---|---|---|
| 77[6] | Br | 4-(2-morpholino-ethoxy) | 2.18(s, 6H), 2.2–2.4(m, 2H), 2.45–2.5(m, 4H), 2.70(t, 2H), 3.55–3.6(m, 4H), 3.75–3.9(m, 3H), 4.10(t, 2H), 4.74(br s, 1H), 6.72(d, 2H), 6.93(d, 2H), 7.41(d, 2H), 7.43(d, 2H), 8.09(s, 1H), 8.39(s, 1H), 9.00(s, 1H) | 587.4, 589.4 |
| 78[7] | Br | 4-[2-(imidazol-1-yl)ethoxy] | 2.18(s, 6H), 2.2–2.45(m, 2H), 3.75–3.9(m, 3H), 4.25(t, 2H), 4.37(t, 2H), 4.91(br s, 1H), 6.70(d, 2H), 6.90(s, 1H), 6.92(d, 2H), 7.24(s, 1H), 7.40(d, 2H), 7.44(d, 2H), 7.69(s, 1H), 8.09(s, 1H), 8.40(s, 1H), 9.01(s, 1H) | 568.3, 570.3 |

[1] Isolated as dihydrochloride salt.
[2] Isolated as free base.
[3] Isolated as dihydrochloride salt which separated out from the reaction mixture.
[4] Bis-sulphonamide impurity precipitate removed by filtration from reaction mixture.
[5] Obtained as a by-product from Example 75 by evaporation of the less polar chromatography fractions.
[6] Starting 4-[2-(4-morpholino)ethoxy]aniline obtained as described in Eur. Pat. Appl. EP 401358.
[7] Starting 4-[2-(1-imidazolyl)ethoxy]aniline obtained as described in J. Med. Chem., 1985, 28, 1427.
**Such that R² and the phenyl ring to which it is attached forms 1H-indazol-5-yl.
Such that R² and the phenyl ring to which it is attached forms indol-5-yl.
^^Such that R² and the phenyl ring to which it is attached forms quinolin-6-yl.

EXAMPLES 79–85

The following compounds were prepared by an analogous method to that described in Example 1, using 4-[2-hydroxy-3-(N,N-dimethylamino)propoxy]aniline hydrochloride (Method 89) and the appropriate 5-substituted 4-anilino-2-chloropyrimidine intermediate (Methods 66–71, 73).

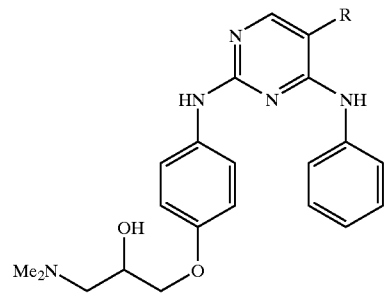

| Ex | R | NMR | MS (MH⁺) |
|---|---|---|---|
| 79 | (phenylpropanoyl) | 1.85–2.0(m, 2H), 2.6–2.75(t, 2H), 2.8–2.9(dd, 6H), 2.95–3.0(t, 2H), 3.15–3.35(m, 2H), 3.9–4.0(m, 2H), 4.3(m, 1H), 4.6–5.0(br s, 1H), 6.85–6.95(d, 2H), 7.15–7.4(m, 9H), 7.45–7.55(d, 2H), 7.55–7.75(br s, 2H), 8.9–9.0(bs, 1H), 9.8–10.0(br s, 1H) | 526 |

-continued

| Ex | R | NMR | MS (MH+) |
|---|---|---|---|
| 80 | (cyclopentyl-CH2CH2-C(=O)-CH2-) | 1.0–1.2(m, 2H), 1.4–1.7(m, 6H), 1.7–1.9(m, 3H), 2.2(s, 6H), 2.25–2.4(m, 2H), 2.95(t, 2H), 3.8–3.95(m, 3H), 4.8 (d, 1H), 6.85(d, 2H), 7.1(t, 1H), 7.35(t, 2H), 7.5–7.6(d, 2H), 7.6–7.8(br s, 2H), 8.9(s, 1H), 9.8(br s, 1H) | 504 |
| 81 | trans (PhCH=CH-) | 2.2(s, 6H), 2.2–2.4(m, 2H), 3.75–3.95(m, 3H), 4.7(br s, 1H), 6.7–6.8(d, 2H), 7.0–7.15(m, 2H), 7.2–7.4(m, 6H), 7.4–7.65(m, 6H), 8.4(s, 1H), 8.8(s, 1H), 9.1(s, 1H) | 482 |
| 82 | (4-F-C6H4-CH=CH-) | (s, 6H), 2.2–2.4(m, 2H), 3.8(m, 1H), 3.85–3.95(m, 2H), 4.75(br s, 1H), 6.8(d, 2H), 7.0–7.15(m, 2H), 7.2–7.25(t, 2H), 7.3–7.4(m, 3H), 7.5(d, 2H), 7.6–7.7(m, 4H), 8.4(s, 1H), 8.8(s, 1H), 9.1(s, 1H) | 500 |
| 83 | Ph | 2.1(s, 6H), 2.2–2.5(m, 2H), 3.7–3.95(3, H), 4.85(d, 1H), 6.8(d, 2H), 7.0(m, 1H), 7.25(t, 2H), 7.3–7.6(m, 10H), 7.9 (s, 1H), 8.1(s, 1H), 9.0(s, 1H) | 456 |
| 84 | (PhCH2CH2-) | 2.2(s, 6H), 2.25–2.4(m, 2H), 2.85(s, 2H), 3.25(s, 2H) 3.7–3.9(m, 3H), 4.7(d, 1H), 6.7(d, 2H), 7.0–7.1(t, 1H), 7.1–7.2 (m, 1H), 7.25–7.4(m, 6H), 7.5(d, 2H), 7.65(d, 2H), 7.8(s, 1H), 8.3(s, 1H), 8.75(s, 1H) | 484 |
| 85 | fur-3-yl | 2.8(m, 6H), 3.1–3.3(m, 2H), 3.9(m, 2H), 4.3(m, 1H), 6.8 (s, 1H), 6.85(d, 2H), 7.2(t, 1H), 7.3–7.4(m, 4H), 7.5(d, 2H), 7.8(s, 1H), 8.1(s, 2H), 9.4(s, 1H), 10.0(br s, 1H), 10.5–10.6(br s, 1H) | 446 |

EXAMPLE 86

4-Anilino-5-(ethoxymethyl)-2-{4-[2-hydroxy-3-(N,N-dimethylamino)propoxy]anilino}pyrimidine 4-[2-Hydroxy-3-(N,N-dimethylamino)propoxy]aniline hydrochloride (Method 89, 12.58 g, 44.5 mmol) was dissolved in boiling methanol (100 ml). The solution was added to a solution of 4-anilino-2-chloro-5-(ethoxymethyl) pyrimidine (Method 48; 13.01 g, 49.4 mmol) in n-butanol (400 ml) at 100° C. and the mixture was heated at 100° C. for 20 hours. Volatile material was removed by evaporation and the residue was dissolved in ethanol (400 ml). The solution was heated under reflux for 20 hours and then the solvent was removed by evaporation. The residue was dissolved in 10% methanol solution in DCM (50 ml), and loaded on a silica column. The column was eluted with 2–9% methanol solution in DCM containing 0.5% aqueous ammonia solution. Concentration of the appropriate fractions gave the product as a pale orange foam (17.6 g, 91%). NMR (CDCl$_3$): 1.28 (t, 3H), 2.33 (s, 6H), 2.3–2.6 (m, 2H), 3.54 (q, 2H), 3.97 (d, 2H), 4.07 (tt, 1H), 4.48 (s, 2H), 6.87 (d, 2H), 6.89 (s, 1H), 7.08 (t, 1H), 7.31 (dd, 2H), 7.44 (d, 2H), 7.57 (d, 2H), 7.87 (s, 1H), 7.93 (br s, 1H); MS (MH+): 438.5.

A sample of the di-hydrochloride salt of this example was also prepared. The free base (165 mg, 0.38 mmol) was dissolved in ethyl acetate/diethyl ether (1:3 v/v, 5 ml). Ethereal hydrogen chloride (1.0M; 1.2 ml, 1.2 mmol) was added. The precipitated solid was collected by filtration and washed with diethyl ether, giving the dihydrochloride salt as a hygroscopic solid (150 mg). NMR: 1.17 (t, 3H), 2.81 (dd, 2H), 3.1–3.3 (m, 2H), 3.56 (q, 2H), 3.94 (m, 2H), 4.28 (m, 1H), 4.38 (d, 1H), 4.49 (s, 2H), 6.88 (d, 2H), 7.23 (t, 1H), 7.32 (d, 2H), 7.37 (dd, 2H), 7.53 (d, 2H), 8.01 (s, 1H), 9.70 (br s, 1H), 9.97 (br s, 1H), 10.66 (s, 1H).

EXAMPLE 87

4-Anilino-5-(hydroxymethyl)-2-{4-[2-hydroxy-3-(N,N-dimethylamino)propoxy]anilino}pyrimidine 4-Anilino-5-(ethoxymethyl)-2-{4-[2-hydroxy-3-(N,N-dimethylamino)propoxy]anilino}pyrimidine dihydrochloride (Example 86; 50 mg, 0.11 mmol) was dissolved in water (3 ml) and the solution was heated under reflux for 3 hours. Volatile material was removed by evaporation and the residue was triturated with diethyl ether, giving the product as a hygroscopic dihydrochloride salt (35 mg, 75%). NMR: 2.81 (dd, 2H), 3.1–3.3 (m, 2H), 3.94 (m, 2H), 4.28 (m, 1H), 4.38 (d, 1H), 4.51 (s, 2H), 6.88 (d, 2H), 7.22 (t, 1H), 7.32 (d, 2H), 7.37 (dd, 2H), 7.56 (d, 2H), 7.93 (s, 1H), 9.91 (s, 1H) 9.91 (br s, 1H), 10.55 (s, 1H); MS (MH$^+$): 410.3.

EXAMPLE 88

4-Anilino-5-[(2-hydroxyethoxy)methyl]-2-{4-[2-hydroxy-3-(N,N-dimethylamino)propoxy]anilino}pyrimidine 4-Anilino-5-(ethoxymethyl)-2-{4-[2-hydroxy-3-(N,N-dimethylamino)propoxy]anilino}pyrimidine (Example 86, 70 mg, 0.16 mmol) was dissolved in ethylene glycol (2 ml). Ethereal hydrogen chloride (1.0M; 0.32 ml, 0.32 mmol) was added, and the solution was heated at 100° C. for 20 hours. Volatile material was removed by evaporation and the residue was triturated with diethyl ether, giving the product as a dihydrochloride salt (43 mg). NMR (CDCl$_3$): 2.34 (s, 6H), 2.3–2.6 (m, 2H), 3.63 (t, 2H), 3.73 (s, 1H), 3.86 (t, 2H), 3.96 (d, 2H), 4.08 (m, 1H), 4.54 (s, 2H), 6.86 (d, 2H), 6.88 (s, 1H), 7.08 (t, 1H), 7.30 (dd, 2H), 7.43 (d, 2H), 7.58 (d, 2H), 7.88 (m, 2H); MS (MH$^+$): 454.3.

EXAMPLES 89–92

The following compounds were prepared in by an analogous method to that described in Example 88, using 4-anilino-5-(ethoxymethyl)-2-{4-[2-hydroxy-3-(N,N-dimethylamino)propoxy]anilino}pyrimidine (Example 86) and the appropriate alcohol.

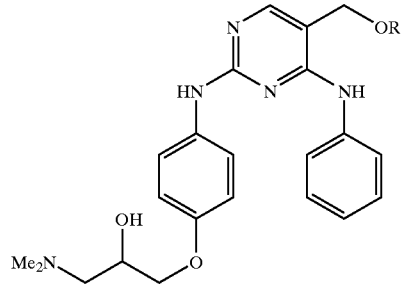

| Ex | R | NMR | MS (MH$^+$) |
|---|---|---|---|
| 89 | CH$_2$=CHCH$_2$— | 2.80(dd, 2H), 3.1–3.3(m, 2H), 3.92(m, 2H), 4.05(d, 2H), 4.28(m, 1H), 4.51(s, 2H), 5.18(d, 1H), 5.30(dd, 1H), 5.95(m, 1H), 6.86(d, 2H), 7.22(t, 1H), 7.32(d, 2H), 7.39(dd, 2H), 7.52(d, 2H), 8.01(s, 1H), 9.60(s, 1H), 9.93(br s, 1H), 10.53(s, 1H) | 450.4 |
| 90[1] | PhCH$_2$— | 2.81(dd, 2H), 3.1–3.3(m, 2H), 3.94(m, 2H), 4.28(m, 1H), 4.60(s, 4H), 6.87(d, 2H), 7.20–7.45(m, 10H), 7.56(d, 2H), 8.04(s, 1H), 9.69(s, 1H), 9.87(br s, 1H), 10.54(s, 1H) | 500.3 |
| 91 | cyclohexyl | 1.1–1.35(m, 4H), 1.4–1.75(m, 4H), 1.85–1.95(m, 2H), 2.81(dd, 2H), 3.1–3.3(m, 2H), 3.45(m, 1H), 3.94(m, 2H), 4.28(m, 1H), 4.54(s, 2H), 6.89(d, 2H), 7.21(t, 1H), 7.36(d, 2H), 7.37(dd, 2H), 7.55(d, 2H), 8.00(s, 1H), 9.50(s, 1H), 9.90(br s, 1H), 10.52(s, 1H) | 492.5 |
| 92[1] | HO(CH$_2$)$_4$— | 1.46(m, 2H), 1.57(m, 2H), 2.81(dd, 2H), 3.1–3.3(m, 2H), 3.40(t, 2H), 3.50(t, 2H), 3.95(m, 2H), 4.28(m, 1H), 4.58(s, 2H), 6.88(d, 2H), 7.23(t, 1H), 7.35(d, 2H), 7.38(dd, 2H), 7.52(d, 2H), 8.00(s, 1H), 9.79(s, 1H), 9.91(br s, 1H), 10.54(s, 1H) | 482.3 |

[1]Diethyl ether was added to the cooled reaction mixture, followed by ethanol until the mixture was homogeneous. The supernatant liquor was decanted off, and the oily residue triturated with ether to give the solid product.

EXAMPLE 93

4-Anilino-5-[(5-methylisoxazol-3-yl)oxymethyl]-2-{4-[2-hydroxy-3-(N,N-dimethylamino)propoxy]anilino}pyrimidine 4-Anilino-5-(ethoxymethyl)-2-{4-[2-hydroxy-3-(N,N-dimethylamino)propoxy]anilino}pyrimidine (Example 86, 100 mg, 0.23 mmol) was dissolved in NMP (2 ml). 3-Hydroxy-5-methylisoxazole (45 mg, 0.46 mmol) and ethereal hydrogen chloride (1.0M; 0.46 ml, 0.46 mmol) were added, and the solution was heated at 100° C. for 20 hours. Volatile material was removed by evaporation, and the residue was dissolved in 10% methanol solution in DCM (3 ml) and loaded on a Varian Mega Bond Elut column. The column was eluted with 0–2.5% methanol solution in DCM containing 0.5% aqueous ammonia solution. Concentration of the appropriate fractions and trituration of the residue with diethyl ether gave the product as a white crystalline solid (49 mg, 44%). NMR: 2.17 (s, 6H), 2.22 (s, 3H), 2.2–2.45 (m, 2H), 3.75–3.9 (m, 3H), 4.73 (br s, 1H), 4.49 (s, 2H), 5.78 (s, 1H), 6.80 (d, 2H), 7.02 (t, 1H), 7.30 (dd, 2H), 7.50 (d, 2H), 7.70 (d, 2H) 8.04 (s, 1H), 8.76 (s, 1H), 9.05 (s, 1H); MS (MH+): 491.5.

EXAMPLES 94–100

The following compounds were prepared by an analogous method to that described in Example 93 using 4-anilino-5-(ethoxymethyl)-2-{4-[2-hydroxy-3-N,N-dimethylamino)propoxy]anilino}pyrimidine (Example 86) and the appropriate heterocycle.

EXAMPLES 101–103

The following compounds were prepared by an analogous method to that described in Example 93, using 4-anilino-5-(ethoxymethyl)-2-{4-[2-hydroxy-3-N,N-dimethylamino)propoxy]anilino}pyrimidine (Example 86) and the appropriate amine hydrochloride salt.

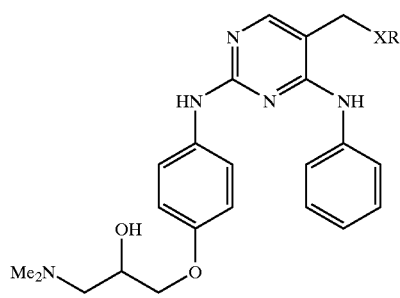

| Ex | X | R | NMR | MS (MH+) |
|---|---|---|---|---|
| 94 | O | isoxazol-3-yl | 2.20(s, 6H), 2.25–2.5(m, 2H), 3.75–3.9(m, 3H), 4.79 (br s, 1H), 5.06(s, 2H), 6.05(d, 1H), 6.80(d, 2H), 7.02(t, 1H), 7.29(dd, 2H), 7.50(d, 2H), 7.70(d, 2H), 8.05(s, 1H), 8.54(d, 1H), 8.73(s, 1H), 9.07(s, 1H) | 477.4 |
| 95[1] | NH | quinolin-6-yl | 2.81(dd, 2H), 3.1–3.3(m, 2H), 3.94(m, 2H), 4.28 (m, 1H), 4.57(s, 2H), 6.00(br s, 1H), 6.86(d, 2H), 7.13(s, 1H), 7.28(t, 1H), 7.35(d, 2H), 7.42(dd, 2H), 7.60(d, 2H), 7.66(d, 2H), 7.82(dd, 1H), 8.06(s, 1H), 8.17(d, 1H), 8.73(d, 1H), 8.80(d, 1H), 9.91(br s, 1H), 10.12(s, 1H) | 536.4 |
| 96 | NH | benzothien-6-yl | 2.18(s, 6H), 2.2–2.45(m, 2H), 3.75–3.9(m, 3H), 4.27 (d, 2H), 4.80(br s, 1H), 6.38(t, 1H), 6.76(d, 2H), 6.83(d, 1H), 6.95(d, 1H), 7.06(t, 1H), 7.24(s, 1H), 7.32(dd, 2H), 7.53(d, 2H), 7.67(d, 2H), 7.72(d, 1H), 7.78(d, 1H), 8.04(s, 1H), 8.38(s, 1H), 8.93(s, 1H) | 542.3 |
| 97 | NH | pyrazol-3-yl | 2.18(s, 6H), 2.2–2.4(m, 2H), 3.75–3.9(m, 3H), 4.18 (d, 2H), 4.72(d, 1H), 5.50(d, 1H), 5.68(t, 1H), 6.78 (d, 2H), 7.00(t, 1H), 7.27(dd, 2H), 7.54(d, 2H), 7.66 (d, 2H), 7.94(s, 1H), 11.58(d, 1H), 11.72(s, 1H) | 475.4 |
| 98[2] | NH | isoxazol-3-yl | 2.81(dd, 2H), 3.2–3.35(m, 2H), 3.94(m, 2H), 4.32 (m, 3H), 6.20(d, 1H), 6.87(d, 2H), 7.25(t, 1H), 7.34 (d, 2H), 7.39(dd, 2H), 7.60(d, 2H), 7.95(s, 1H), 8.45(s, 1H), 9.85(br s, 1H), 10.00(s, 1H), 10.51(s, 1H) | 476.2 |
| 99 | S | thiazol-2-yl | 2.18(s, 6H), 2.2–2.45(m, 2H), 3.75–3.9(m, 3H), 4.74 (d, 1H), 5.32(s, 2H), 6.78(d, 2H), 7.05(t, 1H), 7.13 (d, 1H), 7.31(dd, 2H), 7.50(d, 2H), 7.64(d, 1H), 7.67(d, 2H), 8.13(s, 1H), 8.63(d, 1H), 9.09(s, 1H) | 509.2 |
| 100 | S | tetrazol-5-yl | 2.76(s, 6H), 3.1–3.4(m, 2H), 3.90(m, 2H), 4.20(m, 1H), 4.28(s, 2H), 5.85(br s, 1H), 6.80(d, 2H), 7.20 (t, 1H), 7.29(dd, 2H), 7.58(d, 2H), 7.83(d, 2H), 7.97 (s, 1H), 8.95(s, 1H), 10.36(s, 1H) | 494.2 |

[1]Product isolated as trihydrochloride salt by filtration of the precipitate from cooled reaction mixture.
[2]Product isolated as dihydrochloride salt by evaporation of the reaction mixture and recrystallization of the residue twice from methanol/ether.

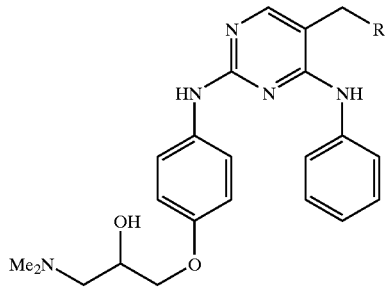

| Ex | R | NMR (CDCl$_3$) | MS (MH$^+$) |
|---|---|---|---|
| 101[1] | Me$_2$N— | 2.29(s, 6H), 2.3–2.6(m, 2H), 2.33(s, 6H), 3.37(s, 2H), 3.97(d, 2H), 4.08(m, 1H), 6.80(s, 1H), 6.88(d, 2H), 7.02(t, 1H), 7.30 (dd, 2H), 7.46(d, 2H), 7.57(d, 2H), 7.78(s, 1H), 9.88(s, 1H) | 437.4 |
| 102[2] | Et$_2$N— | 1.12(t, 6H), 2.33(s, 6H), 2.3–2.6(m, 2H), 2.59(q, 4H), 3.51(s, 2H), 3.97(d, 2H), 4.07(m, 1H), 6.78(s, 1H), 6.88(d, 2H), 7.02 (t, 1H), 7.30(dd, 2H), 7.46(d, 2H), 7.58(d, 2H), 7.78(s, 1H), 10.28(s, 1H) | 465.5 |
| 103[3] | MeNH— | 2.3–2.6(m, 2H), 2.33(s, 6H), 2.48(s, 3H), 2.59(t, 1H), 3.72(s, 2H), 3.97(d, 2H), 4.08(m, 1H), 4.56(s, 1H), 6.86(s, 1H), 6.87 (d, 2H), 7.02(t, 1H), 7.30(dd, 2H), 7.45(d, 2H), 7.58(d, 2H), 7.80(s, 1H), 9.92(s, 1H) | 423.4 |

[1]Reaction performed at 160° C. for 4 hours with DMF as solvent.
[2]Reaction performed at 160° C. for 3 hours.
[3]Reaction performed at 120° C. for 2 hours.

EXAMPLE 104

4-Anilino-5-(formamido)methyl-2-{4-[2-hydroxy-3-(N,N-dimethylamino)propoxy]anilino}pyrimidine 4-Anilino-5-(ethoxymethyl)-2-{4-[2-hydroxy-3-(N,N-dimethylamino)propoxy]anilino}pyrimidine (Example 86, 70 mg, 0.16 mmol) was dissolved in formamide (5 ml). Ethereal hydrogen chloride (1.0M; 0.19 ml, 0.19 mmol) was added, and the mixture was heated on power level 2 in a Toshiba Deltawave III domestic microwave oven (650 W) for 90 seconds. Excess formamide was removed by vacuum distillation and the residue was triturated with ethanol and diethyl ether, giving the product as a hygroscopic dihydrochloride salt (20 mg, 24%). NMR: 2.18 (s, 6H), 2.2–2.45 (m, 2H), 3.75–3.9 (m, 3H), 4.21 (d, 2H), 4.76 (br d, 1H), 6.79 (d, 2H), 7.01 (t, 1H), 7.29 (dd, 2H), 7.52 (d, 2H), 7.71 (d, 2H), 7.92 (s, 1H), 8.13 (d, 1H), 8.69 (t, 1H), 8.92 (s, 1H), 8.94 (s, 1H); MS (MH$^+$): 437.4.

EXAMPLE 105

4-Anilino-2-{4-[2-hydroxy-3-(N,N-dimethylamino)propoxy]anilino}-5-ureidomethyl-pyrimidine 4-Anilino-5-(ethoxymethyl)-2-{4-[2-hydroxy-3-(N,N-dimethylamino)propoxy]anilino}pyrimidine (Example 86, 70 mg, 0.16 mmol) was dissolved in 1,4-dioxane (2 ml). Urea (12 mg, 0.19 mmol) and ethereal hydrogen chloride (1.0M; 0.19 ml, 0.19 mmol) were added, and the suspension was heated at 100° C. for 20 hours. Diethyl ether (20 ml) was added, and the precipitated solid collected by filtration. The solid was dissolved in 10% methanol solution in DCM (3 ml), and loaded on a Varian Mega Bond Elut column. The column was eluted with 0–2.5% methanol solution in DCM containing 0.5% aqueous ammonia solution. Concentration of the appropriate fractions and trituration of the residue with diethyl ether gave the product as a white crystalline solid (20 mg, 28%). NMR: 2.18 (s, 6H), 2.2–2.45 (m, 2H), 3.75–3.9 (m, 3H), 4.07 (d, 2H), 4.74 (br d, 1H), 5.85 (s, 2H), 6.62 (t, 1H), 6.80 (d, 2H), 6.98 (t, 1H), 7.27 (dd, 2H), 7.54 (d, 2H), 7.77 (d, 2H), 7.88 (s, 1H), 8.88 (s, 1H), 9.88 (s, 1H); MS (MH$^+$): 452.4.

EXAMPLE 106

4-Anilino-2-{4-[2-hydroxy-3-(N,N-dimethylamino)propoxy]anilino}-5-(imidazol-1-ylmethyl)pyrimidine Using an analogous method to that described in Example 105, but starting from 4-anilino-5-(ethoxymethyl)-2-{4-[2-hydroxy-3-(N,N-dimethylamino)propoxy]anilino}pyrimidine (Example 86) and imidazole, the product was obtained in 25% yield. NMR: 2.18 (s, 6H), 2.2–2.45 (m, 2H), 3.75–3.9 (m, 3H), 4.76 (br s, 1H), 5.20 (s, 2H), 6.75 (d, 2H), 6.89 (d, 1H), 7.08 (t, 1H), 7.20 (d, 1H), 7.32 (dd, 2H), 7.50 (d, 2H), 7.61 (d, 2H), 7.78 (s, 1H), 7.96 (s, 1H), 8.54 (s, 1H), 9.00 (s, 1H); MS (MH$^+$): 460.4.

EXAMPLE 107

4-Anilino-5-carboxy-2-{4-[2-hydroxy-3-(N,N-dimethylamino)propoxy]anilino}pyrimidine 4-Anilino-S-ethoxycarbonyl-2-{4-[2-hydroxy-3-(N,N-dimethylamino)propoxy]anilino}pyrimidine (Method 1; 200 mg, 0.44 mmol) was suspended in ethanol (5 ml) and concentrated hydrochloric acid (2 ml), and the mixture was heated at 100° C. for 24 hours. Volatile material was removed by evaporation and the residue was triturated with isopropanol to give the product as a hydrochloride salt (50 mg, 25%). NMR: 2.8 (s, 6H), 3.2 (m, 2H), 3.9 (m, 2H), 4.2 (m, 1H), 6.9 (d, 2H), 7.1 (d, 2H), 7.15 (t, 1H), 7.13–7.7 (m, 8H), 8.7 (s, 1H), 10.0 (s, 1H), 10.55 (s, 1H); MS (MH$^+$): 424.

EXAMPLE 108

5-Amino-4-anilino-2-{4-[2-hydroxy-3-(N,N-dimethylamino)propoxy]anilino}pyrimidine 4-Anilino-2-{4-[2-hydroxy-3-(N,N-dimethylamino)propoxy]anilino}-5-nitropyrimidine (Example 20, 400 mg, 0.90 mmol) was dissolved in ethanol (20 ml). Under an atmosphere of nitrogen, cyclohexene (5 ml) was added followed by 10% palladium-on-carbon (100 mg). The mixture was heated under reflux for 5 hours, and then a further portion of 10% palladium on carbon (100 mg) was added and heating was continued for 18 hours. The catalyst was removed by filtration through diatomaceous earth and the filtrate was concentrated by evaporation. The resulting oil was purified by column chromatography, eluting with 0–10% 2.0M methanolic ammonia in DCM to give the product as a white solid (300 mg, 80%). NMR: 2.15 (s, 6H), 2.3 (m, 2H), 3.8 (m, 3H), 4.3 (s, 2H), 4.7 (s, 1H), 6.8 (d, 2H), 7.0 (t, 1H), 7.3 (t, 2H), 7.5 (d, 2H), 7.6 (s, 1H), 7.8 (d, 2H), 8.1 (s, 1H), 8.4 (s, 1H); MS (MH$^+$): 395.

EXAMPLE 109

4-Anilino-5-benzamido-2-{4-[2-hydroxy-3-(N,N-dimethylamino)propoxy]anilino}pyrimidine 5-Amino-4-anilino-2-{4-[2-hydroxy-3-(N,N-dimethylamino)propoxy]anilino}pyrimidine (Example 108; 100 mg, 0.25 mmol) and benzoic acid (30 mg, 0.25 mmol) were dissolved in DMF (3 ml). 4-N,N-dimethylaminopyridine (90 mg, 0.74 mmol) and 1-(3-N,N-dimethylaminopropyl-3-ethylcarbodiimide) hydrochloride (72 mg, 0.38 mmol) were added and the solution was stirred overnight. Silica (1 g) was added and volatile material was removed by evaporation. The residue was purified by column chromatography, eluting with 0–10% 2M methanolic ammonia in DCM. Concentration of the appropriate fractions gave the product as a solid (25 mg, 20%). NMR: 2.2 (s, 6H), 2.4 (m, 2H), 3.9 (m, 3H), 6.8 (d, 2H), 7.0 (t, 1H), 7.3 (t, 2H), 7.55 (m, 5H), 7.65 (d, 2H), 7.95 (s, 1H), 8.05 (d, 2H), 8.6 (s, 1H), 9.0 (s, 1H), 8.6 (s, 1H); MS (MH$^+$): 499.

EXAMPLE 110

Chiral separation of 4-anilino-5-bromo-2-{4-[2-hydroxy-3-(N,N-dimethylamino)propoxy]anilino}pyrimidine Racemic 4-anilino-5-bromo-2-{4-[3-(N,N-dimethyl)amino-2-hydroxypropoxy]anilino}pyrimidine (Example 3; 200 mg) was applied to a Chiralcel OJ column (Daicel Technologies Ltd; 250 cm×2 cm), mobile phase iso-hexane/isopropanol/triethylamine (60:40:0.1, flow rate 9 ml/min). The resolved enantiomers were isolated and the solvent was removed. Enantiomeric purities were determined using a Chiralcel OJ column (250 mm×4.6 mm), mobile phase isohexane/isopropanol/triethylamine (70:30:0.1, flow 1 mil/min, wavelength 254 nm). First eluted enantiomer (66 mg): retention time 23.27 minutes (analytical), 35 minutes (preparative). Second eluted enantiomer (67 mg): retention time 28.85 minutes (analytical), 43 minutes (preparative).

EXAMPLES 111–117

The following compounds were prepared by an analogous method to that described in Example 1 using 4-[2-hydroxy-3-(N,N-dimethylamino)propoxy]aniline hydrochloride (Method 89) and the appropriate 4-anilino-2-chloro-5-halopyrimidine intermediate (Methods 74–80).

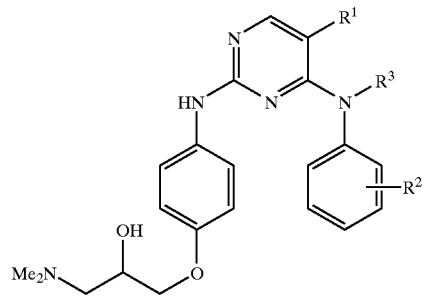

| Ex | R$^1$ | R$^2$ | R$^3$ | NMR (373K) | MS (MH$^+$) |
|---|---|---|---|---|---|
| 111 | Br | H | —(CH$_2$)$_3$CF$_3$ | 1.81(m, 2H), 2.21(m, 2H), 2.29(s, 6H), 2.49(m, 2H), 3.95(m, 5H), 6.88(d, 2H), 7.13(d, 2H), 7.19(t, 1H), 7.36(t, 2H), 7.48(d, 2H), 8.08(s, 1H), 8.81(s, 1H) | 568.5, 570.1 |
| 112 | Cl | H | —(CH$_2$)$_3$CF$_3$ | 1.84(m, 2H), 2.21(m, 8H), 2.35(m, 1H), 2.41(dd, 1H), 3.92(m, 5H), 4.30(bs, 1H), 6.87(d, 2H), 7.15(d, 2H), 7.20(t, 1H), 7.36(t, 2H), 7.48(d, 2H), 7.95(s, 1H), 8.78(s, 1H) | 524.4, 526.4 |
| 113 | Cl | 4-Br | —(CH$_2$)$_3$CF$_3$ | 1.81(m, 2H), 2.21(m, 8H), 2.34(m, 1H), 2.41(dd, 1H), 3.91(m, 5H), 4.29(bs, 1H), 6.86(d, 2H), 7.11(d, 2H), 7.47(d, 2H), 7.51(d, 2H), 8.00(s, 1H), 8.85(s, 1H) | 602.4, 604.4, 606.4 |
| 114 | Cl | 4-Br | —CH$_2$CH=CHBr | 2.21(s, 6H), 2.38(m, 1H), 2.44(dd, 1H), 3.90(m, 3H), 4.30(bs, 1H), 4.50(s, 1H), 4.64(s, 1H), 6.39(s, 1H), 6.49(s, 1H), 6.86(t, 2H), 7.10(q, 2H), 7.50(m, 4H), 8.02(s, 1H), 8.90(s, 1H) | 610.3, 612.3, 614.3 |

-continued

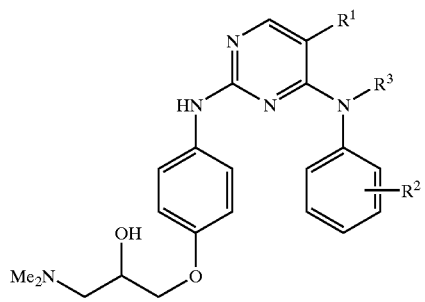

| Ex | R¹ | R² | R³ | NMR (373K) | MS (MH⁺) |
|---|---|---|---|---|---|
| 115 | Cl | 2-F, 5-Me | —CH₂CH=CHPh | 2.20(s, 6H), 2.26(s, 3H), 2.32(m, 1H), 2.40(dd, 1H), 3.85(m, 3H), 4.29(bs, 1H), 4.64(d, 2H), 6.37(m, 1H), 6.45(d, 1H), 6.82(d, 2H), 7.08(d, 2H), 7.19(m, 2H), 7.26(d, 4H), 7.50(d, 2H), 7.96(s, 1H), 8.85(bs, 1H) | 562.5, 564.5 |
| 116 | Cl | H | Me | (293K) 2.15(s, 6H), 2.3(m, 2H), 3.4(s, 3H), 3.9(m, 3H), 4.7(d, 1H), 6.85(d, 2H), 7.2(m, 3H), 7.4(t, 2H), 7.6(d, 2H), 8.0(s, 1H), 9.3(s, 1H) | 428, 430 |
| 117 | Br | H | Me | (293K) 2.2(s, 6H), 2.3(m, 2H), 3.4(s, 3H), 3.85(m, 3H), 4.8(d, 1H), 6.8(d, 2H), 7.2(m, 3H), 7.35(t, 2H), 7.6(d, 2H), 8.1(s, 1H), 9.4(s, 1H)² | 472, 474 |

EXAMPLES 118–120

The following compounds were prepared by an analogous method to that described in Example 1 using 4-[2-hydroxy-3-(N,N-dimethylamino)propoxy]aniline hydrochloride (Method 89) and the appropriate ²-chloro-5-halo-4-(2-pyridylamino) pyrimidine intermediate (Methods 81–83).

4-dichloropyrimidine, the appropriate substituted 2-aminopyridine and 4-[2-hydroxy-3-(N,N-dimethylamino)propoxy]aniline hydrochloride (Method 89).

| Ex | R¹ | R² | NMR | MS (MH⁺) |
|---|---|---|---|---|
| 118 | Br | H | 2.1(s, 6H), 2.5(m, 2H), 3.7–4.0(m, 3H), 4.8(s, 1H), 6.9(d, 2H), 7.1(t, 1H), 7.5(t, 1H), 8.1–8.4 (m, 4H), 9.3(s, 1H) | 459, 461 |
| 119 | Cl | Me | 2.2(s, 6H), 2.3(m, 2H), 2.4(s, 3H), 3.9(m, 3H), 4.8(d, 1H), 6.9(d, 2H), 7.0(d, 1H), 7.5(d, 2H), 7.6(t, 1H), 8.0(m, 1H), 8.2(s, 1H), 8.3(s, 1H), 9.3(s, 1H) | 429, 431 |
| 120 | Cl | H | 2.2(s, 6H), 2.3(m, 2H), 3.9(m, 3H), 4.8(d, 1H), 6.8(d, 2H), 7.1(m, 1H), 7.5(d, 2H), 7.8(m, 1H), 8.2(m, 2H), 8.35(d, 1H), 8.45(s, 1H), 9.3(s, 1H) | 415, 417 |

EXAMPLES 121–124

The following compounds were prepared by an analogous method to that described in Example 44 using 5-bromo-2,

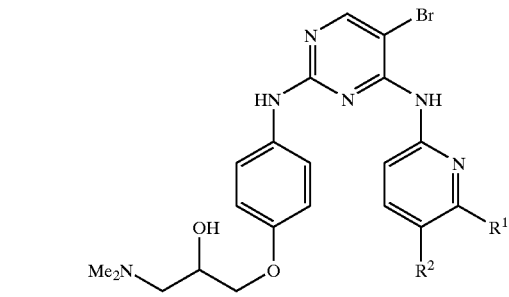

| Ex | R¹ | R² | NMR | MS (MH⁺) |
|---|---|---|---|---|
| 121¹ | H | Br | 2.8(s, 6H), 3.3(m, 2H), 3.95(m, 2H), 4.2(m, 1H), 6.9(d, 2H), 7.5(d, 2H), 7.9(m, 1H), 8.2(m, 3H), 8.4(s, 1H)² | 538, 540, 542 |
| 122 | H | Cl | (CD₃CO₂D) 2.8(s, 6H), 3.3(m, 2H), 3.95(m, 2H), 4.3(m, 1H), 6.9(d, 2H), 7.5(d, 2H), 7.8(d, 1H), 8.3(m, 2H), 8.4(s, 1H) | 493, 495, 497 |
| 123 | H | Me | 2.3(s, 3H), 2.8(s, 6H), 3.2(m, 2H), 3.9(m, 2H), 4.25(m, 1H), 5.85(s, 1H), 6.9(d, 2H), 7.5(d, 2H), 7.6(d, 1H), 8.1(m, 2H), 8.2(s, 1H), 8.25(s, 1H), 9.3(s, 1H) | 473, 475 |
| 124 | Me | H | 2.35(s, 6H), 2.4(s, 3H), 2.6(m, 2H), 3.8–4.0(m, 3H), 6.8(d, 2H), 7.0(d, 1H), 7.5(d, 2H), 7.7(t, 1H), 8.0(m, 2H), 8.3(s, 1H), 9.3(s, 1H) | 473, 475 |

¹Isolated as a hydrochloride salt

EXAMPLES 125–126

The following compounds were prepared by an analogous method to that described in Example 1, using 4-[2-hydroxy- 3-(N,N-dimethylamino)propoxy]aniline hydrochloride (Method 89) and the appropriate 5-bromo-2-chloro-4-(3-pyridylamino)pyrimidine intermediate (Methods 85–86).

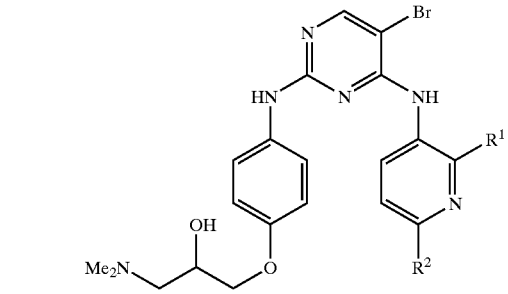

| Ex | R¹ | R² | NMR | MS (MH⁺) |
|---|---|---|---|---|
| 125 | NH₂ | H | 2.15(s, 6H), 2.3(m, 2H), 3.7(m, 1H), 3.9(m, 2H), 4.7(s, 1H), 5.6(s, 2H), 6.6(m, 3H), 7.4(m, 3H), 7.9(d, 1H), 8.1(d, 2H), 9.0(s, 1H) | 474, 476 |
| 126 | H | MeO— | 2.2(s, 6H), 2.3(m, 2H), 3.9(m, 1H), 3.85(m, 5H), 4.8(s, 1H), 6.7(d, 2H), 6.8(d, 1H), 7.4(d, 2H), 7.8(m, 1H), 8.1(s, 1H), 8.3(s, 1H), 8.6(s, 1H), 9.1(s, 1H) | 489, 491 |

EXAMPLES 127–132

The following compounds were prepared by an analogous method to that described in Example 44 using 5-bromo-2,4-dichloropyrimidine, the appropriate substituted 3-aminopyridine and 4-[2-hydroxy-3-(N,N-dimethylamino)propoxy]aniline hydrochloride.

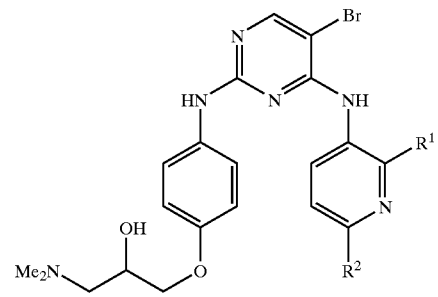

| Ex | R¹ | R² | NMR | MS (MH⁺) |
|---|---|---|---|---|
| 127¹ | H | Cl | 2.6(s, 6H), 2.9(m, 2H), 3.9(m, 2H), 4.15(m, 1H), 6.8(d, 2H), 7.45(m, 3), 8.1(m, 1H), 8.2(s, 1H), 8.7(s, 1H), 8.85(s, 1H), 9.15(s, 1H) | 493, 495, 497 |
| 128¹ | Cl | H | 2.8(s, 6H), 3.2(m, 2H), 3.85(m, 2H), 4.2(m, 1H), 5.9(s, 1H), 6.7(d, 2H), 7.3(d, 2H), 7.5(m, 1H), 8.2(m, 1H), 8.3(m, 1H), 8.6(s, 1H), 9.3(s, 1H) | 493, 495, 497 |
| 129 | MeO— | MeO— | 2.4(s, 6H), 2.6(m, 2H), 3.7–3.8(m, 8H), 4.0(m, 1H), 6.4(d, 1H), 6.7(d, 2H), 7.4(d, 2H), 7.9(d, 1H), 8.0(s, 1H), 8.1(s, 1H), 9.1(s, 1H) | 519, 521 |
| 130 | Me | Me | 2.3(s, 3H), 2.5(s, 3H), 2.7(s, 6H), 3.0(m, 2H), 3.8(m, 2H), 4.2(m, 1H), 5.7(s, 1H), 6.6(d, 2H), 7.1(d, 1H), 7.3(d, 2H), 7.6(d, 1H), 8.1(s, 1H), 8.5(s, 1H), 9.05(s, 1H) | 487, 489 |
| 131 | H | Me | 2.3(s, 6H), 2.35–2.5(5H), 3.8(m, 1H), 3.9(m, 2H), 6.7(d, 2H), 7.2(d, 1H), 7.4(d, 2H), 7.9(m, 1H), 8.15 (s, 1H), 8.6(s, 2H), 9.1(s, 1H) | 473, 475 |
| 132 | H | Br | 2.2(s, 6H), 2.4(m, 2H), 3.8(m, 1H), 3.9(m, 2H), 4.8(s, 1H), 6.6(d, 2H), 7.4(d, 2H), 7.6(d, 1H), 8.1(m, 1H), 8.2(s, 1H), 8.7(s, 1H), 8.8(s, 1H), 9.2(s, 1H) | 539, 541 |

¹Isolated as a hydrochloride salt.

EXAMPLE 133

5-Bromo-4-(2-bromo-6-methylpyrid-4-yl)amino-2-{4-[2-hydroxy-3-(N,N-dimethylamino)propoxy]anilino}pyrimidine Using an analogous method to that described in Example 44, but starting from 4-amino-2-bromo-6-methylpyridine, the product was obtained. NMR: 2.3 (s, 3H), 2.8 (s, 6H), 3.2 (m, 2H), 3.8 (m, 3H), 5.8 (mn, 1H), 6.9 (d, 2H), 7.2 (s, 1H), 7.5 (d, 2H), 7.8 (s, 1H), 8.3 (s, 1H), 9.5 (s, 1H); MS (MH⁺): 551, 553, 555.

EXAMPLES 134–135

The following compounds were prepared by an analogous method to that described in Example 1 using 4-[2-hydroxy-3-(N,N-dimethylamino)propoxy]aniline hydrochloride and the appropriate 4-substituted 5-bromo-2-chloropyrimidine intermediate (Methods 87–88).

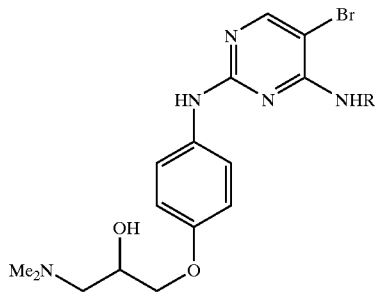

| Ex | R | NMR | MS (MH+) |
|---|---|---|---|
| 134 | 4-methyl-thiazol-2-yl | 2.2(m, 9H), 2.3(m, 2H), 3.9(m, 3H), 4.8(s, 1H), 6.6(s, 1H), 6.9(d, 2H), 7.5(d, 2H), 8.2(s, 1H), 9.0(s, 1H) | 479, 481 |
| 135 | 5-methyl-pyrazol-3-yl | 2.1–2.5(m, 11H), 3.9(m, 3H), 4.8(s, 1H), 6.35(s, 1H), 6.9(m, 2H), 7.5(d, 2H), 8.2(m, 2H), 9.1(s, 1H), 12.1 (s, 1H) | 462, 464 |

EXAMPLE 136

4-Anilino-5-chloro-2-{4-[2-hydroxy-3-(isopropylamino)propoxy]anilino}pyrimidine

4-Anilino-2,5-dichloropyrimidine (Method 7, 241 ma, 1.0 mmol) was dissolved in n-butanol (20 ml) and methanol (4 ml). 4-[2-Hydroxy-3-(isopropylamino)propoxy]aniline (obtained as described in Pharmazie 1980, 35, 278; 202 mg, 0.9 mmol) and ethereal hydrogen chloride (1.0M; 2 ml, 2.0 mmol) were added and the solution was heated at 100° C. for 20 hours, allowed to cool to ambient temperature and then concentrated to a volume of 5 ml. The solution was loaded on a Varian Mega Bond Elut column and the column was eluted with 0–4% 2.0M methanolic ammonia solution in DCM. Concentration of the appropriate fractions and recrystallization of the residue from acetonitrile gave the product as a white solid (159 mg, 41%). NMR: 1.0 (d, 6H), 2.5–2.6 (m, 1H), 2.65–2.75 (m, 2H), 3.8–3.95 (m, 3H), 4.9 (br s, 1H), 6.8 (d, 2H), 7.1 (t, 1H), 7.35 (t, 2H), 7.45 (d, 2H), 7.65 (d, 2H), 8.1 (s, 1H), 8.7 (s, 1H), 9.1 (s, 1H); MS (MH+): 428, 430.

EXAMPLES 137–150

The following compounds were prepared by an analogous method to that described in Example 136 using 4-[2-hydroxy-3-(isopropylamino)propoxy]aniline (Pharmazie 1980, 35, 278) and the appropriate 5-substituted 4-anilino-2-chloropyrimidine intermediate (Methods 12–13, 15, 20, 43, 49–56).

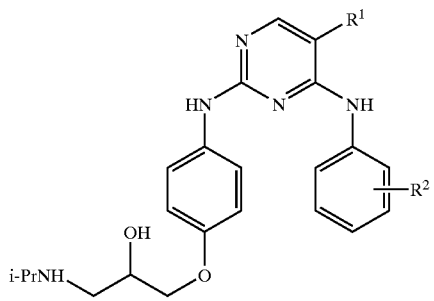

| Ex | R1 | R2 | NMR/HPLC | MS (MH+) |
|---|---|---|---|---|
| 137 | Br | H | RT: 2.87 | 472, 474 |
| 138 | Br | 2,4-di-F | 1.3(m, 6H), 2.9(m, 1H), 3.1(m, 1H), 3.3(m, 1H), 3.9 (m, 2H), 4.2(m, 1H), 6.7(m, 2H), 7.1–7.3(m, 3H), 7.5 (m, 2H), 8.3(s, 1H), 8.6(m, 1H), 8.9(m, 1H), 9.3(s, 1H), 9.9(m, 1H) | 508, 510 |

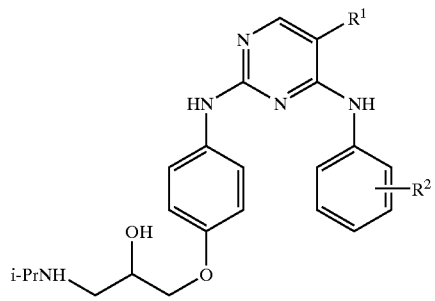

| Ex | R¹ | R² | NMR/HPLC | MS (MH⁺) |
|---|---|---|---|---|
| 139 | Br | 3,4-(CH$_2$)$_3$—** | 1.0(m, 6H), 2.0(m, 2H), 2.5–2.7(m, 3H), 2.8(m, 4H), 3.8(m, 3H), 6.7(m, 2H), 7.2(m, 1H), 7.3(m, 1H), 7.4 (m, 3H), 8.1(s, 1H), 8.3(s, 1H), 9.0(s, 1H) | 512, 514 |
| 140 | Br | 4-OMe | 1.3(m, 6H), 2.9(m, 1H), 3.1(m, 1H), 3.3(m, 1H), 3.8 (s, 3H), 3.9(m, 2H), 4.2(m, 1H), 6.8(m, 2H), 7.0(m, 2H), 7.3–7.4(m, 4H), 8.3(s, 1H), 8.6(m, 1H), 8.9(m, 1H), 9.5(s, 1H), 9.9(m, 1H) | 502, 504 |
| 141 | Me | H | 1.0(d, 6H), 2.1(s, 3H), 2.5–2.6(m, 1H), 2.6–2.75(m, 2H), 3.75–3.9(m, 3H), 4.85(br s, 1H), 6.95(d, 2H), 7.0 (t, 1H), 7.3(t, 2H), 7.55(d, 2H), 7.7(d, 2H), 7.8(s, 1H), 8.2(s, 1H), 8.7(s, 1H) | 408.2 |
| 142 | Br | 2-HOCH$_2$— | 0.96(d, 6H), 2.4–2.75(m, 3H), 3.75–3.9(m, 3H), 4.54 (s, 2H), 4.87(br s, 1H), 5.64(br s, 1H), 6.74(d, 2H), 7.13(dd, 1H), 7.30(dd, 1H), 7.34(d, 1H), 7.43(d, 1H), 7.93(d, 1H), 8.16(s, 1H), 8.91(br s, 1H), 9.11(s, 1H) | 502.2, 504.2 |
| 143 | Br | 4-HOCH$_2$— | 0.97(d, 6H), 1.50(br s, 1H), 2.4–2.75(m, 3H), 3.75–3.9(m, 3H), 4.48(s, 2H), 4.87(br s, 1H), 5.14(br s, 1H), 6.74(d, 2H), 7.27(d, 2H), 7.44(d, 2H), 7.53(d, 2H), 8.14(s, 1H), 8.43(s, 1H), 9.07(s, 1H) | 502.5, 504.5 |
| 144 | Br | 4-F | 0.97(d, 6H), 2.5–2.7(m, 2H), 2.65–2.75(m, 1H), 3.76–3.91(m, 3H), 4.85(br s, 1H), 6.74(d, 2H), 7.17(dd, 2H), 7.41(d, 2H), 7.60(dd, 2H), 8.14(s, 1H), 8.53(s, 1H), 9.08(s, 1H) | 490.1, 492.1 |
| 145[1] | CN | H | 0.97(d, 6H), 2.4–2.75(m, 3H), 3.75–3.9(m, 3H), 4.88 (br s, 1H), 6.76(br d, 2H), 7.14(t, 1H), 7.34(dd, 2H), 7.44(d, 2H), 7.55(br d, 2H), 8.04(s, 1H), 9.40(br s, 1H), 9.71(br s, 1H) | 419.4 |
| 146 | Br | 3,4-di-F | RT: 4.07 | 508, 510 |
| 147 | Br | 3-Me | RT: 3.30 | 486, 488 |
| 148 | Cl | 4-F | 0.97(d, 6H), 2.5–2.7(m, 2H), 2.65–2.75(m, 1H), 3.76–3.91(m, 3H), 4.85(br s, 1H), 6.76(d, 2H), 7.28(dd, 2H), 7.43(d, 2H), 7.64(dd, 2H), 8.07(s, 1H), 8.79(s, 1H), 9.09(s, 1H) | 446, 448 |
| 149 | Br | 4-Br | RT: 4.68 | 551, 553 |
| 150 | Br | 3-F | RT: 3.20 | 490, 492 |

[1]Prepared from 4-anilino-5-cyano-2-(methanesulphonyl)pyrimidine (Method 64).
**Such that R² and the phenyl ring to which it is attached forms indan-5-yl.

EXAMPLES 151–154

The following compounds were prepared by an analogous method to that described in Example 136 using 4-[2-hydroxy-3-(isopropylamino)propoxy]aniline (Pharmazie 1980, 35, 278), and the appropriate 2-chloro-5-halo-4-(2-pyridylamino)pyrimidine (Methods 81–84).

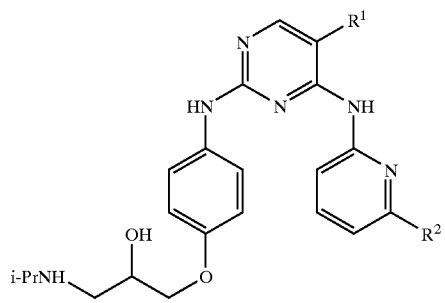

| Ex | R¹ | R² | NMR | MS (MH⁺) |
|---|---|---|---|---|
| 151 | Br | Me | 0.9(s, 3H), 0.95(s, 3H), 2.4(s, 3H), 2.55(m, 1H), 2.8(m, 2H), 3.8(m, 3H), 4.95(s, 1H), 6.9(d, 2H), 7.0(d, 1H), 7.5(d, 2H), 2.7 (t, 1H), 8.1(s, 2H), 8.3(s, 1H), 9.3(s, 1H) | 487, 489 |
| 152 | Br | H | 0.9(s, 3H), 0.95(s, 3H), 2.5(m, 1H), 2.7(m, 2H), 3.9(m, 3H), 4.9(s, 1H), 6.8(d, 2H), 7.1(t, 1H), 7.5(d, 2H), 7.8(t, 1H), 8.2(s, 2H), 8.3(s, 1H), 8.35(d, 1H), 9.4(s, 1H) | 473, 475 |
| 153 | Cl | H | 0.95(s, 3H), 1.0(s, 3H), 2.5(m, 1H), 2.7(m, 2H), 3.8(m, 3H), 4.9(s, 1H), 6.85(d, 2H), 7.1(t, 1H), 7.5(d, 2H), 7.8(t, 1H), 8.2 (m, 2H), 8.35(d, 1H), 9.3(s, 1H) | 429, 431 |
| 154 | Cl | Me | 0.95(s, 3H), 1.0(s, 3H), 2.4(s, 3H), 2.55(m, 1H), 2.7(m, 2H), 3.8(m, 3H), 4.9(s, 1H), 6.8(d, 2H), 7.0(d, 1H), 7.5(d, 2H), 7.65 (t, 1H), 8.0(m, 1H), 8.2(s, 1H), 9.3(s, 1H) | 443, 445 |

EXAMPLES 155–158

The following compounds were prepared by an analogous method to that described in Example 136 using 4-[3-(t-butylamino)-2-hydroxypropoxy]aniline (obtained as described in Pharmazie, 1980, 35, 278) and the appropriate 2-chloro-5-halo-4-(2-pyridylamino) pyrimidine intermediate.

EXAMPLES 159–161

The following compounds were prepared by an analogous method to that described in Example 136, using the appropriate substituted aniline and the appropriate 4-substituted 5-bromo-2-chloropyrimidine intermediate.

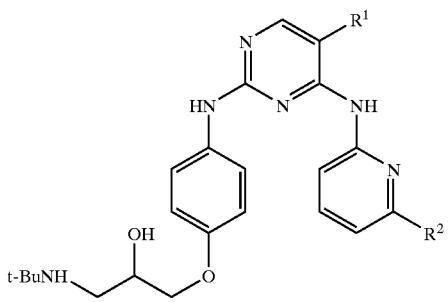

| Ex | R¹ | R² | NMR | MS (MH⁺) |
|---|---|---|---|---|
| 155 | Br | H | 0.9(s, 9H), 2.5(m, 2H), 3.8(m, 3H), 4.8(s, 1H), 6.9(d, 2H), 7.1 (t, 1H), 7.5(d, 2H), 7.8(t, 1H), 8.2(m, 2H), 8.3(s, 1H), 8.4(d, 1H), 9.3(s, 1H) | 487, 489 |
| 156 | Br | Me | 1.1(s, 9H), 2.4(s, 3H), 2.7 m, 1H), 2.9(m, 1H), 3.9(m, 3H), 6.9 (d, 2H), 7.0(d, 1H), 7.5(d, 2H), 7.65(t, 1H), 8.0(m, 2H), 8.25(s, 1H), 9.3(s, 1H) | 501, 503 |
| 157 | Cl | H | 1.0(s, 9H), 2.6(m, 2H), 3.8(m, 3H), 4.8(s, 1H), 6.8(d, 2H), 7.1 (t, 1H), 7.6(d, 2H), 7.8(t, 1H), 8.1(m, 2H), 8.3(d, 1H), 9.3(s, 1H) | 443, 445 |
| 158 | Cl | Me | 1.1(s, 9H), 2.4(s, 3H), 2.6(m, 2H), 3.9(m, 3H), 4.9(s, 1H), 6.8 (d, 2H), 7.0(d, 2H), 7.5(d, 2H), 7.65(t, 1H), 8.0(d, 1H), 8.2(s, 1H), 9.3(s, 1H) | 457, 459 |

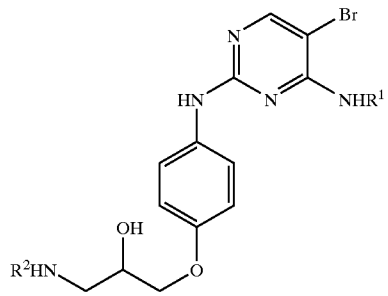

| Ex | R¹ | R² | NMR | MS (MH⁺) |
|---|---|---|---|---|
| 159 | 4-methyl-thiazol-2-yl | i-Pr | 0.95(s, 3H), 1.0(s, 3H), 2.2(s, 3H), 2.55(m, 1H), 2.7(m, 2H), 3.9(m, 3H), 6.6(s, 1H), 6.9(d, 2H), 7.5(d, 2H), 8.2(s, 1H), 9.0(s, 1H) | 493, 495 |
| 160 | 5-methyl-pyrazol-3-yl | i-Pr | 0.95(s, 3H), 1.0(s, 3H), 2.2(s, 3H), 2.55(m, 1H), 2.7(m, 2H), 3.8(m, 3H), 4.9(s, 1H), 6.35(s, 1H), 6.8(d, 2H), 7.5(d, 2H), 8.2(m, 2H), 9.1(s, 1H), 12.1(s, 1H) | 476, 478 |
| 161 | 5-methyl-pyrazol-3-yl | t-Bu | 1.0(s, 9H), 2.2(s, 3H), 2.6(m, 2H), 3.9(m, 3H), 6.3(s, 1H), 6.8(d, 2H), 7.5(d, 2H), 8.1(s, 1H), 8.2(s, 1H), 9.1(s, 1H), 12.1(1H) | 490, 492 |

EXAMPLES 162–178

The following compounds were prepared by an analogous method to that described in Example 136, using the appropriate substituted aniline (Methods 91–101) and the appropriate 4-anilino-5-bromo-2-chloropyrimidine.

| Ex | R¹ | R² | R³ | MS (MH⁺) | HPLC (RT) |
|---|---|---|---|---|---|
| 162 | H | PhCH₂— | i-Pr | 562, 564 | 6.25 |
| 163 | MeO— | CH₂=CHCH₂— | Me | 514, 516 | 3.06 |
| 164 | MeO— | i-Bu | H | 516, 518 | 3.33 |
| 165 | MeO— | cyclopentyl | H | 529, 531 | 3.48 |
| 166 | MeO— | pyrrolidino | | 515, 517 | 3.76 |
| 167 | H | cyclopentyl | H | 499, 501 | 3.57 |
| 168 | H | i-Bu | H | 486, 488 | 4.10 |
| 169 | MeO— | Me | H | 474, 476 | 3.00 |
| 170 | H | pyrrolidino | | 485, 487 | 3.89 |
| 171 | H | Me | H | 444, 446 | 2.70 |
| 172 | H | H | H | 430, 432 | 2.33 |
| 173 | MeO— | H | H | 460, 462 | 3.59 |
| 174 | H | Et | H | 458, 460 | 2.99 |
| 175 | MeO— | Et | H | 488, 490 | 3.17 |
| 176 | H | morpholino | | 500, 502 | 2.89 |
| 177 | H | 4-acetylpiperazin-1-yl | | 541, 543 | 2.88 |
| 178 | MeO— | 4-methylpiperazin-1-yl | | 543, 545 | 2.18 |

EXAMPLES 179–180

The following compounds were prepared by an analogous method to that described in Example 136, using the appropriate substituted aniline (obtained as described in Pharmazie, 1980, 35, 278) and 4-anilino-5-bromo-2-chloropyrimidine (Method 13).

| Ex | X | R | MS (MH⁺) | HPLC (RT) |
|---|---|---|---|---|
| 179 | 3-O | i-Pr | 472, 474 | 4.19 |
| 180 | 4-O | t-Bu | 486, 488 | 4.38 |

EXAMPLE 181

4-Anilino-5-bromo-2-{4-[2-hydroxy-3-(4-methylpiperazin-1-yl)propoxy]anilino}pyrimidine A mixture of potassium carbonate (160 mg, 1.1 mmol), epibromohydrin (0.14 ml, 1.7 mmol) and 4-anilino-5-bromo-2-(4-hydroxyanilino)pyrimidine (Method 4, 200 mg, 0.56 mmol) in DMSO (2 ml) was stirred for 12 hours. 1-Methylpiperazine (0.62 ml) was added dropwise and the resulting solution was stirred for a further 12 hours. Silica (1 g) was added and volatile material was removed by evaporation. The residue was loaded onto a Varian Mega Bond Elut column and the column was eluted with 50:50 isohexane: DCM (2×20 ml), DCM (2×20 ml), 2% 2M NH₃/MeOH/DCM (2×20 ml), 4% 2M NH₃/MeOH/DCM (2×20 ml), 6% 2M NH₃/MeOH/DCM (2×20 ml) and 10% 2M NH₃/MeOH/DCM (8×20 ml). Concentration of the appropriate fractions gave the product as a yellow gum (87 mg, 30%). MS (MH⁺): 513, 515; HPLC (RT): 1.85.

EXAMPLE 182

4-Anilino-5-bromo-2-{3-[2-hydroxy-3-(4-methylpiperazin-1-yl)propoxy]anilino}pyrimidine Using an analogous procedure to that described in Example 181, but starting from 4-anilino-5-bromo-2-(3-hydroxyanilino)pyrimidine (Method 6), the title product was obtained. MS (MH$^+$): 513, 515; HPLC (RT): 2.00.

EXAMPLE 183

4-Anilino-5-bromo-2-{4-[3-(4-methylpiperazin-1-yl)propoxy]anilino}pyrimidine A mixture of potassium carbonate (180 mg, 1.3 mmol), 4-anilino-5-bromo-2-(4-hydroxyanilino)pyrimidine (Method 4, 150 mg, 0.42 mmol) and 3-(4-methyl-1-piperazinyl)propyl chloride dihydrochloride (120 mg, 0.48 mmol) in DMSO (2 ml) was heated at 100° C. for 12 hours. Silica (1 g) was added and volatile material was removed by evaporation. The residue was loaded onto a Varian Mega Bond Elut column and the column was eluted with 50:50 iso-hexane: DCM (2×20 ml), DCM (2×20 ml), 2% 2M NH$_3$/MeOH/DCM (2×20 ml), 4% 2M NH$_3$/MeOH/DCM (2×20 ml), 6% 2M NH$_3$/MeOH/DCM (2×20 ml) and 10% 2M NH$_3$/MeOH/DCM (8×20 ml). Concentration of the appropriate fractions gave the product as a yellow solid (35 mg, 17%). MS (MH$^+$): 497, 499; HPLC (RT): 2.74.

EXAMPLE 184

4-Anilino-5-bromo-2-{3-[3-(4-methylpiperazin-1-yl)propoxy]anilino}pyrimidine Using an analogous procedure to that described in Example 183, but starting from 4-anilino-5-bromo-2-(3-hydroxyanilino)pyrimidine (Method 6), the title product was obtained. MS (MH$^+$): 497, 499; HPLC (RT): 2.85.

EXAMPLES 185–192

The following compounds were prepared by an analogous method to that described in Example 136, starting from the appropriate substituted aniline (Methods 102–103, or obtained as described in Collect. Czech. Chem. Comm., 1990, 55, 282–95 and WO 9909030) and the appropriate 4-anilino-5-bromo-2-chloropyrimidine.

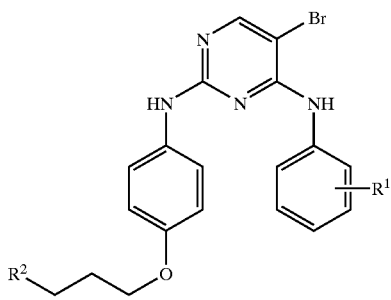

| Ex | R$^1$ | R$^2$ | NMR | MS (MH$^+$) |
|---|---|---|---|---|
| 185 | H | Et$_2$N— | 0.93(t, 6H), 1.76(tt, 2H), 2.43(q, 4H), 2.50(t, 2H), 3.91(t, 2H), 6.72(d, 2H), 7.10(t, 1H), 7.32(dd, 2H), 7.43(d, 2H), 7.60(d, 2H), 8.14(s, 1H), 8.44(s, 1H), 9.08(s, 1H) | 470.4, 472.4 |
| 186 | H | Me$_2$N— | 1.78(tt, 2H), 2.11(s, 6H), 2.32(t, 2H), 3.91(t, 2H), 6.72(d, 2H), 7.11(t, 1H), 7.32(dd, 2H), 7.43(d, 2H), 7.60(d, 2H), 8.14(s, 1H), 8.44(s, 1H), 9.07(s, 1H) | 442.3, 444.3 |
| 187 | 3-Me | Me$_2$N— | HPLC (RT) 5.66 | 456, 458 |
| 188[1] | H | i-PrNH— | 1.2(d, 6H), 2.1(m, 2H), 3(m, 2H), 3.3 (m, 1H), 4.0(t, 2H), 6.8(d, 2H), 7.2(t, 1H), 7.4(m, 4H), 7.6(d, 2H), 8.3(s, 1H), 9.3(br s, 1H), 9.5(br s, 1H) | 456, 458 |
| 189[1] | 2-HOCH$_2$— | i-PrNH— | 1.2(d, 6H), 2.1(m, 2H), 3.0(m, 2H), 3.3 (m, 1H), 4.0(t, 2H), 4.5(s, 2H), 6.8(d, 2H), 7.2(m, 1H), 7.3(m, 4H), 7.4(d, 1H), 7.8(d, 1H) 8.3(s, 1H), 9.3(br s, 1H), 9.5 (br s, 1H) | 486, 488 |
| 190[1] | 4-F | i-PrNH— | 1.2(d, 6H), 2.1(m, 2H), 3.0(m, 2H), 3.3 (m, 1H), 4.0(t, 2H), 6.8(d, 2H), 7.2(m, 2H), 7.3(m, 2H), 7.6(d, 2H), 8.3(s, 1H), 9.3(br s, 1H), 9.5(br s, 1H) | 474, 476 |
| 191 | H | imidazol-1-yl | 2.2(m, 2H), 3.9(m, 2H), 4.4(m, 2H), 6.7 (d, 2H), 7.2(m, 1H), 7.4(m, 4H), 7.5(m, 2H), 7.7(s, 1H), 7.8(s, 1H), 8.3(s, 1H), 9.2(s, 1H), 9.3(s, 1H), 9.5(s, 1H) | 465, 467 |
| 192 | 4-F | imidazol-1-yl | 2.1(m, 2H), 3.8(m, 2H), 4.2(m, 2H), 6.7 (d, 2H), 6.9(s, 1H), 7.2(m, 2H), 7.4(m, 2H), 7.6(m, 2H), 8.1(s, 1H), 8.6(s, 1H), 9.1(s, 1H) | 483, 485 |

[1]Isolated by filtration from the reaction mixture and washing with n-butanol and diethyl ether.

EXAMPLE 193

4-Anilino-5-bromo-2-[4-(3-morpholinopropoxy)anilino]pyrimidine

Triphenylphosphine (400 mg, 1.5 mmol) was added to a stirred solution of 4-anilino-5-bromo-2-(4-hydroxyanilino)pyrimidine (Method 4, 178 mg, 0.5 mmol) in DCM (40 ml) and the solution was stirred for 30 minutes. A solution of 4-(3-hydroxypropyl)morpholine (80 mg, 1.5 mmol) in DCM (2 ml) was added and the solution was stirred for 2 minutes. Diethyl azodicarboxylate (0.25 ml, 1.5 mmol) was added dropwise and the mixture was stirred for 20 hours. Volatile material was removed by evaporation and the residue was dissolved into ethyl acetate (100 ml). The solution was washed with water (2×50 ml) and then extracted with 2M hydrochloric acid (2×30 ml). The combined acidic extracts were washed with ethyl acetate (2×50 ml) and then basified by addition of 0.88 ammonia solution. The basified solution was extracted with ethyl acetate (2×50 ml) and the extracts were washed with water (2×50 ml) and saturated sodium chloride (2×50 ml) and dried. Volatile material was removed by evaporation and the residue was loaded on a Varian Mega Bond Elut column. Elution with 0–10% methanol in ethyl acetate and evaporation of the appropriate fractions gave an oil, which was treated with methanolic hydrogen chloride. Volatile material was removed by evaporation and the residue was recrystallized from a mixture of methanol and ether to give the product as a dihydrochloride salt (28 mg). NMR: 2.2 (m, 2H), 3.1 (m, 2H), 3.2 (m, 2H), 3.4 (d, 2H), 3.8–4.1 (m, 6H), 6.8 (d, 2H), 7.2–7.3 (t, 1H), 7.3–7.5 (m, 4H), 7.6 (d, 2H), 8.4 (s, 1H), 9.5 (br s, 1H), 10.1 (br s, 1H), 11.3 (br s, 1H); MS (MH$^+$): 484, 486.

EXAMPLE 194

5-Bromo-2-{4-[3-(N,N-dimethylamino)propoxy]anilino}-4-[(6-methylpyrid-2-yl)amino]pyrimidine Using an analogous method to that described in Example 136, but starting from 5-bromo-2-chloro-4-[(6-methylpyrid-2-yl)amino]pyrimidine (Method 84) and 4-[3-(N,N-dimethylamino)propoxy]aniline (obtained as described in WO 9909030), the product was obtained. MS (MH$^+$): 457, 459; HPLC (RT): 5.26.

EXAMPLES 195–196

The following compounds were prepared by an analogous method to that described in Example 1, starting from 4-anilino-5-bromo-2-chloropyrimidine (Method 13) and the appropriate 4-substituted aniline (Methods 106–107).

| Ex | R | NMR | MS (MH$^+$) |
|---|---|---|---|
| 195 | Me$_2$N— | 2–2.1(m, 2H), 2.7(s, 6H), 3.1–3.2(m, 2H), 3.3(m, 2H), 7.1(m, 2H), 7.2(m, 1H) 7.4(m, 2H), 7.5(m, 2H), 7.6 (m, 2H), 8.3(s, 1H), 9.3(s, 1H) | 441, 443 |
| 196 | imidazol-1-yl | 2.2(m, 2H), 3.1–3.2(m, 2H), 4.4(m, 2H), 7.2(m, 3H), 7.4(m, 2H) 7.5(m, 4H), 7.7(s, 1H), 7.8(s, 1H), 8.3(s, 1H), 9.2(s, 1H), 9.4(s, 1H) | 464, 466 |

EXAMPLES 197–215

The following compounds were prepared by an analogous method to that described in Example 1, starting from the appropriate 4-anilino-5-bromo-2-chloropyrimidine and the appropriate 4-substituted aniline (Methods 106–108).

| Ex | R$^1$ | R$^2$ | MS (MH$^+$) | HPLC (RT) |
|---|---|---|---|---|
| 197 | 3-Me | Me$_2$N— | 455, 457 | 4.13 |
| 198 | 3-Me | i-PrNH— | 469, 471 | 4.51 |
| 199 | 4-F | imidazol-1-yl | 482, 484 | 3.98 |
| 200 | 3-F | imidazol-1-yl | 482, 484 | 4.65 |
| 201 | 4-MeS | imidazol-1-yl | 510, 512 | 5.3 |
| 202 | 4-Br | imidazol-1-yl | 543, 545 | 5.63 |
| 203 | 3,4-di-F | imidazol-1-yl | 500, 502 | 4.94 |
| 204 | 4-F | Me$_2$N— | 459, 461 | 4.37 |
| 205 | 3-F | Me$_2$N— | 459, 461 | 4.26 |
| 206 | 4-Br | Me$_2$N— | 519, 521, 523 | 5.16 |
| 207 | 3,4-di-F | Me$_2$N— | 477, 479 | 4.60 |
| 208 | 3-F | i-PrNH— | 473, 475 | 4.53 |
| 209 | 4-MeS | i-PrNH— | 501, 503 | 5.26 |

-continued

| Ex | R¹ | R² | MS (MH⁺) | HPLC (RT) |
|---|---|---|---|---|
| 210 | 3,4-di-F | i-PrNH— | 491, 493 | 4.66 |
| 211 | 4-F | i-PrNH— | 473, 475 | 4.25 |
| 212 | 4-Br | i-PrNH— | 533, 535, 537 | 5.60 |
| 213 | 2-HOCH₂ | imidazol-1-yl | 494, 496 | 3.83 |
| 214 | 2-HOCH₂ | i-PrNH— | 485, 487 | 3.61[1] |
| 215 | 2-HOCH₂ | Me₂N— | 471, 473 | 3.74 |

[1] Data obtained from a Hypersil 10 cm base deactivated reverse phase column, using 10–95% acetonitrile/water gradient, flow rate 1 ml/min over 10 minutes.

EXAMPLES 216–221

The following compounds were prepared by an analogous method to that described in Example 1, starting from the appropriate 5-bromo-2-chloro-4-(2-pyridylamino)pyrimidine and the appropriate 4-substituted aniline.

| Ex | R¹ | R² | MS (MH⁺) | HPLC (RT) |
|---|---|---|---|---|
| 216 | Me | Me₂N— | 456, 458 | 3.21 |
| 217 | Me | i-PrNH— | 470, 472 | 3.22 |
| 218 | Me | imidazol-1-yl | 479, 481 | 4.07 |
| 219 | H | imidazol-1-yl | 465, 467 | 3.69 |
| 220 | H | i-PrNH— | 456, 458 | 1.80[1] |
| 221 | H | Me₂N— | 442, 444 | 1.75 |

[1] Data obtained from a Hypersil 10 cm base deactivated reverse phase column, using 10–95% acetonitrile/water gradient, flow rate 2 ml/min over 10 minutes.

EXAMPLES 222–223

The following compounds were prepared by an analogous method to that described in Example 1, starting from the appropriate 4-substituted 5-bromo-2-chloropyrimidine and 5-amino-2-[3-(isopropylamino)propylamino]pyridine (Method 109).

| Ex | X | R | MS (MH⁺) | HPLC (RT) |
|---|---|---|---|---|
| 222 | CH | H | 456, 458 | 3.06 |
| 223 | N | Me | 471, 473 | 4.06 |

EXAMPLE 224

4-Anilino-5-bromo-2-{4-[2-hydroxy-3-(N',N'-dimethylhydrazino)propoxy]anilino}pyrimidine 4-Anilino-5-bromo-2-[4-(2,3-epoxypropoxy)anilino]pyrimidine (Method 3, 100 mg, 0.24 mmol) was dissolved in THF (1 ml). N,N-Dimethylhydrazine (148 mg, 2.42 mmol) was added and the mixture was heated at 100° C. for 1 hour. Volatile material was removed by evaporation and the residue was triturated with diethyl ether (2 ml) to give the product as a yellow solid (83 mg, 74%). MS (MH⁺): 473, 475; HPLC (RT): 3.37.

EXAMPLES 225–230

The following compounds were prepared by an analogous method to that described in Example 224, starting from 4-anilino-5-bromo-2-[4-(2,3-epoxypropoxy)-2-fluoroanilino]pyrimidine (Method 2) and the appropriate amine.

| Ex | R¹ | R² | MS (MH⁺) | HPLC (RT) |
|---|---|---|---|---|
| 225 | i-Bu | H | 504, 506 | 4.17 |
| 226 | cyclopentyl | H | 516, 518 | 4.56 |
| 227 | pyrrolidino | | 503, 505 | 3.68 |
| 228 | 4-methylpiperazin-1-yl | | 531, 533 | 2.38 |
| 229 | Me | Me | 477, 479 | 3.11 |
| 230 | Me₂N— | H | 491, 493 | 3.23 |

EXAMPLE 231

4-Anilino-5-bromo-2-{4-[3-ethoxy-2-(hydroxy)propoxy]anilino}pyrimidine

Using an analogous method to that described in Example 136, but starting from 4-anilino-5-bromo-2- chloropyrimidine (Method 13) and 4-[3-ethoxy-2-(hydroxy) propoxy]aniline (obtained as described in J. Med. Chem., 1998, 41, 330–36), the product was obtained in 21% yield. NMR: 1.10 (t, 3H), 3.42 (m, 2H), 3.45 (q, 2H), 3.75–3.9 (m, 3H), 4.99 (d, 1H), 6.74 (d, 2H), 7.12 (t, 1H), 7.33 (dd, 2H), 7.44 (d, 2H), 7.60 (d, 2H), 8.15 (s, 1H), 9.10 (s, 1H); MS (MH$^+$): 459.3, 461.4.

EXAMPLE 232

4-Anilino-5-bromo-2-{4-[2.2-dimethyl-3-(N,N-dimethylamino)propylamino]anilino}pyrimidine Using an analogous method to that described in Example 1, but starting from 4-anilino-5-bromo-2-chloropyrimidine (Method 13) and 4-[2,2-dimethyl-3-(N,N-dimethylamino) propylamino]aniline (Method 110), the product was obtained. NMR: 0.9 (s, 6H), 2.15 (s, 2H), 2.2 (s, 6H), 2.8 (d, 2H), 5.1 (m, 1H), 6.5 (d, 2H), 7.1 (m, 1H), 7.2 (m, 2H), 7.3 (m, 2H), 7.6 (m, 2H), 8.1 (s, 1H), 8.3 (s, 1H), 8.8 (s, 1H); MS (MH$^+$): 469, 471.

EXAMPLE 233

4-Anilino-5-bromo-2-(4-{N-[2-hydroxy-3-(N,N-dimethylamino)propyl]-N-methylamino}anilino) pyrimidine Using an analogous method to that described in Example 1, but starting from 4-anilino-5-bromo-2-chloropyrimidine (Method 13) and 4-{N-[2-hydroxy-3-(N,N-dimethylamino) propyl]-N-methylamino}aniline (Method 116), the product was obtained. MS (MH$^+$): 471, 473; HPLC (RT): 4.53.

EXAMPLE 234

4-Anilino-5-bromo-2-{4-[2-hydroxy-2-methyl-3-(isopropylamino)propoxy]anilino}pyrimidine Using an analogous method to that described in Example 1, but starting from 4-anilino-5-bromo-2-chloropyrimidine (Method 13) and 4-[2-hydroxy-2-methyl-3-(isopropyl amino)propoxy]aniline (Method 118), the product was obtained. MS (MH$^+$): 486, 488; HPLC (RT): 4.26.

Preparation of Starting Materials

The starting materials for the Examples above are either commercially available or are readily prepared by standard methods from known materials. For example, the following reactions are an illustration, but not a limitation, of some of the starting materials used in the above reactions.

Method 1

4-Anilino-5-ethoxycarbonyl-2-{4-[2-hydroxy-3-(N, N-dimethylamino)propoxy]anilino}pyrimidine Using an analogous method to that described in Example 1, but starting from 4-anilino-2-chloro-5-ethoxycarbonylpyrimidine (Method 11) and treating the material obtained after chromatography with ethereal hydrogen chloride, the product was obtained in 57% yield as a dihydrochloride salt. MS (MH$^+$): 464.5, 466.5.

Method 2

4-Anilino-5-bromo-2-[4-(2,3-epoxypropoxy)-2-fluoroanilino]pyrimidine

Potassium carbonate (1.1 g, 8.01 mmol) and epibromohydrin (402 mg, 2.94 mmol) were added to a solution of 4-anilino-5-bromo-2-(2-fluoro-4-hydroxyanilino) pyrimidine (Method 5; 1.0 g, 2.67 mmol) in DMF (3 ml), and the suspension was stirred at room temperature for 16 hours. Volatile material was removed by evaporation and the residue was stirred vigorously in water. The solid remaining was collected by filtration and dried under vacuum to give the product (1.1 g, 98%). MS (MH$^+$): 431.

Method 3

4-Anilino-5-bromo-2-[4-(2,3-epoxypropoxy)anilino] pyrimidine

Using an analogous procedure to that described in Method 2, but starting from 4-anilino-5-bromo-2-(4-hydroxyanilino) pyrimidine (Method 4), the product was obtained in 49% yield. MS (MH$^-$): 413.

Method 4

4-Anilino-5-bromo-2-(4-hydroxyanilino)pyrimidine

4-Aminophenol (0.73 g, 7.8 mmol) and concentrated hydrochloric acid (1.30 ml, 7.1 mmol) were added to 4-anilino-5-bromo-2-chloropyrimidine (Method 13; 3.0 g, 7.1 mmol) in n-butanol (30 ml), and the mixture was heated at 100° C. for 12 hours. The solid which precipitated out on cooling was filtered off and washed with n-butanol and diethyl ether to give the product (0.80 g, 32%). MS (MH$^+$): 357, 359.

Methods 5–6

The following intermediates were prepared by an analogous method to that described in Method 4, using the appropriate aminophenol.

| Method | R | MS (MH$^+$) |
|---|---|---|
| 5 | 2-F, 4-OH | 375, 377 |
| 6 | 3-OH | 357, 359 |

Method 7

4-Anilino-2,5-dichloropyrimidine

A solution of 2,4,5-trichloropyrimidine (Method 8; 5.5 g, 30.0 mmol), aniline (2.79 g, 30.0 mmol) and N,N-diisopropylethylamine (3.87 g, 30.0 mmol) in n-butanol (75 ml) was heated under reflux for 4 hours. Volatile material was removed by evaporation and the residue was dissolved in DCM (100 ml). The solution was washed with water (3×100 ml) and saturated brine (100 ml) and dried. Volatile material was removed by evaporation and the residue was purified by column chromatography on silica gel, eluting with 15% ethyl acetate/isohexane, to give the product as an oil which solidified on standing (3.94 g, 54%). NMR: 7.2 (t, 1H), 7.4 (t, 2H), 7.6 (d, 2H), 8.4 (s, 1H), 9.45 (br s, 1H); MS (MH⁺): 240, 242, 244.

Method 8

2,4,5-Trichloropyrimidine

5-Chlorouracil (10.0 g, 68.5 mmol) was dissolved in phosphorus oxychloride (60 ml) and phosphorus pentachloride (16.0 g, 77.0 mmol) was added. The mixture was heated under reflux for 16 hours, left to cool and then poured slowly into water (200 ml) with vigorous stirring. The mixture was stirred for 1.5 hours and then ethyl acetate (250 ml) was added. The organic layer was separated and the aqueous layer was extracted with a further portion of ethyl acetate (250 ml). The combined extracts were washed with saturated sodium bicarbonate (200 ml) and saturated sodium chloride (200 ml), and then dried. Volatile material was removed by evaporation and the residue was purified by column chromatography, eluting with DCM, to give the product as a yellow liquid (6.37 g, 51%). NMR (CDCl₃): 8.62 (s, 1H); MS (MH⁺): 182, 184, 186.

Method 9

4-Anilino-2-chloro-5-(N-isopropylcarbamoyl)pyrimidine

A solution of aniline (0.292 ml, 3.2 mmol) and triethylamine (0.447 ml, 3.21 mmol) in THF (5 ml) was added dropwise over 10 minutes to a solution of 2,4-dichloro-5-(N-isopropylcarbamoyl)pyrimidine (Method 10, 0.75 g, 3.2 mmol) in distilled THF (8 ml) at −10° C. under nitrogen. The solution was stirred at −10° C. for 1 hour and at room temperature for 2 days. Insoluble material was removed by filtration and the filtrate was diluted with ethyl acetate (20 ml). The solution was washed with water (20 ml) and saturated sodium chloride (20 ml), and then dried. Volatile material was removed by evaporation and the residue was recrystallized from DCM to give the product as a white solid (0.34 g), which was used without characterisation.

Method 10

2,4-Dichloro-5-(N-isopropylcarbamoyl)pyrimidine

A solution of isopropylamine (1.28 ml, 15.0 mmol) and triethylamine (2.10 ml, 15.1 mmol) in dry THF (5 ml) was added dropwise over 30 minutes to a solution of 2,4-dichloropyrimidine-5-carbonyl chloride (obtained as described in J. Med. Chem., 1972, 15, 200; 3.18 g, 15.0 mmol) in dry THF (8 ml) at −10° C. The solution was stirred 0° C. for 2 hours, filtered and evaporated to dryness to yield the product (0.93 g), which was used without further purification.

Methods 11–59

The following intermediates were prepared by an analogous method to that described in Method 7, using the appropriate substituted aniline and 5-substituted 2,4-dichloropyrimidine (Methods 7, 60–61, or obtained as described in J. Org. Chem., 1955, 20, 837; J. Chem. Soc., 1960, 4590; Annalen, 1966, 692, 119; WO9204901; Eur. J. Med. Chem., 1991, 26, 557; Tet. Lett., 1993, 34, 1605).

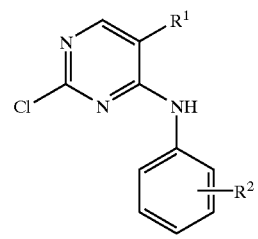

| Method | R¹ | R² | MS (MH⁺) |
|---|---|---|---|
| 11 | EtCO₂— | H | 278.2, 280.2 |
| 12 | Me | H | 220.2, 222.2 |
| 13 | Br | H | 284, 286, 288 |
| 14 | Br | 2-Ph | 360.1, 362.1, 364.1 |
| 15 | Br | 3,4-(CH₂)₃** | 324.1, 326.1, 328.1 |
| 16 | Br | 2-F, 5-Me | 316.1, 318.1, 320.1 |
| 17 | NO₂ | 2-F | 269, 271 |
| 18 | Br | 2-Br, 4-Me | 376.0, 378.0, 380.0, 382.0 |
| 19 | Br | 2-morpholino | 367.1, 369.1, 371.2 (MH⁻) |
| 20 | Br | 4-Br | 360.0, 362.0, 364.0, 366.0 (MH⁻) |
| 21 | Me | 3-Cl | 254, 256, 258 |
| 22 | Cl | 2-Cl, 5-Me | 288.0, 290.1, 292.1 |
| 23 | Cl | 2-morpholino | 325.1, 327.2, 329.2 |
| 24 | Cl | 4-Br | 316.0, 318.0, 320.0, 322.0, (MH⁻) |
| 25 | Br | 2-PhCH₂— | 374, 376 |
| 26 | Br | 2-OPh | 376, 378 |
| 27 | Br | 2-PhCH₂O— | 390, 392 |
| 28 | F | H | 224.1, 226.1 |
| 29 | F | 2-Cl, 5-Me | 272.2, 274.2, 276.2 |
| 30 | F | 2-morpholino | 309.2, 311.2 |
| 31 | F | 4-Br | 302.0, 304.0, 306.2 |
| 32 | morpholino | H | 291, 293 |
| 33 | Br | 4-PhCH₂O— | 390, 392 |
| 34 | Br | 3-PhO— | 376, 378 |
| 35 | Br | 4-PhO— | 376, 378 |
| 36 | Br | 3-PhCH₂O— | 390, 392 |
| 37 | Br | 4-PhCH₂— | 374, 376 |
| 38 | Cl | 3,4-di-Cl | 306.1, 308.0, 310.0, 312.1, (MH-) |
| 39 | Cl | 2-F, 5-Me | 272.1, 274.2, 276.2 |
| 40 | Cl | 3,4-(CH₂)₃** | 280.2, 282.2, 284.2 |
| 41 | Cl | 2-CN | 265.1, 267.1, 269.1 |
| 42 | EtO— | H | 250, 252 |
| 43 | Br | 4-HOCH₂— | 314, 316, 318 |
| 44 | CH₂=CH— | H | 232, 234 |
| 45 | MeO— | H | 236, 238 |
| 46 | Br | 3-CF₃ | 352, 354 |
| 47 | Br | 4-CF₃ | 352, 354 |
| 48¹ | EtOCH₂— | H | |
| 49 | Br | 2,4-di-F | 318, 320 |
| 50 | Br | 4-MeO | 314, 316 |
| 51 | Br | 2-HOCH₂— | 314, 316 |
| 52² | Br | 4-F | |
| 53³ | Br | 3,4-di-F | |
| 54 | Br | 3-Me | 298, 300, 302 |
| 55 | Cl | 4-F | 258, 260 |
| 56⁴ | Br | 3-F | |
| 57⁵ | Br | 4-MeS— | |
| 58 | PhCH(OH)— | H | 312.2, 314.2 |
| 59 | I | H | 331, 333 |

¹NMR: 1.31(t, 3H), 3.58(q, 2H), 4.55(s, 2H), 7.12(t, 1H), 7.37(dd, 2H), 7.60(d, 2H), 7.97(s, 1H), 8.29(br s, 1H).
²NMR: 7.22(m, 2H), 7.55(m, 2H), 8.42(s, 1H), 9.32(s, 1H).
³NMR: 7.42(m, 2H), 7.72(m, 1H), 8.47(s, 1H), 9.37(s, 1H).
⁴NMR: 6.97(m, 1H), 7.45(m, 3H), 8.48(s, 1H), 9.35(s, 1H).
⁵NMR: 2.50(s, 3H), 7.27(d, 2H), 7.47(d, 2H) 8.42(s, 1H), 9.23(s, 1H).
**Such that R² and the phenyl ring to which it is attached forms indan-5-yl.

Method 60

2,4-Dichloro-5-(4-morpholino)pyrimidine 5-(4-Morpholino)uracil (obtained as described in J. Amer. Chem. Soc., 1951, 73, 1061; 750 mg, 3.8 mmol) and N,N-dimethylaniline (0.6 ml, 4.7 mmol) were added to phosphorous oxychloride (20 ml). The mixture was heated under reflux for 4 hours and then concentrated by evaporation. Water (40 ml) was added and the mixture was extracted with ethyl acetate (2×30 ml). The extracts were washed with 2M hydrochloric acid (20 ml) and water (20 ml) and then dried. Volatile material was removed by evaporation and the residue was purified by column chromatography, eluting with 33% ethyl acetate in isohexane, to give the product as a white solid (380 mg, 40%). NMR: 3.1 (t, 4H), 3.7 (t, 4H), 8.5 (s, 1H).

Method 61

2,4-Dichloro-5-ethoxypyrimidine

Using an analogous method to that described in Method 8, but starting from 5-ethoxyuracil (obtained by an analogous method to that described for the preparation of 5-methoxyuracil in J. Chem. Soc., 1960, 4590), the product was obtained in 25% yield. NMR ($CDCl_3$): 1.45 (t, 3H), 4.15 (q, 2H), 8.1 (s, 1H).

Method 62

2-Chloro-4-(3,4-dichloroanilino)-5-methylpyrimidine 3,4-Dichloroaniline (639 mg, 3.94 mmol) and concentrated hydrochloric acid (ca. 12M, 0.2 ml, ca. 2.4 mmol) were sequentially added to a solution of 5-methyl-2,4-dichloropyrimidine (643 mg, 3.94 mmol) in n-butanol (20 ml). The mixture was stirred at ambient temperature for 20 hours, after which time a gelatinous precipitate had fallen out of solution. DCM was added until a solution was obtained, and silica (2.5 g) was added. Volatile material was removed by evaporation and the residue was loaded on a Varian Mega Bond Elut column pre-conditioned with ethyl acetate. The column was eluted with 0–10% methanol solution in ethyl acetate containing 0.5% aqueous ammonia. The appropriate fractions were concentrated, and the residue was triturated with n-butanol (20 ml). The filtrate was evaporated onto silica (2.5 g) and loaded on a Varian Mega Bond Elut column pre-conditioned with isohexane. The column was eluted with 0–50% ethyl acetate solution in isohexane. Concentration of the appropriate fractions gave the product as a white solid (340 mg, 26%). NMR: 2.17 (s, 3H), 7.60 (d, 1H), 7.70 (dd, 1H), 8.00 (d, 1H), 8.11 (s, 1H), 8.97 (s, 1H); MS ($MH^+$): 288.1, 290.1, 292.1.

Method 63

4-Anilino-5-benzyl-2-chloropyrimidine

Triethylsilane (0.14 ml, 1.10 mmol) was added to a solution of 4-anilino-2-chloro-5-[1-hydroxy-1-phenylmethyl]pyrimidine (Method 58; 170 mg, 0.55 mmol) in trifluoroacetic acid (1.5 ml), and the mixture was stirred for 64 hours. Water (20 ml) was added and the mixture was neutralised with sodium carbonate powder and extracted with DCM (3×20 ml). The extracts were combined, washed with water (30 ml), dried, concentrated to a volume of 5 ml, and loaded on a Varian Mega Bond Elut column. Elution with DCM and concentration of the appropriate fractions gave the product as a yellow crystalline solid (42 mg, 26%). NMR ($CDCl_3$): 3.93 (s, 2H), 6.45 (br s, 1H), 7.08 (m, 1H), 7.2–7.4 (m, 9H), 8.09 (s, 1H); MS ($MH^+$): 296.2, 298.2.

Method 64

4-Anilino-5-cyano-2-(methanesulphonyl)pyrimidine

3-Chloroperoxybenzoic acid (57–86%; 2.67 g, 8.8–13.3 mmol) was added in aliquots to a solution of 4-anilino-5-cyano-2-(methylthio)pyrimidine (Method 65; 1.0 g, 4.13 mmol) in chloroform (100 ml), and the mixture was stirred for 2 hours. The mixture was washed with saturated sodium bicarbonate (100 ml), water (100 ml), and saturated sodium chloride (100 ml) and dried. Volatile material was removed by evaporation and the residue was taken up in DCM (10 ml). The solution was loaded onto a silica column pre-equilibrated with 20% ethyl acetate solution in isohexane. Elution with 20–50% ethyl acetate in isohexane and concentration of the appropriate fractions gave the product as a yellow solid (680 mg, 61%). NMR ($CDCl_3$): 3.26 (s, 3H), 7.30 (t, 1H), 7.44 (dd, 2H), 7.57 (d, 2H), 7.65 (br s, 1H), 8.71 (s, 1H); MS ($MH^+$): 274.9.

Method 65

4-Anilino-5-cyano-2-(methylthio)pyrimidine

Using a method analogous to that described in Method 7, but starting from 4-chloro-5-cyano-2-(methylthio)pyrimidine (obtained as described in J. Het. Chem. 1971, 8, 445) and performing the reaction at 85° C., the product was obtained in 93% yield. NMR ($CDCl_3$): 2.51 (s, 3H), 7.15 (br s, 1H), 7.20 (t, 1H), 7.40 (dd, 2H), 7.57 (d, 2H), 8.38 (s, 1H).

Method 66

4-Anilino-2-chloro-5-(4-phenyl-1-butynyl) pyrimidine

A solution of 4-anilino-2-chloro-5-iodopyrimidine (Method 59; 662 mg, 2.0 mmol), 4-phenyl-1-butyne (260 mg, 2.0 mmol) and triethylamine (0.56 ml, 4.0 mmol) in THF (20 ml) was purged with nitrogen. Tetrakis (triphenylphosphine)palladium(0) (25 mg) and cuprous iodide (12.5 mg) were added and the mixture was stirred for 20 hours. Insoluble material was removed by filtration and washed with diethyl ether (50 ml). The filtrate and washings were combined and concentrated, and the residue was purified by bond elute chromatography, eluting with 25% ethyl acetate in isohexane, to give the product (0.5 g). NMR ($CDCl_3$): 2.85 (m, 2H), 2.95 (m, 2H), 7.05 (m, 2H), 7.1–7.4 (m, 7H), 7.45 (dd, 2H), 8.2 (s, 1H); MS ($MH^+$): 334, 336.

Method 67

4-Anilino-2-chloro-5-(3-cyclopentyl-1-propynyl) pyrimidine

Using an analogous method to that described Method 66, but starting from 3-cyclopentylpropyne, the product was obtained in 72% yield. NMR ($CDCl_3$): 1.3–1.4 (m, 2H), 1.6–1.8 (m, 4H), 1.8–2.0 (m, 2H), 2.2 (m, 1H), 2.55 (d, 2H), 7.15 (t, 1H), 7.5–7.5 (m, 3H), 7.65 (d, 2H), 8.2 (s, 1H); MS ($MH^+$): 312, 314.

Method 68 trans-4-Anilino-2-chloro-5-(2-phenylethenyl) pyrimidine

A solution of 4-anilino-2-chloro-5-iodopyrimidine (Method 59, 331 mg, 1 mmol), styrene (130 mg, 1.2 mmol), triethylamine (0.5 ml) and palladium acetate (20 mg) in acetonitrile (10 ml) was heated at 80° C. for 20 hours. The solution was poured into water (100 ml) and the mixture was extracted with ethyl acetate (2×50 ml). The extracts were washed with water (2×50 ml) and saturated sodium chloride (50 ml) and dried. Volatile material was removed by evaporation and the residue was purified by bond elute chromatography, eluting with 10% ethyl acetate in isohexane, to give the product (40 mg). NMR (CDCl$_3$): 6.8 (d, 1H), 7.0 (d, 2H), 7.15 (t, 1H), 7.3–7.45 (m, 5H), 7.5 (d, 2H), 7.6 (d, 2H), 8.2 (s, 1H); MS (MH$^+$): 308, 310.

Method 69 trans-4-Anilino-2-chloro-5-[2-(4-fluorophenyl) ethenyl]pyrimidine

Using an analogous method to that described Method 68, but starting from 4-fluorostyrene, the product was obtained in 10% yield.

Method 70

4-Anilino-2-chloro-5-phenylpyrimidine

Phenylboronic acid (240 mg, 2 mmol) and tetrakis (triphenylphosphine)palladium(0) (30 mg) were added to a solution of 4-anilino-2-chloro-5-iodopyrimidine (Method 59, 331 mg, 1 mmol) in toluene (10 ml) and ethanol (2.5 ml). 2M aqueous sodium carbonate solution (10 ml) was added and the mixture was stirred and heated under reflux for 3 hours. Further portions of phenylboronic acid (240 mg, 2 mmol) and tetrakis(triphenylphosphine) palladium(0) (30 mg) were added and the mixture was stirred and heated under reflux for 20 hours. The mixture was poured into water (100 ml) and extracted with ethyl acetate (2×50 ml). The combined extracts were washed with water (2×50 ml) and saturated sodium chloride (50 ml) and dried. Volatile material was removed by evaporation and the residue was purified by bond elute chromatography, eluting with 10–25% ethyl acetate in isohexane, to give the product (140 mg). NMR (CDCl$_3$): 6.85 (s, 1H), 7.1 (t, 1H), 7.3 (t, 2H), 7.4 (m, 2H), 7.5–7.6 (m, 6H), 8.05 (s, 1H); MS (MH$^+$): 282, 284.

Method 71

4-Anilino-2-chloro-5-(2-phenylethyl)pyrimidine

4-Anilino-2-chloro-5-(2-phenylethynyl)pyrimidine (Method 72; 400 mg) was dissolved in ethyl acetate (100 ml) and the solution was purged with nitrogen. 5% Rhodium on carbon (50 mg) was added and the mixture was hydrogenated at standard temperature and pressure (STP) for 20 hours. A further portion of 5% rhodium on carbon catalyst (50 mg) was added and the solution was hydrogenated at STP for a further 3 hours. The catalyst was removed by filtration and the filtrate was concentrated. The residue was purified by bond elute chromatography, eluting with 0–10% ethyl acetate in isohexane, to give the product (70 mg). NMR (CDCl$_3$): 2.8 (t, 2H), 3.0 (t, 2H), 6.25 (s, 1H), 7.1 (m, 1H), 7.15–7.4 (m, 9H), 7.95 (s, 1H); MS (MH$^+$): 310, 312.

Method 72

4-Anilino-2-chloro-5-(2-phenylethynyl)pyrimidine

Using an analogous method to that described Method 67, but starting from phenyl acetylene, the product was obtained in 57% yield. NMR (CDCl$_3$): 7.2 (t, 1H), 7.4–7.5 (m, 5H), 7.5 (br s, 1H), 7.5–7.6 (m, 2H), 7.7 (d, 2H), 8.4 (s, 1H); MS (MH$^+$): 306, 308.

Method 73

4-Anilino-2-chloro-5-fur-3-ylpyrimidine

A solution of 4-anilino-2-chloro-5-iodopyrimidine (Method 59, 331 mg, 1 mmol), 3-furylboronic acid (224 mg, 2 mmol), caesium fluoride (400 mg, 2 mmol) and tetrakis (triphenylphosphine)palladium(0) (30 mg) in THF (10 ml) was stirred and heated at reflux for 20 hours under a nitrogen atmosphere. Insoluble material was removed by filtration and the filtrate was concentrated. The residue was purified by bond elute chromatography, eluting with 25% ethyl acetate in isohexane, to give the product (140 mg). NMR (CDCl$_3$): 6.6 (d, 1H), 7.0 (br s, 1H), 7.15 (t, 1H), 7.25 (s, 1H), 7.4 (t, 2H), 7.55 (d, 2H), 7.65 (d, 2H), 8.1 (s, 1H); MS (MH$^+$): 272, 274.

Method 74

4-[4-Bromo-N-(4,4,4-trifluorobutyl)anilino]-2,5-dichloropyrimidine

A mixture of 4-(4-bromoanilino)-2,5-dichloropyrimidine (Method 24; 315 mg, 1.0 mmol), 4,4,4-trifluoro-1-bromobutane (228 mg, 1.20 mmol) and potassium carbonate (165 mg, 1.20 mmol) in DMF (3 ml) was stirred at room temperature for 12 hours. Silica (2.5 g) was added and volatile material was removed by evaporation. The residue was purified by column chromatography, eluting with 0–40% ethyl acetate in isohexane, to give the product (187 mg). NMR: (373K); 1.84 (m, 2H), 2.28 (m, 2H), 3.99 (t, 2H), 7.22 (d, 2H), 7.58 (d, 2H), 8.23 (s, 1H); MS (MH$^+$): 428.2, 430.2, 432.2.

Methods 75–78

The following intermediates were prepared by an analogous method to that described in Method 74, using the appropriate 4-anilino-2-chloro-5-halopyrimidine (Methods 7, 13, 15, 24) and the appropriate alkyl halide.

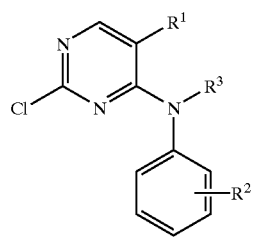

| Method | R$^1$ | R$^2$ | R$^3$ | MS (MH$^+$) |
|---|---|---|---|---|
| 75 | Br | H | —(CH$_2$)$_3$CF$_3$ | 394.1, 396.1, 398.1 |
| 76 | Cl | H | —(CH$_2$)$_3$CF$_3$ | 350.2, 352.2 |
| 77 | Cl | 4-Br | —CH$_2$CH=CHBr | 436.1, 438.1, 440.1, 442.1 |
| 78 | Cl | 2-F, 5-Me | —CH$_2$CH=CHPh | 388.3, 390.3 |

Methods 79–80

The following intermediates were prepared by an analogous method to that described in Method 7, using the appropriate 2,4-dichloro-5-halopyrimidine and N-methylaniline:

| Method | R  | MS (MH⁺)  |
|--------|----|-----------|
| 79     | Cl | 252, 254  |
| 80     | Br | 298, 300  |

Methods 81–84

The following intermediates were prepared by an analogous method to that described in Method 7, using the appropriate 2-aminopyridine and 2,4-dichloro-5-halopyrimidine.

| Method | R¹ | R² | MS (MH⁺) |
|--------|----|----|----------|
| 81 | Br | H  | 285, 287 |
| 82 | Cl | Me | 254, 256 |
| 83 | Cl | H  | 240, 242 |
| 84 | Br | Me | 299, 301 |

Methods 85–86

The following intermediates were prepared by an analogous method to that described in Method 7, using the appropriate 3-aminopyridine and 5-bromo-2,4-dichloropyrimidine.

| Method | R¹  | R²   | MS (MH⁺) |
|--------|-----|------|----------|
| 85     | NH₂ | H    | 300, 302 |
| 86     | H   | MeO— |          |

Methods 87–88

The following intermediates were prepared by an analogous method to that described in Method 7, using the appropriate amino heterocycle and 5-bromo-2,4-dichloropyrimidine.

| Method | R                  | MS           |
|--------|--------------------|--------------|
| 87     | 4-methylthiazol-2-yl | 303, 305 (MH⁻) |
| 88     | 5-methylpyrazol-3-yl | 288, 290 (MH⁺) |

Method 89

4-[2-Hydroxy-3-(N,N-dimethylamino)propoxy] aniline hydrochloride

A solution of 4-[2-hydroxy-3-(N,N-dimethylamino) propoxy]nitrobenzene (Method 90, 3.75 g) in ethanol (40 ml) was catalytically hydrogenated over 10% palladium-on-carbon (0.4 g) overnight. The catalyst was removed by filtration through diatomaceous earth and the filtrate was concentrated. The residue was dissolved in diethyl ether containing a small amount of isopropanol and ethereal hydrogen chloride (1M, 16 ml) was added. Diethyl ether was removed by evaporation and the solid residue was suspended in isopropanol. The mixture was heated on a steam bath for several minutes and then allowed to cool. The insoluble solid was collected by filtration, washed with isopropanol and ether, and dried to give the product (3.04 g, 72.4%). NMR: 2.80 (s, 6H), 3.15 (m, 2H), 3.88 (m, 2H), 4.25 (m, 1H), 5.93 (br s, 1H), 6.88 (m, 4H); MS (MH⁺): 211; $C_{11}H_{18}N_2O_2 \cdot 1.6$ HCl requires: C; 49.2,H; 7.4, N; 10.4, Cl; 21.7%; found: C; 49.2, H; 7.2, N; 10.1; Cl; 19.1%.

Method 90

4-[2-Hydroxy-3-(N,N-dimethylamino)propoxy] nitrobenzene 4-(2,3-Epoxypropoxy)nitrobenzene (obtained as described in Synthetic Communications, 1994, 24, 833; 4.3 g,) was dissolved in methanol (30 ml) and DMF (10 ml). A solution of dimethylamine in methanol (2M, 17 ml) was added and the mixture was stirred overnight. Volatile material was removed by evaporation and the residue was partitioned between saturated sodium bicarbonate (100 ml) and ethyl acetate (100 ml). The organic layer was separated and washed with saturated sodium chloride (2×100 ml) and dried. Concentration gave the product as an oil that slowly crystallised under high vacuum (4.79 g, 89.9%). NMR (CDCl₃): 2.33 (s, 6H), 2.98 (m, 1H), 2.54 (m, 1H), 4.00 (m, 3H), 7.00 (d, 2H), 8.20 (d, 2H); MS (MH⁺): 241.

Method 91

4-{2-Hydroxy-3-[(4-methyl-1-piperazino)propoxy]}aniline

N-Methylpiperazine (8.50 ml, 51.2 mmol) was added to a solution of 4-(2,3-epoxypropoxy)nitrobenzene (obtained as described in Synthetic Communications, 1.00 g, 5.12 mmol) in THF (1 ml). The solution was heated under reflux for 3 hours and then concentrated on a rotary evaporator under high vacuum at 50° C. for 1 hour. The residue was dissolved in methanol (5 ml) and 10% palladium on carbon (0.50 g) and ammonium formate (3.23 g, 51.2 mmol) were added. The reaction mixture was heated under reflux for 3 hours and then filtered through diatomaceous earth. The filtrate was concentrated under reduced pressure to give the product as dark brown oil (1.35 g, 100%), which was used without further purification. MS (MH$^+$): 266.5.

Methods 92–101

The following intermediates were prepared by an analogous method to that described in Method 91, using the appropriate amine.

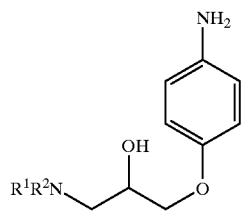

| Method | R$^1$ | R$^2$ | MS (MH$^+$) |
|---|---|---|---|
| 92[1] | PhCH$_2$— | i-Pr | 315.4 |
| 93[1] | CH$_2$=CHCH$_2$— | Me | 236.9 |
| 94 | i-Bu | H | 238.9 |
| 95 | cyclopentyl | H | 250.9 |
| 96 | pyrrolidino | | 236.9 |
| 97[2] | Me | H | 196.9 |
| 98[2] | H | H | 182.9 |
| 99[2] | Et | H | 210.9 |
| 100 | morpholino | | 252.9 |
| 101 | 4-acetylpiperazin-1-yl | | 296.9 |

[1]The intermediate substituted nitrobenzene was reduced by a different method. The residue was dissolved in ethanol (2.5 ml) and water (2.5 ml) and warmed to 80° C. Sodium dithionite (2.67 g, 15.4 mmol) was added over a period of 20 minutes. Insoluble material was removed by filtration and the filtrate was concentrated. The reside was suspended in 10% aqueous sodium bicarbonate (10 ml) and the mixture was extracted with DCM (20 ml). The extracts were washed with water (10 ml) and concentrated under reduced pressure to afford the product as an orange oil, which was used without further purification.
[2]Prepared from the corresponding N-benzyl substituted precursors. For complete debenzylation, the reactions required a further addition of palladium on carbon (0.50 g) and ammonium formate (3.23 g mmol).

Methods 102–103

The following intermediates were prepared by an analogous method to that described in Method 89, using the appropriate nitrobenzene (Methods 104–105).

| Method | R | MS (MH$^+$) |
|---|---|---|
| 102 | i-PrNH | 209 |
| 103 | imidazol-1-yl | 218 |

Method 104

4-(3-Isopropylaminopropoxy)nitrobenzene

Potassium carbonate (1.0 g, 5.0 mmol) was added to a solution of 4-(3-bromopropoxy) nitrobenzene (obtained as described in Synthesis, 1990, 1069; 1.0 g, 3.9 mmol) in DMF (30 ml). Isopropylamine (0.4 ml, 4.6 mmol) was added and the mixture was heated at 60° C. for 2 hours. Volatile material was removed by evaporation and the residue was dissolved in ethyl acetate (200 ml). The solution was washed with water (3×25ml) and saturated sodium chloride (25 ml) and then dried. The solvent was removed by evaporation and the residue was dissolved in isopropanol (10 ml). Ethereal hydrogen chloride (2M; 2 ml) was added and the precipitated solid was collected to give the product as a hydrochloride salt (0.60 g, 65%). MS (MH$^+$): 239.

Method 105

4-[3-(Imidazol-1-yl)propoxy]nitrobenzene

A mixture of imidazole (0.8 g, 11.6 mmol) and 4-(3-bromopropoxy)nitrobenzene (1.5 g, 5.8 mmol) in 1,4-dioxane (75 ml) was heated at 100° C. for 12 hours. Volatile material was removed by evaporation and the residue was dissolved in ethyl acetate (150 ml). The solution was washed with saturated sodium bicarbonate (3×50 ml), water (3×50 ml) and saturated sodium chloride (50 ml) and then dried. The solvent was removed by evaporation and the residue was purified by column chromatography, eluting with 0–5% methanol in DCM, to give the product as a yellow oil (0.51 g, 22%). MS (MH$^+$): 248.

Methods 106–110

The following intermediates were prepared by an analogous method to that described in Method 89, using the appropriate nitrobenzene (Methods 111–115).

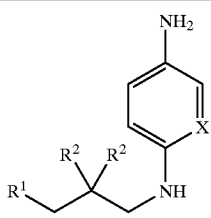

| Method | X | R¹ | R² | MS (MH⁺) |
|---|---|---|---|---|
| 106 | CH | Me₂N | H | 194 |
| 107 | CH | imidazol-1-yl | H | 217 |
| 108 | CH | i-PrNH | H | 208 |
| 109 | N | i-PrNH | H | 209 |
| 110 | CH | Me₂N | Me | 222 |

Method 111

4-[3-(N,N-dimethylamino)propylamino]nitrobenzene

N,N-Dimethylpropane-1,3-diamine (4.90 ml, 39 mmol) and potassium carbonate (6.37 g, 46 mmol) were added to 1-fluoro-4-nitrobenzene (5.0 g, 35 mmol) and the mixture was heated at 70° C. for 3 hours. Insoluble material was removed by filtration and the filtrate was concentrated. The residue was dissolved in ethyl acetate (100 ml) and the solution was washed with water (3×100 ml) and saturated sodium chloride (100 ml) and dried. The solvent was removed by evaporation to give the product as a yellow oil (8.57 g). MS (MH⁺): 248.

Methods 112–115

The following intermediates were prepared by an analogous method to that described in Method 111, using the appropriate amine and 1-fluoro-4-nitrobenzene or 2-chloro-5-nitropyridine.

| Method | X | R¹ | R² | MS (MH⁺) |
|---|---|---|---|---|
| 112 | CH | imidazol-1-yl | H | 246 |
| 113 | CH | i-PrNH | H | 238 |
| 114 | N | i-PrNH | H | 239 |
| 115 | CH | Me₂N | Me | 252 |

Method 116

4-{N-[2-Hydroxy-3-(N,N-dimethylamino)propyl]-N-methylamino}aniline

Using an analogous method to that described in Method 89, but starting from 4-{N-[2-hydroxy-3-(N,N-dimethylamino)propyl]-N-methylamino}nitrobenzene (Method 117), the product was obtained. MS (MH⁺): 224.

Method 117

4-{N-[2-Hydroxy-3-(N,N-dimethylamino)propyl]-N-methylamino}nitrobenzene

Sodium hydride (60% dispersion in oil; 290 mg, 7.2 mmol) was added portionwise over 30 minutes to a solution of 4-nitro-N-methylaniline (1.0 g, 6.6 mmol) in DMF (30 ml) at 0° C. Epibromohydrin (0.62 ml, 7.2 mmol) was added dropwise to the solution at 0° C. and the mixture was left to stand overnight. Volatile material was removed by evaporation and the residue was dissolved in a solution of dimethylamine in methanol (5.6M, 132 mmol). The solution was left to stand for 12 hours and then concentrated. The residue was dissolved in DCM (200 ml) and the solution was washed with water (3×20 ml) and saturated sodium chloride (20 ml) and dried. Evaporation gave the product as an orange solid (1.44 g, 86%). MS (MH⁺): 254.

Method 118

4-[2-Hydroxy-2-methyl-3-(isopropylamino)propoxy]aniline

Using an analogous method to that described in Method 89, but starting from 4-[2-hydroxy-2-methyl-3-(isopropylamino)propoxy]nitrobenzene (Method 119), the product was obtained in 52% yield. MS (MH⁺): 239.

Method 119

4-[2-Hydroxy-2-methyl-3-(isopropylamino)propoxy]nitrobenzene

A mixture of 4-nitrophenol (1.0 g, 7.1 mmol), potassium carbonate (1.30 g, 9.4 mmol) and 2-chloromethyl-2-methyloxirane (0.84 g, 7.9 mmol) in DMF (50 ml) was stirred for 12 hours and then heated at 80° C. for 12 hours. Insoluble material was removed by filtration and washed with DMF (10 ml). The combined filtrate and washings were concentrated and the residue was dissolved in methanol (20 ml). Isopropylamine (6.13 ml, 71 mmol) was added and the mixture was stirred for 12 hours. Volatile material was removed by evaporation and the residue was purified by bond elute chromatography, eluting with 0–5% methanol in DCM, to give the product as a yellow solid (0.5 g, 26%). MS (MH⁺): 269.

EXAMPLE 235

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph. Eur | 223.75 |
| Croscarmellose sodium | 6.0 |

| -continued | |
|---|---|
| Maize starch | 15.0 |
| Polyvinylpyrrolidone (5% w/v paste) | 2.25 |
| Magnesium stearate | 3.0 |
| (c): Tablet III | mg/tablet |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |
| (d): Capsule | mg/capsule |
| Compound X | 10 |
| Lactose Ph. Eur | 488.5 |
| Magnesium stearate | 1.5 |
| (e): Injection I | (50 mg/ml) |
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |
| (f): Injection II | 10 mg/ml |
| Compound X | 1.0% w/v |
| Sodium phosphate BP | 3.6% w/v |
| 0.1 M Sodium hydroxide solution | 15.0% v/v |
| Water for injection | to 100% |
| (g). Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What we claim is:
1. A pyrimidine compound of the formula (I):

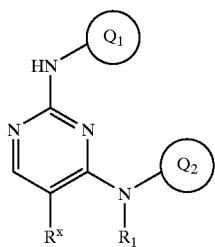

(I)

wherein:
$R^1$ is selected from hydrogen, $C_{1-6}$alkyl [optionally substituted by one or two substituents independently selected from halo, amino, $C_{1-4}$alkylamino, di-($C_{1-4}$alkyl)amino, hydroxy, cyano, $C_{1-4}$alkoxy, $C_{1-4}$alkoxycarbonyl, carbamoyl, —NHCOC$_{1-4}$alkyl, trifluoromethyl, phenylthio, phenoxy, pyridyl, morpholino], benzyl, 2-phenylethyl, $C_{3-5}$alkenyl [optionally substituted by up to three halo substituents, or by one trifluoromethyl substituent, or one phenyl substituent], N-phthalimido-$C_{1-4}$alkyl, $C_{3-5}$alkynyl [optionally substituted by one phenyl substituent] and $C_{3-6}$cycloalkyl-$C_{1-6}$alkyl; wherein any phenyl or benzyl group in $R^1$ is optionally substituted by up to three substituents independently selected from halo, hydroxy, nitro, amino, $C_{1-3}$alkylamino, di-($C_{1-3}$alkyl)amino, cyano, trifluoromethyl, $C_{1-3}$alkyl [optionally substituted by 1 or 2 substituents independently selected from halo, cyano, amino, $C_{1-3}$alkylamino, di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, mercapto, $C_{1-3}$alkylthio, carboxy, $C_{1-3}$alkoxycarbonyl;

$R^x$ is selected from halo, hydroxy, nitro, amino, cyano, mercapto, carboxy, sulphamoyl, formamido, ureido or carbamoyl or a group of formula (Ib):

A—B—C— (Ib)

wherein:
A is $C_{1-6}$alkyl, $C_{2-6}$alkenyl, $C_{2-6}$alkynyl, $C_{3-8}$cycloalkyl, phenyl, heterocycle or heteroaryl, wherein said $C_{1-6}$alkyl, $C_{3-6}$alkenyl and $C_{3-6}$alkynyl are optionally substituted by one or more substituents selected from halo, nitro, cyano, amino, hydroxy, mercapto, carboxy, formamido, ureido, $C_{1-3}$alkylamino, di-($C_{1-3}$alkyl)amino, $C_{1-3}$alkoxy, trifluoromethyl, $C_{3-8}$cycloalkyl, phenyl, heterocycle or heteroaryl; wherein any phenyl, $C_{3-8}$cycloalkyl, heterocycle or heteroaryl may be optionally substituted by one or more halo, nitro, cyano, hydroxy, trifluoromethyl, trifluoromethoxy, amino, carboxy, carbamoyl, mercapto, formamido, ureido, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, $C_{1-4}$alkylamino, di-($C_{1-4}$alkyl)amino, $C_{1-4}$alkanoylamino, N—$C_{1-4}$alkylcarbamoyl, N,N-di-($C_{1-4}$alkyl)carbamoyl, $C_{1-4}$alkylthio, $C_{1-4}$alkylsulphinyl, $C_{1-4}$alkylsulphonyl and $C_{1-4}$alkoxycarbonyl;

B is —O—, —S—, —C(O)—, —NH—, —N($C_{1-4}$alkyl)-, —C(O)NH—, —C(O)N($C_{1-4}$alkyl)-, —NHC(O)—, —N($C_{1-4}$alkyl)C(O)— or B is a direct bond;

C is $C_{1-4}$alkylene or a direct bond;

$Q_1$ and $Q_2$ are independently selected from aryl, a 5- or 6-membered monocyclic moiety (linked via a ring carbon atom and having one to three heteroatoms independently selected from nitrogen, oxygen and sulphur); and a 9- or 10-membered bicyclic heterocyclic moiety (linked via a ring carbon atom and having one or two nitrogen heteroatoms and optionally having a further one or two heteroatoms selected from nitrogen, oxygen and sulphur);

and one or both of $Q_1$ and $Q_2$ bears on any available carbon atom one substituent of the formula (Ia) and $Q_2$ may optionally bear on any available carbon atom further substituents of the formula (Ia):

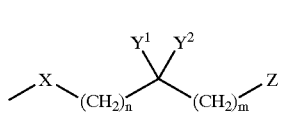

(Ia)

[provided that when present in $Q_1$ the substituent of formula (Ia) is not adjacent to the —NH— link];
wherein:
X is —CH$_2$—, —O—, —NH—, —NR$^y$— or —S— [wherein R$^y$ is $C_{1-4}$alkyl, optionally substituted by one substituent selected from halo, amino, cyano, $C_{1-4}$alkoxy or hydroxy];

$Y^1$ is H, $C_{1-4}$alkyl or as defined for Z;

$Y^2$ is H or $C_{1-4}$alkyl;

Z is $R^aO$—, $R^bR^cN$—, $R^dS$—, $R^eR^fNNR^g$—, a nitrogen linked heteroaryl or a nitrogen linked heterocycle [wherein said heterocycle is optionally substituted on a ring carbon or a ring nitrogen by $C_{1-4}$alkyl or $C_{1-4}$alkanoyl] wherein $R^a$, $R^b$, $R^c$, $R^d$, $R^e$, $R^f$ and $R^g$ are independently selected from hydrogen, $C_{1-4}$alkyl, $C_{2-4}$alkenyl, $C_{3-8}$cycloalkyl, and wherein said $C_{1-4}$alkyl and $C_{2-4}$alkenyl are optionally substituted by one or more phenyl;

n is 1, 2 or 3;

m is 1, 2 or 3;

and $Q_1$ may optionally bear on any available carbon atom up to four substituents independently selected from halo, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-($C_{1-4}$alkyl)amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N—$C_{1-4}$alkylcarbamoyl-$C_{1-4}$alkyl, N,N-di-($C_{1-4}$alkyl)-carbamoyl-$C_{1-4}$alkyl, pyrrolidin-1-yl-$C_{1-3}$alkyl, piperidino-$C_{1-3}$alkyl, piperazin-1-yl-$C_{1-3}$alkyl, morpholino-$C_{1-3}$alkyl, thiomorpholino-$C_{1-3}$alkyl, imidazo-1-yl-$C_{1-3}$alkyl, piperazin-1-yl, morpholino, thiomorpholino, $C_{1-4}$alkylthio, $C_{1-4}$alkylsulphinyl, $C_{1-4}$alkylsulphonyl, hydroxy$C_{2-4}$alkylthio, hydroxy$C_{2-4}$alkylsulphinyl, hydroxy$C_{2-4}$alkylsulphonyl, ureido, N'—($C_{1-4}$alkyl)ureido, N',N'-di-($C_{1-4}$alkyl)ureido, N'—($C_{1-4}$alkyl)-N—($C_{1-4}$alkyl)ureido, N',N'-di-($C_{1-4}$alkyl)-N—($C_{1-4}$alkyl)ureido, carbamoyl, N—($C_{1-4}$alkyl)carbamoyl, N,N-di-($C_{1-4}$alkyl)carbamoyl, amino, $C_{1-4}$alkylamino, di-($C_{1-4}$alkyl)amino, $C_{2-4}$alkanoylamino, sulphamoyl, N—($C_{1-4}$alkyl)sulphamoyl, N,N-di-($C_{1-4}$alkyl)sulphamoyl;

and also independently, or where appropriate in addition to, the above substituents, $Q_1$ may optionally bear on any available carbon atom up to two further substituents independently selected from $C_{3-8}$cycloalkyl, phenyl-$C_{1-4}$alkyl, phenyl-$C_{1-4}$alkoxy, phenylthio, phenyl, naphthyl, benzoyl, benzimidazol-2-yl, phenoxy and a 5- or 6-membered aromatic heterocycle (linked via a ring carbon atom and having one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-$C_{1-4}$alkyl, phenylthio and phenyl-$C_{1-4}$alkoxy substituents may optionally bear up to five substituents independently selected from halo, $C_{1-4}$alkyl and $C_{1-4}$alkoxy;

and $Q_2$ may optionally bear on any available carbon atom up to four substituents independently selected from halo, hydroxy, thio, nitro, carboxy, cyano, $C_{2-4}$alkenyl [optionally substituted by up to three halo substituents, or by one trifluoromethyl substituent], $C_{2-4}$alkynyl, $C_{1-5}$alkanoyl, $C_{1-4}$alkoxycarbonyl, $C_{1-6}$alkyl, hydroxy-$C_{1-3}$alkyl, fluoro-$C_{1-4}$alkyl, amino-$C_{1-3}$alkyl, $C_{1-4}$alkylamino-$C_{1-3}$alkyl, di-($C_{1-4}$alkyl)amino-$C_{1-3}$alkyl, cyano-$C_{1-4}$alkyl, $C_{2-4}$alkanoyloxy-$C_{1-4}$-alkyl, $C_{1-4}$alkoxy-$C_{1-3}$alkyl, carboxy-$C_{1-4}$alkyl, $C_{1-4}$alkoxycarbonyl-$C_{1-4}$alkyl, carbamoyl-$C_{1-4}$alkyl, N—$C_{1-4}$alkylcarbamoyl-$C_{1-4}$alkyl, N,N-di-($C_{1-4}$alkyl)-carbamoyl-$C_{1-4}$alkyl, pyrrolidin-1-yl-$C_{1-3}$alkyl, piperidino-$C_{1-3}$alkyl, piperazin-1-yl-$C_{1-3}$alkyl, morpholino-$C_{1-3}$alkyl, thiomorpholino-$C_{1-3}$alkyl, imidazo-1-yl-$C_{1-3}$alkyl, piperazin-1-yl, morpholino, thiomorpholino, $C_{1-4}$alkoxy, cyano-$C_{1-4}$alkoxy, carbamoyl-$C_{1-4}$alkoxy, N—$C_{1-4}$alkylcarbamoyl-$C_{1-4}$alkoxy, N,N-di-($C_{1-4}$alkyl)-carbamoyl-$C_{1-4}$alkoxy, 2-aminoethoxy, 2-$C_{1-4}$alkylaminoethoxy, 2-di-($C_{1-4}$alkyl)aminoethoxy, $C_{1-4}$alkoxycarbonyl-$C_{1-4}$alkoxy, halo-$C_{1-4}$alkoxy, 2-hydroxyethoxy, $C_{2-4}$alkanoyloxy-$C_{2-4}$alkoxy, 2-$C_{1-4}$alkoxyethoxy, carboxy-$C_{1-4}$alkoxy, 2-pyrrolidin-1-yl-ethoxy, 2-piperidino-ethoxy, 2-piperazin-1-yl-ethoxy, 2-morpholino-ethoxy, 2-thiomorpholino-ethoxy, 2-imidazo-1-yl-ethoxy, $C_{3-5}$alkenyloxy, $C_{3-5}$alkynyloxy, $C_{1-4}$alkylthio, $C_{1-4}$alkylsulphinyl, $C_{1-4}$alkylsulphonyl, hydroxy$C_{2-4}$alkylthio, hydroxy$C_{2-4}$alkylsulphinyl, hydroxy$C_{2-4}$alkylsulphonyl, ureido, N'—($C_{1-4}$alkyl)ureido, N',N'-di-($C_{1-4}$alkyl)ureido, N'—($C_{1-4}$alkyl)-N—($C_{1-4}$alkyl)ureido, N',N'-di-($C_{1-4}$alkyl)-N—($C_{1-4}$alkyl)ureido, carbamoyl, N—($C_{1-4}$alkyl)carbamoyl, N,N-di-($C_{1-4}$alkyl)carbamoyl, amino, $C_{1-4}$alkylamino, di-($C_{1-4}$alkyl)amino, $C_{2-4}$alkanoylamino, sulphamoyl, N—($C_{1-4}$alkyl)sulphamoyl, N,N-di-($C_{1-4}$alkyl)sulphamoyl, and also independently, or where appropriate in addition to, the above optional substituents, $Q_2$ may optionally bear on any available carbon atom up to two further substituents independently selected from $C_{3-8}$cycloalkyl, phenyl-$C_{1-4}$alkyl, phenyl-$C_{1-4}$alkoxy, phenylthio, phenyl, naphthyl, benzoyl, phenoxy, benzimidazol-2-yl, and a 5- or 6-membered aromatic heterocycle (linked via a ring carbon atom and having one to three heteroatoms independently selected from oxygen, sulphur and nitrogen); wherein said naphthyl, phenyl, benzoyl, phenoxy, 5- or 6-membered aromatic heterocyclic substituents and the phenyl group in said phenyl-$C_{1-4}$alkyl, phenylthio and phenyl-$C_{1-4}$alkoxy substituents may optionally bear one or two substituents independently selected from halo, $C_{1-4}$alkyl and $C_{1-4}$alkoxy; or a pharmaceutically acceptable salt or in vivo hydrolysable ester thereof.

2. A pyrimidine compound according to claim 1 wherein $R^1$ is hydrogen, methyl, —$CH_2CH_2CH_2CF_3$, —$CH_2CH$=$CHBr$, —$CH_2CH$=$CHPh$; or a pharmaceutically acceptable salt or in vivo hydrolysable ester thereof.

3. A pyrimidine compound according to claim 1 wherein $R^x$ is selected from fluoro, chloro, bromo, nitro, amino, cyano, carboxy, methyl, methoxy, ethoxy, ethoxymethyl, vinyl, allyloxymethyl, hydroxymethyl, 2-hydroxyethoxymethyl, 4-hydroxybutoxymethyl, dimethylaminomethyl, diethylaminomethyl, ureidomethyl, formamidomethyl, methylaminomethyl, isopropylaminocarbonyl, phenyl, benzyl, phenethyl, benzoylamino, 4-phenylbutyryl, 2-phenylvinyl (optionally substituted by fluoro), benzyloxymethyl, cyclohexyloxymethyl, 3-cyclopentylpropionyl, morpholino, furyl, imidazolylmethyl, isoxazolyloxymethyl (optionally substituted by methyl), quinolinylaminomethyl, benzothienylaminomethyl, pyrazolylaminomethyl, isoxazolylaminomethyl, thiazolylthiomethyl and tetrazolylthiomethyl; or a pharmaceutically acceptable salt or in vivo hydrolysable ester thereof.

4. A pyrimidine compound according to claim 1 wherein $Q_1$ and $Q_2$ are selected from phenyl, pyridyl, indanyl, indazolyl, indolyl, quinolyl, pyrazolyl or thiazolyl; or a pharmaceutically acceptable salt or in vivo hydrolysable ester thereof.

5. A pyrimidine compound according to claim 1 wherein the substituent of formula (Ia) is 3-amino-2-hydroxypropoxy, 3-methylamino-2-hydroxypropoxy, 3-dimethylaminopropoxy, 3-dimethylamino-2-hydroxypropoxy, 3-ethylamino-2-hydroxypropoxy, 3-diethylaminopropoxy, 3-isopropylaminopropoxy, 3-isopropylamino-2-hydroxypropoxy, 3-isopropylamino-2-hydroxy-2-methylpropoxy, 3-isobutylamino-2-hydroxypropoxy, 3-t-butylamino-2-hydroxypropoxy, 3-ethoxy-2-hydroxypropoxy, 3-(N-isopropyl-N-benzylamino)-2-hydroxypropoxy, 3-(N-allyl-N-methylamino)-2-hydroxypropoxy, 3-(4-methylpiperazin-1-yl)propoxy, 3-(4-methylpiperazin-1-yl)-2-hydroxypropoxy, 3-(4-acetylpiperazin-1-yl)-2-hydroxypropoxy, 3-morpholinopropoxy, 3-morpholino-2-hydroxypropoxy, 3-cyclopentylamino-2-hydroxypropoxy, 3-pyrrolidin-1-yl-2-hydroxypropoxy, 3-imidazol-1-ylpropoxy, 3-(N',N'-dimethylhydrazino)-2-hydroxypropoxy, 3-N',N'-dimethylaminopropylamino, 3-N',N'-dimethylamino-2,2-dimethylpropylamino, 3-N',N'-dimethylamino-2-hydroxy-N-methylpropylamino, 3-N'-isopropylaminopropylamino or 3-imidazol-1-ylpropylamino; or a pharmaceutically acceptable salt or in vivo hydrolysable ester thereof.

6. A pyrimidine compound according to claim 1 wherein $Q_2$ is optionally substituted by halo, hydroxy, cyano, $C_{1-6}$alkyl, hydroxy-$C_{1-3}$alkyl, fluoro-$C_{1-4}$alkyl, $C_{1-4}$alkoxy-$C_{1-3}$alkyl, morpholino, $C_{1-4}$alkoxy, 2-morpholino-ethoxy, 2-imidazo-1-yl-ethoxy, $C_{1-4}$alkylthio, carbamoyl, amino, $C_{2-4}$alkanoylamino, sulphamoyl, phenyl-$C_{1-4}$alkyl, phenyl-$C_{1-4}$alkoxy, phenyl and phenoxy; or a pharmaceutically acceptable salt or in vivo hydrolysable ester thereof.

7. A pyrimidine compound according to claim 1 wherein $Q_1$ is optionally substituted by halo; or a pharmaceutically acceptable salt or in vivo hydrolysable ester thereof.

8. A pyrimidine compound according to claim 1 wherein the substituent of formula (Ia) is on $Q_1$; or a pharmaceutically acceptable salt or in vivo hydrolysable ester thereof.

9. A pyrimidine compound according to claim 1 which is:
5-bromo-2-{4-[2-hydroxy-3-(N,N-dimethylamino)propoxy]anilino}-4-anilinopyrimidine;
5-bromo-2-{4-[2-hydroxy-3-(N,N-dimethylamino)propoxy]anilino}-4-(pyrid-2-ylamino)pyrimidine;
5-bromo-2-{4-[2-hydroxy-3-(isopropylamino)propoxy]anilino}-4-(6-methylpyrid-2-ylamino)pyrimidine;
5-bromo-2-{4-[3-(isopropylamino)propoxy]anilino}-4-anilinopyrimidine;
5-bromo-2-{4-[3-(imidazol-1-yl)propoxy]anilino}-4-(6-methylpyrid-2-ylamino)pyrimidine; or
4-anilino-5-bromo-2-{4-[2-hydroxy-2-methyl-3-(isopropylamino)propoxy]anilino}pyrimidine
or pharmaceutically acceptable salt or in vivo hydrolysable ester thereof.

10. A pyrimidine compound according to claim 1 which is:
5-bromo-2-{4-[2-hydroxy-3-(N,N-dimethylamino)propoxy]anilino}-4-(4-chloroanilino)pyrimidine; or
5-bromo-2-{4-[2-hydroxy-3-(N,N-dimethylamino)propoxy]anilino}-4-[N-(4,4,4-trifluorobutyl)anilino]pyrimidine;
or pharmaceutically acceptable salt or in vivo hydrolysable ester thereof.

11. A process for preparing a pyrimidine compound of the formula (I) as claimed in claim 1 which comprises of:

a) reacting a pyrimidine of formula (II):

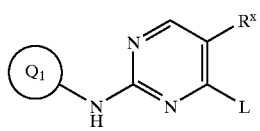

(II)

wherein $Q_1$ and $R^x$ are as defined in claim 1, L is a displaceable group, with a compound of formula (III):

(III)

wherein $R^1$ and $Q_2$ are as defined in claim 1, b) reaction of a pyrimidine of formula (IV):

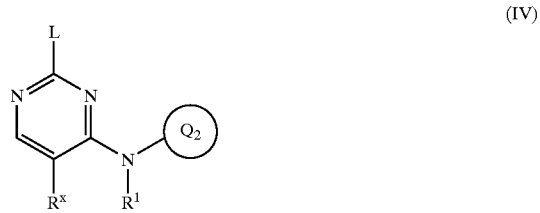

(IV)

$Q_2$, $R^x$, and $R^1$ are as defined in claim 1, L is a displaceable group, with a compound of formula (V):

(V)

where $Q_1$ is as defined in claim 1, c) for compounds of formula (I) as defined in claim 1, where n is 1, 2 or 3, m=1, $Y^2$ is H and $Y^1$ is OH, $NH_2$ or SH by reaction of a 3-membered heteroalkyl ring of formula (VI):

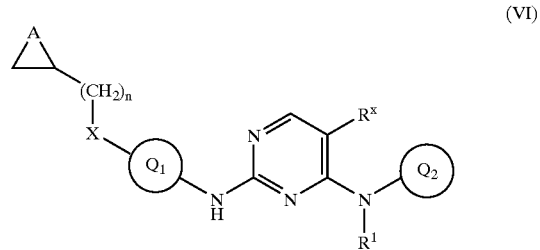

(VI)

wherein $Q_1$, $Q_2$, $R^x$, $R^1$ and X are as defined in claim 1, and A is O, S or NH; with a nucleophile of formula (VII):

Z—D (VII)

wherein Z is as defined in claim 1 and D is H or a suitable counter-ion;

d) for compounds of formula (I) where X is oxygen: by reaction of an alcohol of formula (VIII):

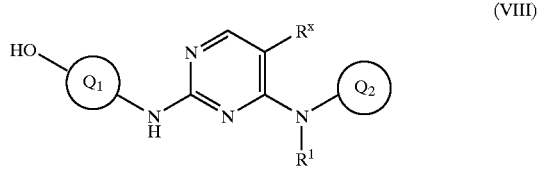

(VIII)

where $Q_1$, $Q_2$, $R^1$ and $R^x$ are as defined in claim 1, with an alcohol of formula (IX):

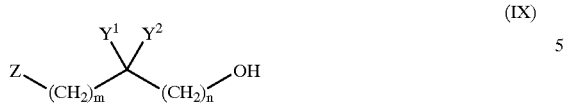

(IX)

where $Y^1$, $Y^2$, m and n are as defined in claim 1, e) for compounds of formula (I) as defined in claim 1 wherein X is —$CH_2$—, —O—, —NH— or —S—, $Y^1$ is OH, $Y^2$ is H and m is 2 or 3; reaction of a compound of formula (X):

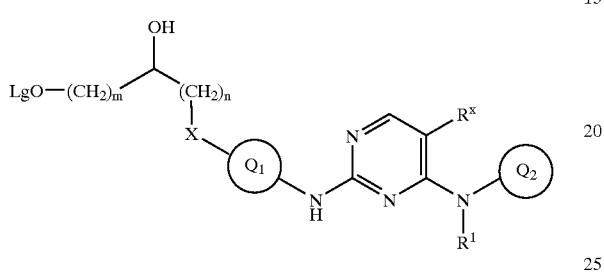

(X)

wherein $Q_1$, $Q_2$, $R^1$, $R^x$, X, m and n are as defined in claim 1, and LgO is a leaving group; with a nucleophile of formula (VII);

f) for compounds of formula (I) as defined in claim 1, wherein X is —$CH_2$—, —O—, —NH— or —S—; $Y^1$ and $Y^2$ are H; n is 1, 2 or 3 and m is 1, 2 or 3; reaction of a compound of formula (XI):

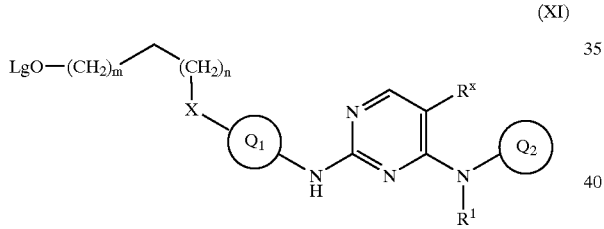

(XI)

wherein $Q_1$, $Q_2$, $R^1$, $R^x$ and X are as defined in claim 1, LgO is a leaving group; with a nucleophile of formula (VII);

g) for compounds of formula (I) as defined in claim 1 wherein X is —O—, —NH— or —S—; $Y^1$ and $Y^2$ are H; n is 1, 2 or 3 and m is 1, 2 or 3; reaction of a compound of formula (XII):

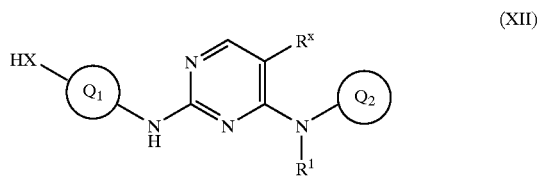

(XII)

$Q_1$, $Q_2$, $R^1$, $R^x$ and X are as defined in claim 1, with a compound of formula (XIII)

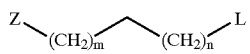

wherein Z, m and n are as defined in claim 1, L is a displaceable group;

h) for compounds of formula (I) as defined in claim 1, in which Z is HS—, by conversion of a thioacetate group in a corresponding compound; and thereafter if necessary:

i) converting a compound of the formula (I) into another compound of the formula (I);

ii) removing any protecting groups;

iii) forming a pharmaceutically acceptable salt or in vivo hydrolysable ester.

12. A pharmaceutical composition which comprises a pyrimidine compound of the formula (I) according to any one of claims 1 to 10, or a pharmaceutically acceptable salt or an in vivo hydrolysable ester thereof, and a pharmaceutically-acceptable diluent or carrier.

13. A method for producing an anti-cancer effect in a warm blooded animal which comprises administering to said animal an effective amount of a pyrimidine compound of the formula (I) according to any one of claims 1 to 10, or a pharmaceutically acceptable salt, or in vivo hydrolysable ester thereof.

* * * * *